US012150447B2

(12) United States Patent
Uchida et al.

(10) Patent No.: US 12,150,447 B2
(45) Date of Patent: Nov. 26, 2024

(54) PLANT GROWTH REGULATOR

(71) Applicants: University of Washington, Seattle, WA (US); National University Corporation Nagoya University, Nagoya (JP)

(72) Inventors: Naoyuki Uchida, Nagoya (JP); Shinya Hagihara, Nagoya (JP); Kenichiro Itami, Nagoya (JP); Rie Iwasaki, Nagoya (JP); Keiko Torii, Seattle, WA (US)

(73) Assignee: University of Washington, Seattle, WA (US)

( * ) Notice: Subject to any disclaimer, the term of this patent is extended or adjusted under 35 U.S.C. 154(b) by 1080 days.

(21) Appl. No.: 16/492,067

(22) PCT Filed: Mar. 8, 2018

(86) PCT No.: PCT/JP2018/008921
§ 371 (c)(1),
(2) Date: Mar. 29, 2021

(87) PCT Pub. No.: WO2018/164214
PCT Pub. Date: Sep. 13, 2018

(65) Prior Publication Data

US 2021/0235697 A1 Aug. 5, 2021

Related U.S. Application Data

(60) Provisional application No. 62/468,642, filed on Mar. 8, 2017.

(51) Int. Cl.

| | |
|---|---|
| ***A01N 43/38*** | (2006.01) |
| ***A01P 21/00*** | (2006.01) |
| ***C07D 209/08*** | (2006.01) |
| ***C07D 209/18*** | (2006.01) |
| ***C07D 405/10*** | (2006.01) |
| ***C07D 409/04*** | (2006.01) |
| ***C12N 15/82*** | (2006.01) |

(52) U.S. Cl.
CPC ........... *A01N 43/38* (2013.01); *C07D 209/08* (2013.01); *C07D 209/18* (2013.01); *C07D 405/10* (2013.01); *C07D 409/04* (2013.01); *C12N 15/8294* (2013.01); *A01P 21/00* (2021.08)

(58) Field of Classification Search
None
See application file for complete search history.

(56) References Cited

U.S. PATENT DOCUMENTS

| | | | |
|---|---|---|---|
| 3,223,514 | A | 12/1965 | Gradsten |
| 3,733,192 | A | 5/1973 | Harris et al. |
| 4,135,909 | A | 1/1979 | Jung et al. |
| 2013/0007920 | A1 | 1/2013 | Nishimura et al. |
| 2015/0289512 | A1 | 10/2015 | Mukumoto et al. |

FOREIGN PATENT DOCUMENTS

| | | | |
|---|---|---|---|
| CN | 104311469 | A | 1/2015 |
| DE | 1916147 | A1 | 10/1969 |
| GB | 1253038 | A | 11/1971 |
| GB | 1499189 | A | 1/1978 |
| GB | 2253848 | A | 9/1992 |
| JP | 49-27787 | B1 | 7/1974 |
| JP | 50-145531 | A | 11/1975 |
| JP | 57-130991 | A | 8/1982 |
| JP | 2007-262009 | A | 10/2007 |
| JP | 2015-89886 | A | 5/2015 |
| WO | 99/54471 | A1 | 10/1999 |
| WO | 2012/019106 | A2 | 2/2012 |
| WO | 2014/073627 | A1 | 5/2014 |

OTHER PUBLICATIONS

Caric, D. et al., "Absorption and fluorescence spectra of ring-substituted indole-3-acetic acids," Biophysical Chemistry, vol. 111, pp. 247-257 (2004).*

Do-Thanh, C. et al., "Design, synthesis, and evaluation of novel auxin mimic herbicides," Journal of Agricultural and Food Chemistry , vol. 64, pp. 3533-3537 (2016).*

Machine translation of JP 2015089886, Espacenet, May 11, 2015.*

Machine translation of JP 2015089886, Clarivate Analytics, May 11, 2015.*

Ainsworth, E.A., and A. Rogers, "The Response of Photosynthesis and Stomatal Conductance to Rising [CO2]: Mechanisms and Environmental Interactions," Plant, Cell and Environment 30(3):258-270, Mar. 2007.

CAS Registration No. 1368656-97-6, SciFinder, Chemical Abstracts Service: Columbus, OH; © 2019 <https://scifinder.cas.org>, 4 pages.

Cowan, I.R., and G.D. Farquhar, "Stomatal Function in Relation to Leaf Metabolism and Environment," Symposia of the Society for Experimental Biology 31:471-505, 1977.

Grones, P., et al., "Auxin-Binding Pocket of ABPI is Crucial for Its Gain-of-Function Cellular and Developmental Roles," Journal of Experimental Botany 66:5055-5065, 2015.

Kole, H.K., et al., "Phosphonate Inhibitors of Protein-Tyrosine and Serine/Threonine Phosphatases," Biochemical Journal 311(3):1025-1031, 1995.

Latham, J., et al., "Integrated Catalysis Opens New Arylation Pathways via Regiodivergent Enzymatic C-H Activation," Nature Communications, 2016, pp. 1-8.

Suvorov, N.N., et al., "Synthesis of 5-alkoxy- and 5-aryloxy-y-3-indolylbutyric Acids," Doklady Akademii Nauk SSSR, 1955, vol. 101, pp. 103-106.

(Continued)

*Primary Examiner* — John Pak
(74) *Attorney, Agent, or Firm* — Christensen O'Connor Johnson Kindness PLLC

(57) ABSTRACT

Providing an auxin derivative that can exert its intended effect more efficiently, while reducing any unintended effects. A compound represented by the General Formula (1) having a specific substituent at the 5- and/or 6-position of the auxin indole ring.

4 Claims, 4 Drawing Sheets

Specification includes a Sequence Listing.

(56) References Cited

OTHER PUBLICATIONS

Suvorov, N.N., et al., "Synthesis of Phenyl-Substituted 4-(3-indolyl)butyric Acids," Doklady Akademii Nauk SSSR, 1953, vol. 91, pp. 1345-1348.
Tan, X., et al., "Mechanism of Auxin Perception by the TIR1 Ubiquitin Ligase," Nature 446:640-644, Apr. 2007.
Tanaka, Y., et al., "Enhancement of Leaf Photosynthetic Apacity Through Increased Stomatal Density in *Arabidopsis*," New Phytologist 198(3):757-764, 2013.
Tsuda, E., et al., "Alkoxy-Auxins Are Selective Inhibitors of Auxin Transport Mediated by PIN, ABCB, and AUX1 Transporters," Journal of Biological Chemistry 286:2354-2364, 2011.
Uchida, N., et al., "Chemical Hijacking of Auxin Signaling With an Engineered Auxin-TIR1 Pair," Nature Chemical Biology 14:299-305, Jan. 2018.
Van Houtte, H., et al., "Overexpression of the Trehalase Gene AtTRE1 Leads to Increased Drought Stress Tolerance in *Arabidopsis* and Is Involved in Abscisic Acid-Induced Stomatal Closure," Plant Physiology 161(3):1158-1171, Mar. 2013.
Veldstra, H., et al., "Researches on Plant Growth Regulators XXII. Structure/Activity VII: Sulphonic Acids and Related Compounds," Recueil des Travaux Chimiques des Pays-Bas et de la Belgique 73:23-34, 1954.
International Search Report mailed Jun. 5, 2018, issued in corresponding International Application No. PCT/JP2018/008921, filed Mar. 8, 2018, 5 pages.

* cited by examiner

SEQUENCE LISTING

```
<160> NUMBER OF SEQ ID NOS: 5

<210> SEQ ID NO 1
<211> LENGTH: 594
<212> TYPE: PRT
<213> ORGANISM: Artificial Sequence
<220> FEATURE:
<223> OTHER INFORMATION: Synthetic

<400> SEQUENCE: 1

Met Gln Lys Arg Ile Ala Leu Ser Phe Pro Glu Glu Val Leu Glu His
1               5                   10                  15

Val Phe Ser Phe Ile Gln Leu Asp Lys Asp Arg Asn Ser Val Ser Leu
            20                  25                  30

Val Cys Lys Ser Trp Tyr Glu Ile Glu Arg Trp Cys Arg Arg Lys Val
        35                  40                  45

Phe Ile Gly Asn Cys Tyr Ala Val Ser Pro Ala Thr Val Ile Arg Arg
    50                  55                  60
```

-continued

```
Phe Pro Lys Val Arg Ser Val Glu Leu Lys Gly Lys Pro His Phe Ala
65                  70                  75                  80

Asp Phe Asn Leu Val Pro Asp Gly Trp Gly Gly Tyr Val Tyr Pro Trp
                85                  90                  95

Ile Glu Ala Met Ser Ser Ser Tyr Thr Trp Leu Glu Glu Ile Arg Leu
            100                 105                 110

Lys Arg Met Val Val Thr Asp Asp Cys Leu Glu Leu Ile Ala Lys Ser
        115                 120                 125

Phe Lys Asn Phe Lys Val Leu Val Leu Ser Ser Cys Glu Gly Phe Ser
    130                 135                 140

Thr Asp Gly Leu Ala Ala Ile Ala Ala Thr Cys Arg Asn Leu Lys Glu
145                 150                 155                 160

Leu Asp Leu Arg Glu Ser Asp Val Asp Asp Val Ser Gly His Trp Leu
                165                 170                 175

Ser His Phe Pro Asp Thr Tyr Thr Ser Leu Val Ser Leu Asn Ile Ser
            180                 185                 190

Cys Leu Ala Ser Glu Val Ser Phe Ser Ala Leu Glu Arg Leu Val Thr
        195                 200                 205

Arg Cys Pro Asn Leu Lys Ser Leu Lys Leu Asn Arg Ala Val Pro Leu
    210                 215                 220

Glu Lys Leu Ala Thr Leu Leu Gln Arg Ala Pro Gln Leu Glu Glu Leu
225                 230                 235                 240

Gly Thr Gly Gly Tyr Thr Ala Glu Val Arg Pro Asp Val Tyr Ser Gly
                245                 250                 255

Leu Ser Val Ala Leu Ser Gly Cys Lys Glu Leu Arg Cys Leu Ser Gly
            260                 265                 270

Phe Trp Asp Ala Val Pro Ala Tyr Leu Pro Ala Val Tyr Ser Val Cys
        275                 280                 285

Ser Arg Leu Thr Thr Leu Asn Leu Ser Tyr Ala Thr Val Gln Ser Tyr
    290                 295                 300

Asp Leu Val Lys Leu Leu Cys Gln Cys Pro Lys Leu Gln Arg Leu Trp
305                 310                 315                 320

Val Leu Asp Tyr Ile Glu Asp Ala Gly Leu Glu Val Leu Ala Ser Thr
                325                 330                 335

Cys Lys Asp Leu Arg Glu Leu Arg Val Phe Pro Ser Glu Pro Phe Val
            340                 345                 350

Met Glu Pro Asn Val Ala Leu Thr Glu Gln Gly Leu Val Ser Val Ser
        355                 360                 365

Met Gly Cys Pro Lys Leu Glu Ser Val Leu Tyr Phe Cys Arg Gln Met
    370                 375                 380

Thr Asn Ala Ala Leu Ile Thr Ile Ala Arg Asn Arg Pro Asn Met Thr
385                 390                 395                 400

Arg Phe Arg Leu Cys Ile Ile Glu Pro Lys Ala Pro Asp Tyr Leu Thr
                405                 410                 415

Leu Glu Pro Leu Asp Ile Gly Phe Gly Ala Ile Val Glu His Cys Lys
            420                 425                 430

Asp Leu Arg Arg Leu Ser Leu Ser Gly Leu Leu Thr Asp Lys Val Phe
        435                 440                 445

Glu Tyr Ile Gly Thr Tyr Ala Lys Lys Met Glu Met Leu Ser Val Ala
    450                 455                 460

Phe Ala Gly Asp Ser Asp Leu Gly Met His His Val Leu Ser Gly Cys
465                 470                 475                 480

Asp Ser Leu Arg Lys Leu Glu Ile Arg Asp Cys Pro Phe Gly Asp Lys
```

```
                485                 490                 495

Ala Leu Leu Ala Asn Ala Ser Lys Leu Glu Thr Met Arg Ser Leu Trp
            500                 505                 510

Met Ser Ser Cys Ser Val Ser Phe Gly Ala Cys Lys Leu Leu Gly Gln
        515                 520                 525

Lys Met Pro Lys Leu Asn Val Glu Val Ile Asp Glu Arg Gly Ala Pro
    530                 535                 540

Asp Ser Arg Pro Glu Ser Cys Pro Val Glu Arg Val Phe Ile Tyr Arg
545                 550                 555                 560

Thr Val Ala Gly Pro Arg Phe Asp Met Pro Gly Phe Val Trp Asn Met
                565                 570                 575

Asp Gln Asp Ser Thr Met Arg Phe Ser Arg Gln Ile Ile Thr Thr Asn
            580                 585                 590

Gly Leu


<210> SEQ ID NO 2
<211> LENGTH: 594
<212> TYPE: PRT
<213> ORGANISM: Artificial Sequence
<220> FEATURE:
<223> OTHER INFORMATION: Synthetic

<400> SEQUENCE: 2

Met Gln Lys Arg Ile Ala Leu Ser Phe Pro Glu Glu Val Leu Glu His
1               5                   10                  15

Val Phe Ser Phe Ile Gln Leu Asp Lys Asp Arg Asn Ser Val Ser Leu
            20                  25                  30

Val Cys Lys Ser Trp Tyr Glu Ile Glu Arg Trp Cys Arg Arg Lys Val
        35                  40                  45

Phe Ile Gly Asn Cys Tyr Ala Val Ser Pro Ala Thr Val Ile Arg Arg
    50                  55                  60

Phe Pro Lys Val Arg Ser Val Glu Leu Lys Gly Lys Pro His Gly Ala
65                  70                  75                  80

Asp Phe Asn Leu Val Pro Asp Gly Trp Gly Gly Tyr Val Tyr Pro Trp
                85                  90                  95

Ile Glu Ala Met Ser Ser Ser Tyr Thr Trp Leu Glu Glu Ile Arg Leu
            100                 105                 110

Lys Arg Met Val Val Thr Asp Asp Cys Leu Glu Leu Ile Ala Lys Ser
        115                 120                 125

Phe Lys Asn Phe Lys Val Leu Val Leu Ser Ser Cys Glu Gly Phe Ser
    130                 135                 140

Thr Asp Gly Leu Ala Ala Ile Ala Ala Thr Cys Arg Asn Leu Lys Glu
145                 150                 155                 160

Leu Asp Leu Arg Glu Ser Asp Val Asp Asp Val Ser Gly His Trp Leu
                165                 170                 175

Ser His Phe Pro Asp Thr Tyr Thr Ser Leu Val Ser Leu Asn Ile Ser
            180                 185                 190

Cys Leu Ala Ser Glu Val Ser Phe Ser Ala Leu Glu Arg Leu Val Thr
        195                 200                 205

Arg Cys Pro Asn Leu Lys Ser Leu Lys Leu Asn Arg Ala Val Pro Leu
    210                 215                 220

Glu Lys Leu Ala Thr Leu Leu Gln Arg Ala Pro Gln Leu Glu Glu Leu
225                 230                 235                 240

Gly Thr Gly Gly Tyr Thr Ala Glu Val Arg Pro Asp Val Tyr Ser Gly
                245                 250                 255
```

Leu Ser Val Ala Leu Ser Gly Cys Lys Glu Leu Arg Cys Leu Ser Gly
260 265 270

Phe Trp Asp Ala Val Pro Ala Tyr Leu Pro Ala Val Tyr Ser Val Cys
275 280 285

Ser Arg Leu Thr Thr Leu Asn Leu Ser Tyr Ala Thr Val Gln Ser Tyr
290 295 300

Asp Leu Val Lys Leu Leu Cys Gln Cys Pro Lys Leu Gln Arg Leu Trp
305 310 315 320

Val Leu Asp Tyr Ile Glu Asp Ala Gly Leu Glu Val Leu Ala Ser Thr
325 330 335

Cys Lys Asp Leu Arg Glu Leu Arg Val Phe Pro Ser Glu Pro Phe Val
340 345 350

Met Glu Pro Asn Val Ala Leu Thr Glu Gln Gly Leu Val Ser Val Ser
355 360 365

Met Gly Cys Pro Lys Leu Glu Ser Val Leu Tyr Phe Cys Arg Gln Met
370 375 380

Thr Asn Ala Ala Leu Ile Thr Ile Ala Arg Asn Arg Pro Asn Met Thr
385 390 395 400

Arg Phe Arg Leu Cys Ile Ile Glu Pro Lys Ala Pro Asp Tyr Leu Thr
405 410 415

Leu Glu Pro Leu Asp Ile Gly Phe Gly Ala Ile Val Glu His Cys Lys
420 425 430

Asp Leu Arg Arg Leu Ser Leu Ser Gly Leu Leu Thr Asp Lys Val Phe
435 440 445

Glu Tyr Ile Gly Thr Tyr Ala Lys Lys Met Glu Met Leu Ser Val Ala
450 455 460

Phe Ala Gly Asp Ser Asp Leu Gly Met His His Val Leu Ser Gly Cys
465 470 475 480

Asp Ser Leu Arg Lys Leu Glu Ile Arg Asp Cys Pro Phe Gly Asp Lys
485 490 495

Ala Leu Leu Ala Asn Ala Ser Lys Leu Glu Thr Met Arg Ser Leu Trp
500 505 510

Met Ser Ser Cys Ser Val Ser Phe Gly Ala Cys Lys Leu Leu Gly Gln
515 520 525

Lys Met Pro Lys Leu Asn Val Glu Val Ile Asp Glu Arg Gly Ala Pro
530 535 540

Asp Ser Arg Pro Glu Ser Cys Pro Val Glu Arg Val Phe Ile Tyr Arg
545 550 555 560

Thr Val Ala Gly Pro Arg Phe Asp Met Pro Gly Phe Val Trp Asn Met
565 570 575

Asp Gln Asp Ser Thr Met Arg Phe Ser Arg Gln Ile Ile Thr Thr Asn
580 585 590

Gly Leu

<210> SEQ ID NO 3
<211> LENGTH: 93
<212> TYPE: PRT
<213> ORGANISM: Artificial Sequence
<220> FEATURE:
<223> OTHER INFORMATION: Synthetic

<400> SEQUENCE: 3

Met Asp Glu Phe Val Asn Leu Lys Glu Thr Glu Leu Arg Leu Gly Leu
1 5 10 15

Pro Gly Thr Asp Asn Val Cys Glu Ala Lys Glu Arg Val Ser Cys Cys
20 25 30

Asn Asn Asn Asn Lys Arg Val Leu Ser Thr Asp Thr Glu Lys Glu Ile
35 40 45

Glu Ser Ser Ser Arg Lys Thr Glu Thr Ser Pro Pro Arg Lys Ala Gln
50 55 60

Ile Val Gly Trp Pro Pro Val Arg Ser Tyr Arg Lys Asn Asn Ile Gln
65 70 75 80

Ser Lys Lys Asn Glu Ser Glu His Glu Gly Gln Gly Ile
85 90

<210> SEQ ID NO 4
<211> LENGTH: 594
<212> TYPE: PRT
<213> ORGANISM: Artificial Sequence
<220> FEATURE:
<223> OTHER INFORMATION: Synthetic

<400> SEQUENCE: 4

Met Gln Lys Arg Ile Ala Leu Ser Phe Pro Glu Glu Val Leu Glu His
1 5 10 15

Val Phe Ser Phe Ile Gln Leu Asp Lys Asp Arg Asn Ser Val Ser Leu
20 25 30

Val Cys Lys Ser Trp Tyr Glu Ile Glu Arg Trp Cys Arg Arg Lys Val
35 40 45

Phe Ile Gly Asn Cys Tyr Ala Val Ser Pro Ala Thr Val Ile Arg Arg
50 55 60

Phe Pro Lys Val Arg Ser Val Glu Leu Lys Gly Lys Pro His Ala Ala
65 70 75 80

Asp Phe Asn Leu Val Pro Asp Gly Trp Gly Gly Tyr Val Tyr Pro Trp
85 90 95

Ile Glu Ala Met Ser Ser Ser Tyr Thr Trp Leu Glu Glu Ile Arg Leu
100 105 110

Lys Arg Met Val Val Thr Asp Asp Cys Leu Glu Leu Ile Ala Lys Ser
115 120 125

Phe Lys Asn Phe Lys Val Leu Val Leu Ser Ser Cys Glu Gly Phe Ser
130 135 140

Thr Asp Gly Leu Ala Ala Ile Ala Ala Thr Cys Arg Asn Leu Lys Glu
145 150 155 160

Leu Asp Leu Arg Glu Ser Asp Val Asp Asp Val Ser Gly His Trp Leu
165 170 175

Ser His Phe Pro Asp Thr Tyr Thr Ser Leu Val Ser Leu Asn Ile Ser
180 185 190

Cys Leu Ala Ser Glu Val Ser Phe Ser Ala Leu Glu Arg Leu Val Thr
195 200 205

Arg Cys Pro Asn Leu Lys Ser Leu Lys Leu Asn Arg Ala Val Pro Leu
210 215 220

Glu Lys Leu Ala Thr Leu Leu Gln Arg Ala Pro Gln Leu Glu Glu Leu
225 230 235 240

Gly Thr Gly Gly Tyr Thr Ala Glu Val Arg Pro Asp Val Tyr Ser Gly
245 250 255

Leu Ser Val Ala Leu Ser Gly Cys Lys Glu Leu Arg Cys Leu Ser Gly
260 265 270

Phe Trp Asp Ala Val Pro Ala Tyr Leu Pro Ala Val Tyr Ser Val Cys
275 280 285

Ser Arg Leu Thr Thr Leu Asn Leu Ser Tyr Ala Thr Val Gln Ser Tyr
290 295 300

Asp Leu Val Lys Leu Leu Cys Gln Cys Pro Lys Leu Gln Arg Leu Trp
305 310 315 320

Val Leu Asp Tyr Ile Glu Asp Ala Gly Leu Glu Val Leu Ala Ser Thr
325 330 335

Cys Lys Asp Leu Arg Glu Leu Arg Val Phe Pro Ser Glu Pro Phe Val
340 345 350

Met Glu Pro Asn Val Ala Leu Thr Glu Gln Gly Leu Val Ser Val Ser
355 360 365

Met Gly Cys Pro Lys Leu Glu Ser Val Leu Tyr Phe Cys Arg Gln Met
370 375 380

Thr Asn Ala Ala Leu Ile Thr Ile Ala Arg Asn Arg Pro Asn Met Thr
385 390 395 400

Arg Phe Arg Leu Cys Ile Ile Glu Pro Lys Ala Pro Asp Tyr Leu Thr
405 410 415

Leu Glu Pro Leu Asp Ile Gly Phe Gly Ala Ile Val Glu His Cys Lys
420 425 430

Asp Leu Arg Arg Leu Ser Leu Ser Gly Leu Leu Thr Asp Lys Val Phe
435 440 445

Glu Tyr Ile Gly Thr Tyr Ala Lys Lys Met Glu Met Leu Ser Val Ala
450 455 460

Phe Ala Gly Asp Ser Asp Leu Gly Met His His Val Leu Ser Gly Cys
465 470 475 480

Asp Ser Leu Arg Lys Leu Glu Ile Arg Asp Cys Pro Phe Gly Asp Lys
485 490 495

Ala Leu Leu Ala Asn Ala Ser Lys Leu Glu Thr Met Arg Ser Leu Trp
500 505 510

Met Ser Ser Cys Ser Val Ser Phe Gly Ala Cys Lys Leu Leu Gly Gln
515 520 525

Lys Met Pro Lys Leu Asn Val Glu Val Ile Asp Glu Arg Gly Ala Pro
530 535 540

Asp Ser Arg Pro Glu Ser Cys Pro Val Glu Arg Val Phe Ile Tyr Arg
545 550 555 560

Thr Val Ala Gly Pro Arg Phe Asp Met Pro Gly Phe Val Trp Asn Met
565 570 575

Asp Gln Asp Ser Thr Met Arg Phe Ser Arg Gln Ile Ile Thr Thr Asn
580 585 590

Gly Leu

<210> SEQ ID NO 5
<211> LENGTH: 594
<212> TYPE: PRT
<213> ORGANISM: Artificial Sequence
<220> FEATURE:
<223> OTHER INFORMATION: Synthetic

<400> SEQUENCE: 5

Met Gln Lys Arg Ile Ala Leu Ser Phe Pro Glu Glu Val Leu Glu His
1 5 10 15

Val Phe Ser Phe Ile Gln Leu Asp Lys Asp Arg Asn Ser Val Ser Leu
20 25 30

Val Cys Lys Ser Trp Tyr Glu Ile Glu Arg Trp Cys Arg Arg Lys Val
35 40 45

Phe Ile Gly Asn Cys Tyr Ala Val Ser Pro Ala Thr Val Ile Arg Arg

```
    50                  55                  60

Phe Pro Lys Val Arg Ser Val Glu Leu Lys Gly Lys Pro His Ser Ala
65                  70                  75                  80

Asp Phe Asn Leu Val Pro Asp Gly Trp Gly Gly Tyr Val Tyr Pro Trp
                85                  90                  95

Ile Glu Ala Met Ser Ser Ser Tyr Thr Trp Leu Glu Glu Ile Arg Leu
            100                 105                 110

Lys Arg Met Val Val Thr Asp Asp Cys Leu Glu Leu Ile Ala Lys Ser
        115                 120                 125

Phe Lys Asn Phe Lys Val Leu Val Leu Ser Ser Cys Glu Gly Phe Ser
    130                 135                 140

Thr Asp Gly Leu Ala Ala Ile Ala Ala Thr Cys Arg Asn Leu Lys Glu
145                 150                 155                 160

Leu Asp Leu Arg Glu Ser Asp Val Asp Asp Val Ser Gly His Trp Leu
                165                 170                 175

Ser His Phe Pro Asp Thr Tyr Thr Ser Leu Val Ser Leu Asn Ile Ser
            180                 185                 190

Cys Leu Ala Ser Glu Val Ser Phe Ser Ala Leu Glu Arg Leu Val Thr
        195                 200                 205

Arg Cys Pro Asn Leu Lys Ser Leu Lys Leu Asn Arg Ala Val Pro Leu
    210                 215                 220

Glu Lys Leu Ala Thr Leu Leu Gln Arg Ala Pro Gln Leu Glu Glu Leu
225                 230                 235                 240

Gly Thr Gly Gly Tyr Thr Ala Glu Val Arg Pro Asp Val Tyr Ser Gly
                245                 250                 255

Leu Ser Val Ala Leu Ser Gly Cys Lys Glu Leu Arg Cys Leu Ser Gly
            260                 265                 270

Phe Trp Asp Ala Val Pro Ala Tyr Leu Pro Ala Val Tyr Ser Val Cys
        275                 280                 285

Ser Arg Leu Thr Thr Leu Asn Leu Ser Tyr Ala Thr Val Gln Ser Tyr
    290                 295                 300

Asp Leu Val Lys Leu Leu Cys Gln Cys Pro Lys Leu Gln Arg Leu Trp
305                 310                 315                 320

Val Leu Asp Tyr Ile Glu Asp Ala Gly Leu Glu Val Leu Ala Ser Thr
                325                 330                 335

Cys Lys Asp Leu Arg Glu Leu Arg Val Phe Pro Ser Glu Pro Phe Val
            340                 345                 350

Met Glu Pro Asn Val Ala Leu Thr Glu Gln Gly Leu Val Ser Val Ser
        355                 360                 365

Met Gly Cys Pro Lys Leu Glu Ser Val Leu Tyr Phe Cys Arg Gln Met
    370                 375                 380

Thr Asn Ala Ala Leu Ile Thr Ile Ala Arg Asn Arg Pro Asn Met Thr
385                 390                 395                 400

Arg Phe Arg Leu Cys Ile Ile Glu Pro Lys Ala Pro Asp Tyr Leu Thr
                405                 410                 415

Leu Glu Pro Leu Asp Ile Gly Phe Gly Ala Ile Val Glu His Cys Lys
            420                 425                 430

Asp Leu Arg Arg Leu Ser Leu Ser Gly Leu Leu Thr Asp Lys Val Phe
        435                 440                 445

Glu Tyr Ile Gly Thr Tyr Ala Lys Lys Met Glu Met Leu Ser Val Ala
    450                 455                 460

Phe Ala Gly Asp Ser Asp Leu Gly Met His His Val Leu Ser Gly Cys
465                 470                 475                 480
```

-continued

```
Asp Ser Leu Arg Lys Leu Glu Ile Arg Asp Cys Pro Phe Gly Asp Lys
                485                 490                 495

Ala Leu Leu Ala Asn Ala Ser Lys Leu Glu Thr Met Arg Ser Leu Trp
            500                 505                 510

Met Ser Ser Cys Ser Val Ser Phe Gly Ala Cys Lys Leu Leu Gly Gln
        515                 520                 525

Lys Met Pro Lys Leu Asn Val Glu Val Ile Asp Glu Arg Gly Ala Pro
    530                 535                 540

Asp Ser Arg Pro Glu Ser Cys Pro Val Glu Arg Val Phe Ile Tyr Arg
545                 550                 555                 560

Thr Val Ala Gly Pro Arg Phe Asp Met Pro Gly Phe Val Trp Asn Met
                565                 570                 575

Asp Gln Asp Ser Thr Met Arg Phe Ser Arg Gln Ile Ile Thr Thr Asn
            580                 585                 590

Gly Leu
```

PLANT GROWTH REGULATOR

TECHNICAL FIELD

The present invention is related to plant growth regulators and methods etc. of plant growth regulation.

PRIOR ART

Auxin has long been known as a plant hormone that causes a variety of physiological effects. In recent years, with the discovery of the auxin receptor, the mechanism of its action has been elucidated in more detail. When auxin binds to the auxin receptor (TIR1: Transport Inhibitor Response 1) in the cell, a transcription factor (Aux/IAA) further binds to this, which promotes degradation of the transcription factor by the ubiquitin-proteasome pathway. This results in changes to the expression of a group of genes that are transcriptionally controlled by said transcription factors. Induction of such auxin response signals leads to exertion of a various growth regulation effects in plants, such as root elongation control, lateral root growth, gravitropism, cell elongation, side organ induction in apical meristem, and branching control.

Therefore, auxin is widely used as an active ingredient in plant growth regulators. There exists a problem that over-application of auxin can lead to plant death (Non-Patent Literature 1). An example shown in Patent Literature 1 discloses, however, an auxin derivative with reduced risk of plant death.

PRIOR ART DOCUMENTS

Patent Literature

Patent Literature 1] Japanese Unexamined Patent Application Publication No. 2015-089886

Non-Patent Literature

[Non-Patent Literature 1] Grossmann K. (2007) Plant Signaling $ Behavior 2: 421-423. "Auxin Herbicide Action"

SUMMARY OF THE INVENTION

Problems to be Solved by the Invention

Auxin exerts various effects on plants depending on the target tissue, etc. Therefore, application of auxin to a plant can have an effect that is other than what is intended, or an undesirable or death-inducing effect compared to what was intended.

For this reason, the present invention aims to provide an auxin derivative that can exert its intended effect more efficiently, while reducing any unintended effects.

Means for Solving the Problem

Over the course of intensive research in view of the aforementioned problem, the inventors came up with the idea of using an auxin derivative that plants cannot recognize as auxin, in combination with a mutated auxin receptor that does not recognize auxin, but produces an auxin-response signal by recognizing the aforementioned auxin derivative. It is believed that, given such a combination, application of the auxin derivative to a plant expressing the mutated auxin receptor only in target tissue would allow specific production of auxin-response signals only in the target tissue.

As a result of further intensive studies based on this idea, we found that an auxin derivative having a specific substituent in the 5 and/or 6-position of the auxin indole ring has reduced binding affinity to the endogenous auxin receptor, while having good binding affinity with the reduced auxin-sensitivity auxin receptor. It was also found that by applying this auxin derivative to plants expressing the reduced auxin-sensitivity auxin receptor in specific tissues, it is possible to efficiently exert the growth regulating effect in the tissue. The inventors advanced the research based on these findings and completed the present invention.

In other words, the present invention includes the following aspects.

Claim 1. General Formula (1):

[Chemical Formula 1]

(1)

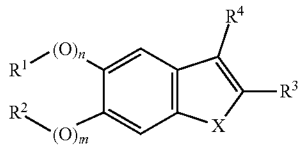

[wherein n and m are the same or different, represents 0 or 1. $R^1$ and $R^2$ are the same or different and are each a hydrogen atom, an adamantyl group that may be substituted, an aryl group that may be substituted, an alkyl group that may be substituted, or a heterocyclic group that may be substituted (except when $R^1$ and $R^2$ are both hydrogen atoms at the same time). One of $R^3$ and $R^4$ represents a carboxyalkyl group, and the other represents a hydrogen atom. X represents —NH— or —CH═CH—.] A growth regulator of plants expressing the reduced auxin-sensitivity auxin receptor, containing the compound represented by its agriculturally acceptable salt, hydrate or solvate.

Claim 2. The compound represented by the General Formula (1) above is the compound represented by the General Formula (1A):

[Chemical Formula 2]

(1A)

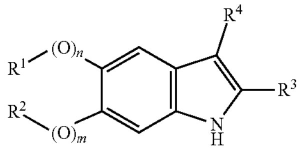

[wherein n, m, $R^1$, $R^2$, $R^3$ and $R^4$ are as defined above.] which is the growth regulator described in Claim 1.

Claim 3. The growth regulator described in Claim 1 or 2, wherein the previously mentioned $R^3$ is a hydrogen atom, and $R^4$ is a carboxyalkyl group.

Claim 4. The growth regulator described in any one of Claims 1 to 3,wherein $R^1$ is an adamantyl group that may be substituted, an aryl group that may be substituted, or an alkyl group that may be substituted.

Claim 5. The compound represented by the General Formula (1) above is the compound represented by the General Formula (1A1a):

During

[Chemical Formula 3]

(1A1a)

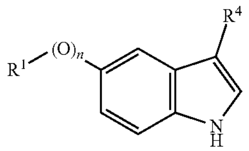

[wherein n and $R^1$ are as defined above. $R^4$ is a carboxyalkyl group.], which is the growth regulator described in any one of Claims 1 to 4.

Claim 6. The growth regulator described in any one of Claims 1 to 5,wherein the previously mentioned aryl group is a phenyl group, a phenylalkyl group, or a naphthyl group.

Claim 7. The growth regulator described in any one of Claims 1 to 6,wherein the previously mentioned alkyl group has 4 to 20 carbon atoms.

Claim 8. The growth regulator described in any one of Claims 1 to 7,wherein the previously mentioned adamantyl group, aryl group, alkyl group, and the heterocyclic group are substituted by at least one substituent selected from the group consisting of an alkyl group, an alkoxy group, a halogen atom, an aryl group, and an aryloxy group.

Claim 9. The growth regulator described in any one of Claims 1 to 8,wherein one of previously mentioned $R^1$-$(O)_n$— and $R^2$-$(O)_m$— is represented by

[Chemical Formula 4]

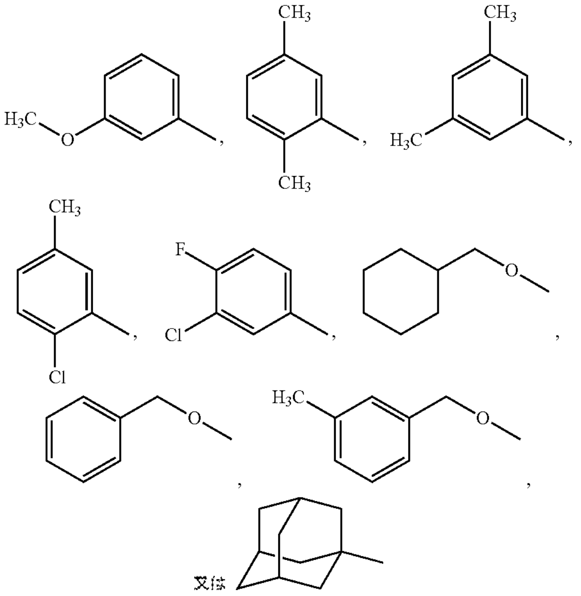

and the other is a hydrogen atom.

Claim 10. The growth regulator described in any one of Claims 1 to 9,wherein the previously mentioned reduced auxin-sensitivity auxin receptor is an auxin receptor resulting from the replacement of the amino acid residue that interacts with the benzene ring in the auxin indole ring with another amino acid residue.

Claim 11. The growth regulator described in Claim 10, wherein the other amino acid mentioned previously is glycine.

Claim 12. General Formula (1):

[Chemical Formula 5]

(1)

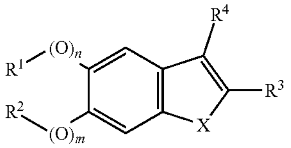

[wherein n and m are the same or different and represents 0 or 1. $R^2$-$(O)_m$ is a hydrogen atom, and when n is 0, $R^4$ is:

(a) An adamantyl group which may be substituted, (b) An aryl group which may be substituted by at least one substituent selected from the group consisting of an aryl group and an aryloxy group, or by an alkyl group, alkoxy group, or a halogen atom, as well as at least one substituent selected from the group consisting of an alkyl group, an alkoxy group, a halogen atom, and an aryl group, OR (c) An alkyl group with 5 to 20 carbon atoms which may be substituted by at least one substituent selected from the group consisting of an alkyl group, an alkoxy group, a halogen atom, an aryl group, and an aryloxy group; OR when n is 1, $R^4$ is:

(d) An adamantyl group that may be substituted, (e) A phenyl group that may be substituted by fewer than two substituents, a naphthyl group that may be substituted, or a benzyl group substituted with at least one substituent selected from the group consisting of an alkyl group, a halogen atom, an aryl group and an aryloxy group, OR (f) An alkyl group having 6 to 20 carbon atoms that is substituted with at least one substituent selected from the group consisting of a cycloalkyl group, an alkoxy group, a halogen atom, an aryl group, and an aryloxy group; OR $R^1$-$(O)_n$— is a hydrogen atom and when m is 0, $R^2$ is:

(g) An adamantyl group that may be substituted (h) (h1) An aryl group substituted by at least one substituent selected from the group consisting of an alkoxy group, an aryl group and an aryloxy group, OR (h2) An aryl group which may be substituted by two or more substituents comprising an alkyl group or a halogen atom, and at least one substituent selected from the group consisting of an alkyl group, an alkoxy group, a halogen atom, an aryl group, and an aryloxy group, OR (i) An alkyl group having 4 to 20 carbon atoms that may be substituted; OR when m is 1, $R^2$ is:

(j) An adamantyl group that may be substituted;

(k) A phenyl group or a naphthyl group which may be substituted by at least one substituent selected from the group consisting of an alkyl group, an alkoxy group, a halogen, an aryl group and an aryloxy group, OR (l) An alkyl group having 4 to 20 carbon atoms that may be substituted. One of $R^3$ and $R^4$ represents a carboxyalkyl group, and the other represents a hydrogen atom. X represents —NH— or —CH=CH—.] A compound represented by Claim 13. General Formula (1):

[Chemical Formula 6]

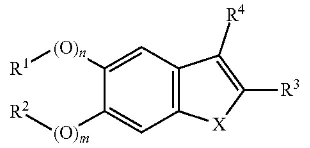

(1)

[wherein n and m are the same or different and represents 0 or 1. $R^1$ and $R^2$ are the same or different and each represents a hydrogen atom, an aryl group that may be substituted, or an alkyl group that may be substituted (except when $R^1$ and $R^2$ are both hydrogen atoms at the same time). One of $R^3$ and $R^4$ represents a carboxyalkyl group, and the other represents a hydrogen atom. X represents —NH— or —CH═CH—.] A method of regulating the growth of a plant expressing the reduced auxin-sensitivity auxin receptor, which includes applying the compound represented by, its agriculturally acceptable salt, hydrate or solvate to plants expressing the reduced auxin-sensitivity auxin receptor.

Claim 14. A reduced auxin-sensitivity auxin receptor resulting from the replacement of the amino acid residue in the auxin receptor that interacts with the benzene ring in the auxin indole ring with another amino acid residue.

Claim 15. Furthermore, General Formula (1):

[Chemical Formula 7]

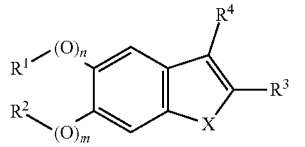

(1)

[wherein n and m are the same or different and represents 0 or 1. $R^1$ and $R^2$ are the same or different and are each a hydrogen atom, an adamantyl group that may be substituted, an aryl group that may be substituted, an alkyl group that may be substituted, or a heterocyclic group that may be substituted (except when $R^1$ and $R^2$ are both hydrogen atoms at the same time). One of $R^3$ and $R^4$ represents a carboxyalkyl group, and the other represents a hydrogen atom. X represents —NH— or —CH═CH—.] A reduced auxin-sensitivity auxin receptor having binding affinity to the compound represented by, its agriculturally acceptable salt, hydrate or solvate.

section 16. A reduced auxin-sensitivity auxin receptor TIR1 as described in Claims 14 or 15, wherein the other amino acid residue mentioned previously is alanine, serine or glycine.

Claim 17. A polynucleotide encoding the reduced auxin-sensitivity auxin receptor TIR described in any of Claims 14 to 16.

Claim 18. A cell that expresses the reduced auxin-sensitivity auxin receptor TIR described in any of Claims 14 to 16.

Claim 19. A plant comprising the cell described in Claim 18.

Effects of the Invention

The auxin derivative in the present invention has its binding affinity to the endogenous auxin receptor reduced and exhibits good binding affinity with the reduced auxin-sensitivity auxin receptor. For this reason, if this auxin derivative is applied to a plant expressing the reduced auxin-sensitivity auxin receptor in specific tissues, it would be possible efficiently to produce the intended effect while reducing any unintended effects. Therefore, the auxin derivative of the present invention is useful as a plant growth regulator that is based on the auxin response signal.

EMBODIMENT OF THE INVENTION

Figure 1:
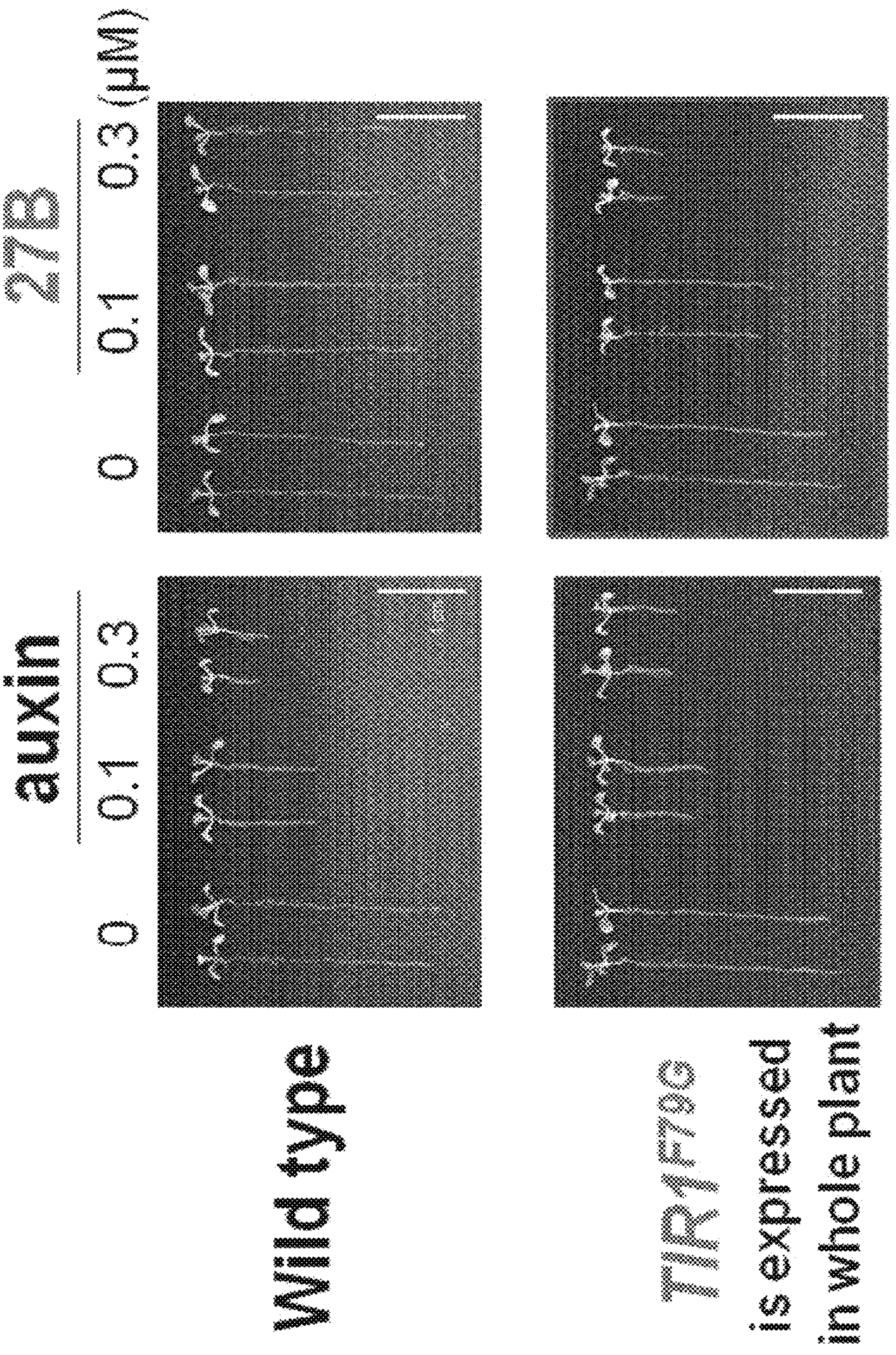
FIG. 1 This is diagram showing the results of root elongation assay in Test Example 2. On the left side of the photo, "$TIR1^{F79G}$" indicates experiments using *Arabidopsis* seeds having an expression cassette of a mutant auxin receptor (TIR1 F79G), whereas "Wild type" indicates a wild type *Arabidopsis* seeds without this expression cassette. On the upper side of the photo, "auxin" indicates experiments using auxin (indole-3-acetic acid) as the test compound, whereas "27B" indicates experiments using the auxin derivative synthesized in Example 25 as the test compound. The numbers below these words indicate the test compound concentration in the medium. The bar in each photo represents a 1 cm scale.

In this specification, the expressions "containing" and "contains" include concepts such as "containing", "contains", "consisting essentially of" and "consisting only of."

1. Auxin Derivative

As one aspect of the present invention, the General Formula (1):

[Chemical Formula 8]

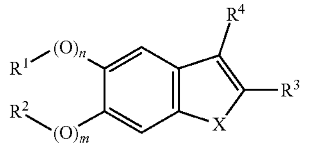
(1)

[wherein n and m are the same or different and represents 0 or 1. $R^1$ and $R^2$ are the same or different and each represents a hydrogen atom, an aryl group that may be substituted, or an alkyl group that may be substituted (except when $R^1$ and $R^2$ are both hydrogen atoms at the same time). One of $R^3$ and $R^4$ represents a carboxyalkyl group, and the other represents a hydrogen atom. X represents —NH— or —CH═CH—.] The present invention relates to the compound represented by, its agriculturally acceptable salt, hydrate or solvate. This will be described below.

n is preferably 0.

m is preferably 0.

The aryl group represented by $R^1$ or $R^2$ has no particular limitations, but preferably has 6 to 50 carbon atoms, more preferably 6 to 30 carbon atoms, then 6 to 20 carbon atoms, 6 to 12 carbon atoms, and an aryl group having 6 to 8 carbon atoms is particularly preferable. Specific examples of such an aryl group include phenyl group, naphthyl group, phenylalkyl group (e.g. benzyl groups and phenethyl groups etc.), biphenyl group, pentarenyl group, indenyl group, anthranyl group, tetracenyl group, pentacenyl group, pyrenyl group, perylenyl group, fluorenyl group and phenanthryl group, etc. Phenyl group, naphthyl group, phenylalkyl group and biphenyl group, etc. are preferred, and phenyl group, naphthyl group and phenylalkyl group are considered more preferable. Even more preferable is the phenyl group and the benzyl group, etc., and the phenyl group is more preferable than this.

The substituent that the aryl group represented by $R^1$ or $R^2$ may have is not particularly limited. Examples include an alkyl group that may be substituted, an alkoxy group that may be substituted, a halogen atom (F, Br, Cl, etc.), an aryl group that may be substituted, an aryloxy group that may be substituted, a hydroxyl group, a heteroatom-containing group, an alkenyl group that may be substituted, an alkynyl group, that may be substituted and a —COOR" group (wherein R" is a hydrogen atom or a hydrocarbon group) etc. Preferable substituents include an alkyl group that may be substituted, an alkoxy group that may be substituted, a halogen atom, an aryl group that may be substituted and an aryloxy group that may be substituted. More preferable among these is an alkyl group that may be substituted, an alkoxy group that may be substituted, and a halogen atom etc.

The alkyl group that may be substituted that the aryl group represented by $R^1$ or $R^2$ may have is not particularly limited. Examples include a linear chain, branched chain or a ring with 1 to 20 carbon atoms, which may be substituted with a halogen atom etc. (F, Br, Cl, I etc.). Preferably this group should have 1 to 12 carbons, more preferably 1 to 6 carbons, more preferably 1 to 3 carbons and even more preferably the alkyl chain shown in 1. The number of substituents is not particularly limited and is preferably 0 to 6, more preferably 0 to 3, and even more preferably 0. Examples of such an alkyl group that may be substituted include a methyl group, an ethyl group, an n-propyl group, an isopropyl group, an n-butyl group, an isobutyl group, a sec-butyl group, a t-butyl group, a perfluoromethyl group, a perfluoroethyl group and a cyclohexyl group, etc.

The alkoxy group that may be substituted that the aryl group represented by $R^1$ or $R^2$ may have is not particularly limited. Examples include a linear chain or a branched chain with 1 to 20 carbon atoms, which may be substituted with a halogen atom etc. (F, Br, Cl, I etc.). Preferably this group should have 1 to 12 carbons, more preferably 1 to 6 carbons, more preferably 1 to 3 carbons and even more preferably the alkoxy group shown in 1. The number of substituents is not particularly limited and is preferably 0 to 6, more preferably 0 to 3, and even more preferably 0. Examples of such an alkyl group that may be substituted include a methoxy group, an ethoxy group, an n-propoxy group, an isopropoxy group, an n-butoxy group, an isobutoxy group, a sec-butoxy group, a t-butoxy group, a perfluoromethoxy group and a perfluoroethoxy group, etc.

The halogen atom that the aryl group represented by $R^1$ or $R^2$ may have is preferably F or Cl etc.

The aryl group that may be substituted that the aryl group represented by $R^1$ or $R^2$ may have is not particularly limited. An example is an aryl group with 6 to 12 carbons that may be substituted with a halogen atom (F, Br, Cl, I etc.). Preferably the aryl group has 6 to 8 carbon atoms. The number of substituents is not particularly limited and is preferably 0 to 6, more preferably 0 to 3, and even more preferably 0. Examples of such an aryl group that may be substituted include a phenyl group, a naphthyl group, a benzyl group, and a phenethyl group.

The aryloxy group that may be substituted that the aryl group represented by $R^1$ or $R^2$ may have is not particularly limited. An example is an aryloxy group with 6 to 12 carbons that may be substituted with a halogen atom (F, Br, Cl, I etc.). Preferably the aryloxy group has 6 to 12 carbon atoms, and more preferably 6 to 8 carbon atoms. The number of substituents is not particularly limited, and is preferably 0-6, more preferably 0-3, and even more preferably 0. Examples of such an aryloxy group that may be substituted include a phenoxy group, a naphthoxy group, a benzyloxy group, and a phenethyloxy group.

The heteroatom-containing group that the aryl group represented by $R^1$ or $R^2$ may have can contain as heteroatom, at least one nitrogen atom (N), an oxygen atom (O), a sulfur atom (S), a boron atom (B), a phosphorus atom (P), a silicon atom (Si) etc. Preferably, the heteroatom-containing group is a linear chain, branched chain or a ring having at least one nitrogen atom (N), an oxygen atom (O) or a sulfur atom (S) etc. Specific examples of heteroatom groups include a cyano (—CN) group, a nitro (—$NO_2$) group, an amino group, etc.; as well as group obtained by eliminating one hydrogen atom from multi-element rings like a furan ring, a thiophene ring, a pyrrole ring, a silole ring, a borol ring, a phosphole ring, an oxazole ring, a thiazole ring, a pyridine ring, a pyridazine ring, a pyrimidine ring or a pyrazine ring. It is also possible to use a group obtained by eliminating one hydrogen atom from the aforementioned multi-element rings or from a fused ring between these and a benzene ring etc. (thienothiophene ring, quinoline ring, etc.)

The alkenyl group that may be substituted that the aryl group represented by $R^1$ or $R^2$ may have is not particularly limited. Examples include linear chains, branched-chains or rings with 2 to 20 carbons that may be substituted with a halogen atom (F, Br, Cl, I etc.). Preferably, the alkenyl group would have 2 to 12 carbon atoms, more preferably 2 to 6 carbon atoms, and even more preferably 2 to 3 carbon atoms. The number of substituents is not particularly limited and is preferably 0 to 6, more preferably 0 to 3, and even more preferably 0. Examples of such an alkenyl group that may be substituted include a vinyl group, an allyl group, a 1-propenyl group, an isopropenyl group, a butenyl group, a pentenyl group, and a hexenyl group etc.

The aryl group that may be substituted that the aryl group represented by $R^1$ or $R^2$ may have is not particularly limited. Examples include linear chains, branched-chains or rings with 2 to 20 carbons that may be substituted with a halogen atom (F, Br, Cl, I etc.). Preferably, the alkenyl group would have 2 to 12 carbon atoms, more preferably 2 to 6 carbon atoms, and even more preferably 2 to 3 carbon atoms. The number of substituents is not particularly limited and is preferably 0 to 6, more preferably 0 to 3, and even more preferably 0. Examples of such an alkynyl group that may be substituted include an ethynyl group, a propynyl group, a butynyl group, a pentynyl group, a hexynyl group, and a phenylacetinyl group etc.

The R" in the —COOR" that the aryl group represented by $R^1$ or $R^2$ may have is a hydrogen atom or a hydrocarbon group, preferably a hydrogen atom or an alkyl group described above. Specific examples of —COOR" include a —COOH, a —$COOCH_3$, a —$COOC_2H_5$, a —$COOC_3H_7$, a —$COOC(CH_3)_2$, a —$COOC_4H_9$, a —$COOCH(CH_3)\ C_2H_5$, a —$COOCH_2CH(CH_3)_2$ and a —$COOC(CH_3)_3$ etc.

The number of substituents that the aryl group represented by $R^1$ or $R^2$ may have is not particularly limited. For example, the aryl group may have 0 to 6 groups, preferably 1 to 3 groups, and more preferably 1 to 2 groups. In a preferred embodiment of the present invention, when the substituent that the aryl group represented by $R^1$ or $R^2$ may have is at least one selected from the group consisting of an alkyl group and a halogen atom, the preferred number of substituents is two, whereas when the substituent is an alkoxy group, the preferred number of substituents is one.

When the aryl group represented by $R^1$ or $R^2$ may have two or more substituents, the two substituents situated adjacent to one another may combine to form a ring. To form a ring means, for example, when the aryl group is a phenyl group, the group represented by General Formula (1):

[Chemical Formula 9]

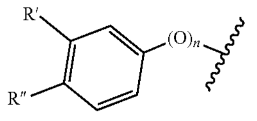

[wherein R' and R" indicate groups that the aryl group represented by $R^1$ may have, and n is as defined above.] is the group represented by the formula:

[Chemical Formula 10]

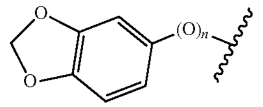

[wherein n is as defined above.]

adamantyl group represented by $R^1$ or $R^2$ is not particularly limited, for example, 1-adamantyl group, and a 2-adamantyl group. Among these, an 1-adamantyl group is preferable.

The substituents that the adamantyl group represented by $R^1$ or $R^2$ may have are the same as those that the aryl group represented by $R^1$ or $R^2$ may have.

The number of substituents that the adamantyl group represented by $R^1$ or $R^2$ may have is not particularly limited. For example, the adamantyl group may have 0-6 groups, preferably 0-3 groups, and more preferably 0 groups.

The alkyl group represented by $R^1$ or $R^2$ is not particularly limited. Examples include linear chain, branched chain or rings (preferably rings) having 1 to 20 carbon atoms. Preferably the alkyl group has 3 to 20 carbon atoms, more preferably 4 to 15 carbon atoms and even more preferably 6 to 12 atoms. Specific examples of such an alkyl group include a methyl group, an ethyl group, an n-propyl group, an isopropyl group, an n-butyl group, an isobutyl group, a sec-butyl group, a t-butyl group, and a cyclohexyl group.

The substituents that the alkyl group represented by $R^1$ or $R^2$ may have are the same as those that the aryl group represented by $R^1$ or $R^2$ may have.

The number of substituents that the alkyl group represented by $R^1$ or $R^2$ may have is not particularly limited. For example, the alkyl group may have 0-6 groups, preferably 0-3 groups, and more preferably 0 groups. The heterocyclic group represented by $R^1$ or $R^2$ is not particularly limited. Examples include groups obtained by eliminating one hydrogen atom from multi-element rings like a furan ring, a thiophene ring, a pyrrole ring, a silole ring, a borol ring, a phosphole ring, an oxazole ring, a thiazole ring, a pyridine ring, a pyridazine ring, a pyrimidine ring or a pyrazine ring etc. It is also possible to use a group obtained by eliminating one hydrogen atom from the aforementioned multi-element rings or from a fused ring between these and a benzene ring etc. (benzothiophene ring, thienothiophene ring, quinoline ring, etc.)

The substituents that the heterocyclic group represented by $R^1$ or $R^2$ may have are the same as those that the aryl group represented by $R^1$ or $R^2$ may have.

The number of substituents that the heterocyclic group represented by $R^1$ or $R^2$ may have is not particularly limited. For example, the heterocyclic group may have 0-6 groups, preferably 0-3 groups, and more preferably 0 groups.

It is preferable for one of $R^1$-$(O)_n$— and $R^2$-$(O)_m$— to be a hydrogen atom. It is more preferable for $R^2$-$(O)_m$ to be a hydrogen atom.

Aside from hydrogen atoms, specifically, $R^1$-$(O)_n$— and $R^2$-$(O)_m$— is preferably:
[Chemical Formula 11]
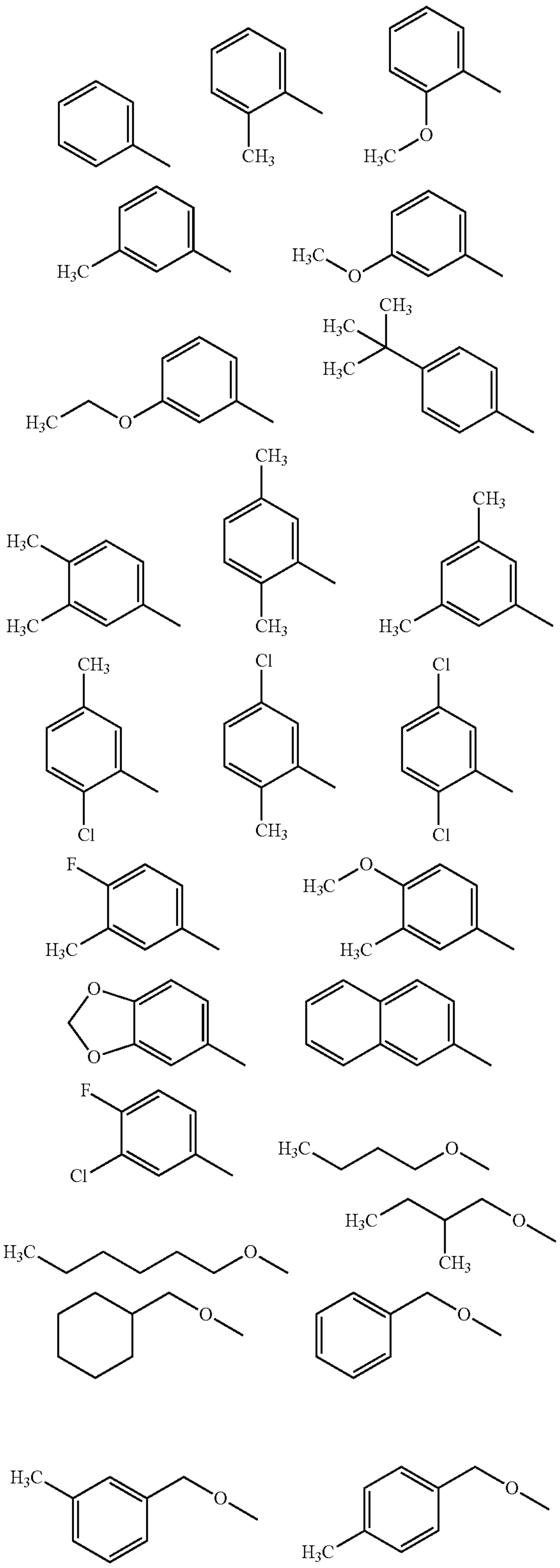
[Chemical Formula 12]
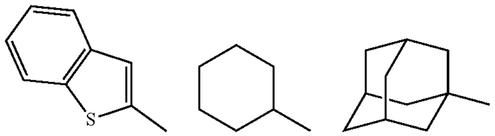
[Chemical Formula 13]
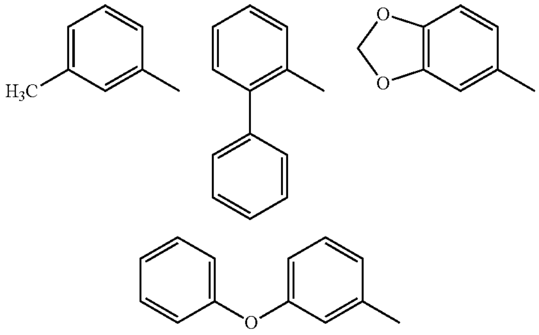
等が挙げられ、より好ましくは
etc., and more preferably
[Chemical Formula 14]
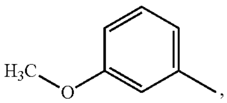
,
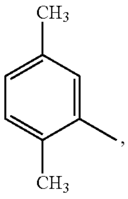
,
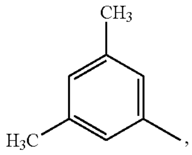
,
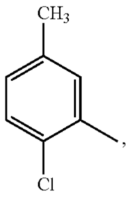
,
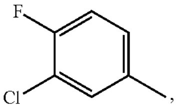
,
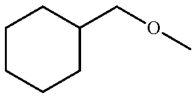
,
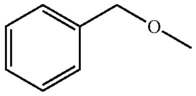
,
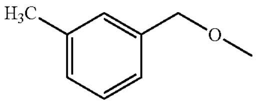
,
又は
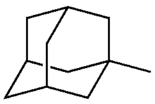
etc.

Furthermore, aside from hydrogen atoms, $R^1$-$(O)_n$— is preferably:

[Chemical Formula 15]

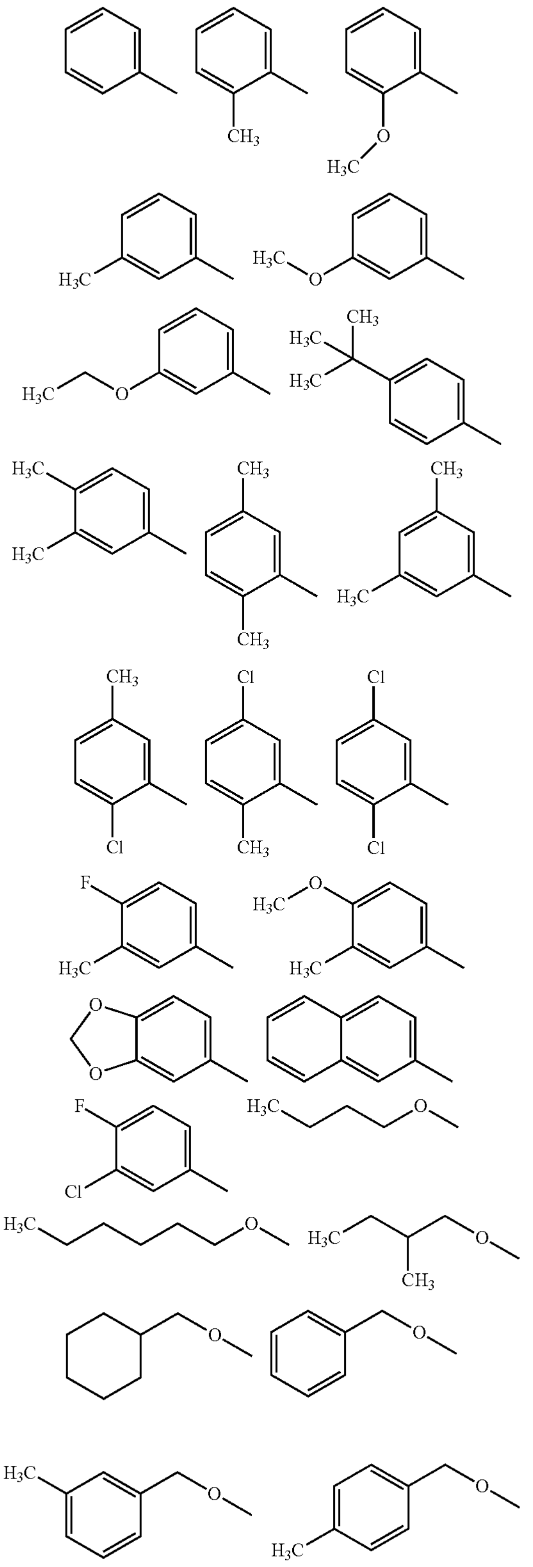

[Chemical Formula 16]

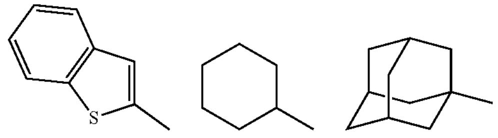

etc., and $R^2$-$(O)_m$— is preferably:

[Chemical Formula 17]

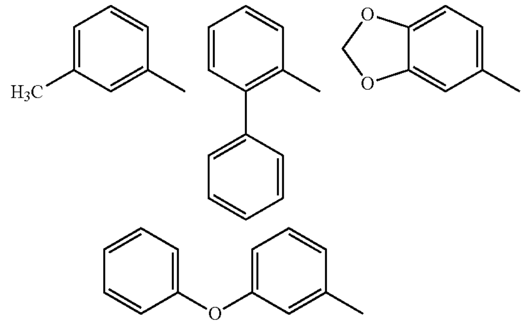

and etc.

One of $R^3$ and $R^4$ is a carboxyalkyl group, and the other is a hydrogen atom. In the preferred embodiment, $R^3$ is a hydrogen atom and $R^4$ is a carboxyalkyl group. The aforementioned alkyl groups are examples of the alkyl group in the carboxyalkyl group. In other words, these include a carboxymethyl group ($-CH_2COOH$), a carboxyethyl group ($-C_2H_4COOH$), a carboxypropyl group ($-C_3H_6COOH$), a carboxybutyl group ($-C_4H_8COOH$), a carboxypentyl group ($-C_5H_{10}COOH$) and a carboxyhexyl group ($-C_6H_{12}COOH$) etc.

X is preferably —NH—.

In one embodiment of the present invention, the compounds represented by the General Formula (1) are preferably the compounds represented by General Formula (1A):

[Chemical Formula 18]

(1A)

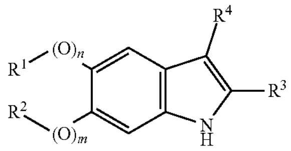

[wherein n, m, $R^1$, $R^2$, $R^3$, and $R^4$ are as defined above.]

Preferably, they are compounds represented by General Formula (1A1):

[Chemical Formula 19]

(1A1)

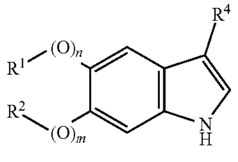

[wherein n, m, $R^1$, $R^2$, and $R^3$ are as defined above. $R^4$ is a carboxyalkyl group.], and more preferably compounds represented by the General Formula (1A1a):

[Chemical Formula 20]

(1A1a)

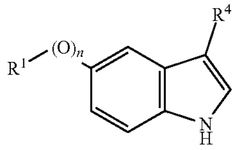

[wherein n and $R^1$ are as defined above. $R^4$ is a carboxyalkyl group.]

In another embodiment of present invention, the compound represented by the General Formula (1) is preferably the following embodiment: $R^2$-$(O)_m$ is a hydrogen atom, and when n is 0, $R^4$ is:

(a) An adamantyl group which may be substituted, (b) An aryl group which may be substituted by at least one substituent selected from the group consisting of an aryl group and an aryloxy group, or by an alkyl group, alkoxy group, or a halogen atom, as well as at least one substituent selected from the group consisting of an alkyl group, an alkoxy group, a halogen atom, and an aryl group, OR (c) An alkyl group with 5 to 20 carbon atoms which may be substituted by at least one substituent selected from the group consisting of an alkyl group, an alkoxy group, a halogen atom, an aryl group, and an aryloxy group; OR when n is 1, $R^4$ is:

(d) An adamantyl group that may be substituted, (e) A phenyl group that may be substituted by fewer than two substituents, a naphthyl group that may be substituted, or a benzyl group substituted with at least one substituent selected from the group consisting of an alkyl group, a halogen atom, an aryl group and an aryloxy group, OR (f) An alkyl group having 6 to 20 carbon atoms that is substituted with at least one substituent selected from the group consisting of a cycloalkyl group, an alkoxy group, a halogen atom, an aryl group, and an aryloxy group; OR $R^1$-$(O)_n$— is a hydrogen atom and when m is 0, $R^2$ is:

(g) An adamantyl group that may be substituted (h) (h1) An aryl group substituted by at least one substituent selected from the group consisting of an alkoxy group, an aryl group and an aryloxy group, OR (h2) An aryl group which may be substituted by two or more substituents comprising an alkyl group or a halogen atom, and at least one substituent selected from the group consisting of an alkyl group, an alkoxy group, a halogen atom, an aryl group, and an aryloxy group, OR (i) An alkyl group having 4 to 20 carbon atoms that may be substituted; OR when m is 1, $R^2$ is:

(j) An adamantyl group that may be substituted;

(k) A phenyl group or a naphthyl group which may be substituted by at least one substituent selected from the group consisting of an alkyl group, an alkoxy group, a halogen, an aryl group and an aryloxy group, OR (1) An alkyl group having 4 to 20 carbon atoms that may be substituted.

There is no particular limitation to the salts of the compound represented by the General Formula (1), as long as it is an agriculturally acceptable salt. Either an acidic salt or a basic salt can be used as the salt. Examples of acidic salts include inorganic acid salts such as hydrochloride, hydrobromide, sulfate, nitrate, phosphate; organic salts such as acetate, propionate, tartrate, fumarate, maleate, malate, citrate, methanesulfonate and paratoluenesulfonate etc. Examples of basic salts include alkali metal salts such as sodium salts and potassium salts; as well as alkaline earth metals such as calcium salts and magnesium salts; ammonia salts; and salts with organic amines etc. such as morpholine, piperidine, pyrrolidine, monoalkylamine, dialkylamine, trialkylamine, mono (hydroxyalkyl) amine, di (hydroxyalkyl) amine and tri (hydroxyalkyl). Among these, it is preferable to use basic salts. Specifically, the terminal carboxy group in the compound represented by General Formula (1) can form a salt with an agriculturally acceptable basic compound.

The compound represented by the General Formula (1) can be hydrates and solvates. Examples of the solvents include agriculturally acceptable organic solvents (such as ethanol, glycerol, acetic acid etc.)

2. Manufacturing Method

The compound represented by General Formula (1) can be synthesized in a variety of ways. For example, a compound in which $R^1$-(O)— is a group other than a hydrogen atom and a hydroxyl group can be synthesized by methods that include Step (I) or (II) below:

[Chemical Formula 21]

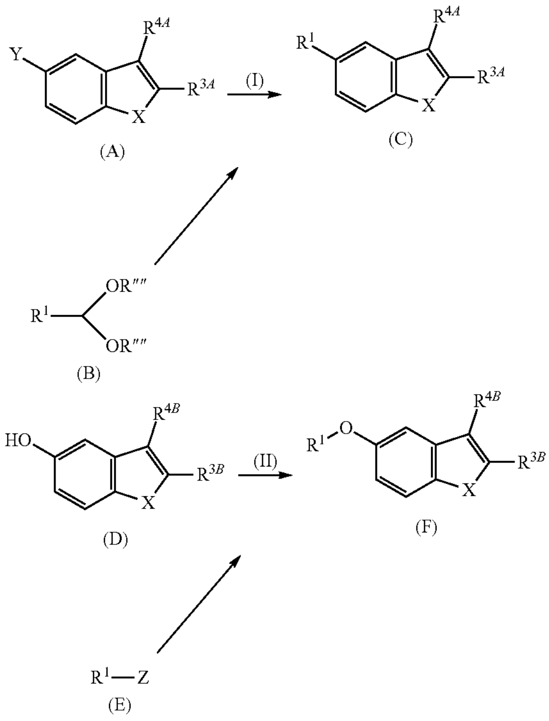

[wherein X and $R^1$ are as defined above. Y represents a halogen atom. One of $R^{3A}$ and $R^{4A}$ represents a carboxyalkyl group or an alkyl ester of a carboxyalkyl group, and the other represents a hydrogen atom. Two R"" may be the same or different and each may be a hydrogen atom or an alkyl group; the two R"" may be bonded to each other to form a ring with adjacent —O—B—O—, and this ring may be further condensed with an aromatic ring (particularly a benzene ring or a naphthalene ring, etc.). One of $R^{3B}$ and $R^{4B}$ represents an alkyl ester of a carboxyalkyl group, and the other represents a hydrogen atom.]. A compound in which $R^{2-}(O)_m$— is a group other than a hydrogen atom or a hydroxyl group, and a compound in which $R^{1-}(O)_n$— and $R^{2-}(O)_m$— are groups other than hydrogen atoms or hydroxyl groups can both be synthesized by following a method that includes these steps.

(2-1) Step I

In this step, a compound represented by the General Formula (A) is reacted with a compound represented by General Formula (B) in the presence of a palladium catalyst and a base, if needed, to provide a compound represented by General Formula (C).

Examples of compounds represented by General Formula (B) include:

[Chemical Formula 22]

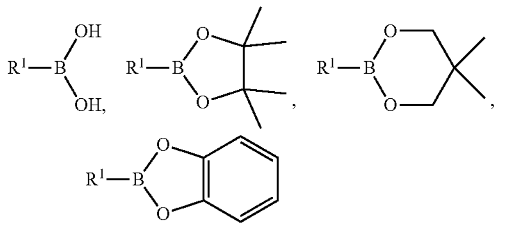

[wherein $R^1$ is as defined above.]

In view of the yield, the amount of compound represented by the General Formula (B) used relative to one mole of compound represented by General Formula (A) is preferably 0.1 to 10 moles, more preferably 0.3 to 4 moles and even more preferably 0.8 to 3 moles.

Examples of the palladium-based catalyst include metallic palladium and palladium compounds known to be catalysts for synthesis of organic compounds (including polymers) etc. Specific examples include $Pd(PPh_3)_4$ (Ph is a phenyl group), palladium carbon, $PdCl_2(PPh_3)_2$ (Ph is a phenyl group), $Pd(OAc)_2$ (Ac is an acetyl group), Tris (dibenzylideneacetone)dipalladium(O) ($Pd_2(dba)_3$), tris (dibenzylideneacetone)dipalladium(O) chloroform complex, bis(dibenzylideneacetone)palladium(O), bis(tri-t-butylphosphino)palladium(O), (1,1'-bis(diphenylphosphino) ferrocene)dichloropalladium (II) etc. In this step, it is preferable to use $Pd(PPh_3)_4$ etc.

In view of the yield, the amount of palladium catalyst used relative to one mole of compound represented by General Formula (A) is preferably 0.001 to 1 mole, more preferably 0.005 to 0.1 mole and even more preferably 0.01 to 0.07 mole.

Examples of bases include ammonium chloride, potassium fluoride, cesium fluoride, sodium hydroxide, potassium hydroxide, sodium methoxide, sodium hydrogen carbonate, potassium hydrogen carbonate, sodium carbonate, potassium carbonate, cesium carbonate, potassium phosphate, sodium acetate, potassium acetate and calcium acetate etc. In this step it is preferable to use sodium carbonate.

Though dependent on the manufacturing conditions etc., the amount of base used relative to one mole of compound represented by General Formula (A) is preferably 0.01 to 10 moles, more preferably 0.5 to 7 moles, and even more preferably 1 to 4 moles.

The above reaction is usually carried out in the presence of a reaction solvent. Although there is no particular limitation to the reaction solvent used, it is preferable to use aromatic hydrocarbons and alcohols etc., and more preferable to use toluene, methanol and ethanol etc.

In this step, it is possible to use appropriate additives in addition to the above ingredients, as long as they do not impair the effects of the present invention.

Generally, inert gas atmosphere (argon gas, nitrogen gas atmosphere etc.) is used as the reaction atmosphere. The reaction temperature can be any of heating, room temperature or cooling, and it is usually preferable to perform the reaction between 0 to 150° C. (particularly between 60 to 120° C.). There is no particular limitation with the reaction time, and it may usually be 3 to 48 hours, particularly 6 to 24 hours.

After completion of the reaction, purification can be performed according to conventional method(s), as needed. It is also possible to proceed to the next step without purifying the products.

(2-2) Step II

In this step, a compound represented by the General Formula (D) is reacted with a compound represented by General Formula (E) in the presence of a base to provide a compound represented by General Formula (F).

In view of the yield, the amount of compound represented by General Formula (E) used relative to one mole of compound represented by General Formula (D) is preferably 0.1 to 10 moles, more preferably 0.2 to 5 moles and even more preferably 0.5 to 2 moles.

Examples of bases include ammonium chloride, potassium fluoride, cesium fluoride, sodium hydroxide, potassium hydroxide, sodium methoxide, sodium hydrogen carbonate, potassium hydrogen carbonate, sodium carbonate, potassium carbonate, cesium carbonate, potassium phosphate, sodium acetate, potassium acetate and calcium acetate etc. In this step, it is preferable to use cesium carbonate.

In view of the yield, the amount of base used relative to one mole of compound represented by General Formula (D) is preferably 0.05 to 8 moles, more preferably 0.1 to 4 moles and even more preferably 0.2 to 2 moles.

The above reaction is usually carried out in the presence of a reaction solvent. Although there is no particular limitation to the reaction solvent used, it is preferable to use N, N-dimethylformamide etc.

In this step, it is possible to use appropriate additives in addition to the above ingredients, as long as they do not impair the effects of the present invention.

Generally, inert gas atmosphere (argon gas, nitrogen gas atmosphere etc.) is used as the reaction atmosphere. The reaction temperature can be any of heating, room temperature or cooling, and it is usually preferable to perform the reaction between 0 to 100° C. (particularly between 30 to 70° C.). There is no particular limitation with the reaction time, and it may usually be 4 to 48 hours, particularly 8 to 24 hours.

After completion of the reaction, purification can be performed according to conventional method(s), as needed. It is also possible to proceed to the next step without purifying the products.

(2-3) Step III

When one of $R^{3A}$ or $R^{4A}$ in Reaction Scheme (I) is an alkyl ester of carboxyalkyl groups, and in the case of Reaction Scheme (II), the alkyl ester of the compound(s) represented by General Formula (C) or (F) can be reduced using a base (Step III) to provide a compound represented by General Formula (1).

Examples of bases include ammonium chloride, potassium fluoride, cesium fluoride, sodium hydroxide, potassium hydroxide, lithium hydroxide, sodium methoxide, sodium hydrogen carbonate, potassium hydrogen carbonate, sodium carbonate, potassium carbonate, cesium carbonate, potassium phosphate, sodium acetate, potassium acetate, and calcium acetate. In this step, it is preferable to use potassium hydroxide or lithium hydroxide.

Though dependent on the manufacturing conditions etc., the amount of base used relative to one mole of raw material is preferably 0.01 to 10 moles, more preferably 0.5 to 7 moles, and even more preferably 1 to 5 moles.

The above reaction is usually carried out in the presence of a reaction solvent. Although there is no particular limitation to the reaction solvent used, it is preferable to use tetrahydrofuran, alcohols (particularly methanol) or water.

In this step, it is possible to use appropriate additives in addition to the above ingredients, as long as they do not impair the effects of the present invention.

Generally, inert gas atmosphere (argon gas, nitrogen gas atmosphere etc.) is used as the reaction atmosphere. The reaction temperature can be any of heating, room temperature or cooling, and it is usually preferable to perform the reaction between 0 to 100° C. (particularly between 10 to 40° C.). There is no particular limitation with the reaction time, and it may usually be 1 to 24 hours, particularly 2 to 12 hours.

After completion of the reaction, purification can be performed according to conventional method(s), as needed. It is also possible to proceed to the next step without purifying the products.

3. Use

At least one compound selected from the group consisting of a compound represented by the General Formula (1), its agriculturally acceptable salt, a hydrate, or a solvate (may be shown as "Active ingredient of the present invention" in the present specification) has reduced binding to the wild-type (endogenous) auxin receptor and has good binding to reduced auxin-sensitivity auxin receptor. Therefore, such a compound can be used as an active ingredient of a growth regulator plants (may be shown as "Plant growth regulator of the present invention") that express the reduced auxin-sensitivity auxin receptor.

The reduced auxin-sensitivity auxin receptor results from adding a mutation to the amino acid sequence of the wild-type auxin receptor, and has no particular limitation as long as its binding affinity to endogenous auxin (for example, indole-3-acetic acid) is lower than that of the wild-type auxin receptor (for example, the binding affinity is reduced to less than 1/10, less than 1/50, less than 1/100, less than 1/200, less than 1/400 and less than 1/800).

Various plants have the wild-type auxin receptor, which is known as TIR1. Its amino acid sequence in *Arabidopsis thaliana* is known to be the sequence shown in SEQ ID NO: 1. The amino acid sequences of TIR1 in other plant species are also known, and these sequences can be obtained from databases such as NCBI.

The mutation which reduces the auxin sensitivity of the receptor can be designed based on known information. For example, previously published literature (Nature, Vol 446, 5 Apr. 2007, pp 640-645) analyzed the interaction region between auxin (indole-3-acetic acid) and its receptor (TIR1). Here, it was reported that the phenylalanine residue in Loop 2 of TIR1 (for example, according to SEQ ID NO: 1, this refers to amino acid residue 79 and 82 (phenylalanine) of the N-terminus) interacts with the benzene ring of the auxin indole ring. This means that replacing the amino acid residue in the auxin receptor (preferably the phenylalanine residue in Loop 2 of TIR1 (in SEQ ID NO: 1, amino acid residue 79 and/or 82 (phenylalanine) from N-terminus, OR the amino acid residue corresponding to amino acid residue 79 and/or 82 from the N-terminus of an ortholog or paralog of TIR1 in SEQ NO: 1) that interacts with the benzene ring of the auxin indole ring with another amino acid residue can reduce the auxin sensitivity of the receptor.

The "other amino acid residue," which is the amino acid residue after replacement, is preferably an amino acid residue for which the molecular weight of the side chain is smaller than that of the side chain molecular weight of phenylalanine residue. Examples of such amino acid residues include hydrophobic amino acid residues such as glycine, alanine, valine, isoleucine, leucine, methionine and cysteine; as well as serine residue. Preferable residues are glycine, alanine, valine, isoleucine and serine, etc. Of these, more preferable are glycine, alanine and serine, and even more preferably alanine and serine, and still more preferably alanine.

There is no particular limitation to plants expressing the reduced auxin-sensitivity auxin receptor, as long as all or some cells or tissue (preferably some cells or tissue) express the reduced auxin-sensitivity auxin receptor. By using a plant that expresses the receptor only in some cells or tissues, it is possible to efficiently produce the intended effect of based on the auxin response signal, while reducing any of its unintended effects. In order to express this receptor in some cells or tissues, it is possible to target the roots, xylem pole pericycle cells, stems, apical meristems, branches, leaves, stoma, flower buds, flowers and primordia of each organ, etc.

Plants expressing the reduced auxin-sensitivity auxin receptors can be obtained using known methods. Such plants can be obtained by introducing a polynucleotide containing a coding sequence of a promoter and the reduced auxin-sensitivity auxin receptor that is under its control to a plant. Although there are no particular limitations to the promoter that can be used, if the goal is to express the receptor only in some cells or tissues, it would be beneficial to use a promoter that is specific to various tissues and cells.

In *Arabidopsis thaliana*, examples of tissue or cell-specific promoters include the At5g6639 gene promoter that is specific to the roots, the AT1G62360 gene promoter that is specific to the apical meristem and AT1G08810 gene promoter specific to the stoma.

The method of introducing the polynucleotide is not particularly limited. It can be selected to suit the target of introduction. Examples of the introduction method include *Agrobacterium* methods such as the leaf disk method, floral dip method and floral spray method, particle gun method, virus-mediated nucleic acid delivery and electroporation method etc. Among these, the *Agrobacterium* method is preferable from the viewpoint of convenience and safety.

There are no particular limitations to the species of the target plant for the plant growth regulator in the present invention. For example, it can be widely applied to plants such as angiosperms (dicotyledonous plants, monocotyledonous plants, etc.), gymnosperms, moss plants, and fern plants. Specific examples include Solanaceae such as tomatoes, peppers, chili peppers and eggplants, Cucurbitaceae such as cucumbers, pumpkins, melons and watermelons, stem vegetables such as cabbage, broccoli and Chinese cabbage, condiment vegetables such as celery, parsley and lettuce, *Allium* such as leek, onion and garlic, beans such as soybeans, peanuts, green beans, peas and azuki beans, other fruit vegetables such as strawberries, straight roots such as radish, turnip, carrot, and burdock, tubers such as taro, cassava, potato, sweet potato and Chinese yam, soft vegetables such as asparagus, spinach and mitsuba parsley, flowering plants such as *eustoma*, stock, carnation and *chrysanthemum*, cereals such as rice and corn, turf such as bentgrass and lawngrass, oil crops such as rapeseed and peanuts, sugar crops such as sugar cane and sugar beet, textile crops such as cotton and rush, feed crops such as clover, sorghum and dent corn, deciduous fruit trees such as apples, pears, grapes and peaches, citrus fruits such as mandarin, lemon and grapefruit, and wood like satsuki, azalea and cedar etc.

There is no particular limitation to the target organ of the plant growth regulator of the present invention, as long as it is an organ constituting the plant. The target organ is preferably a stem, bud, root, ovary, and fruit, more preferably a stem, bud, and root, and still more preferably a stem.

The plant growth regulator of the present invention may be comprised only of the active ingredient of the present invention, but various additives can be added in addition to this, according to the dosage form and mode of application. There is no particular limitation to the content ratio of the active ingredient of the present invention in the plant growth regulator. Specifically, it is exemplified by contents of 0.0001 to 100% by weight, preferably around 0.01 to 50% by weight.

There is no particular limitation with the dosage form of the plant growth regulator of the present invention, as long as it is an agriculturally acceptable dosage form. Examples include liquid agents, solid agents, powder agents, fine granules, granules, wettable powder, flowable agent, emulsion, paste agent and dispersant etc.

There is no particular limitation to the additives used, as long as it is an agriculturally acceptable additive. Examples include carriers, surfactants, thickeners, extenders, binders, vitamins, antioxidants, pH adjusters, volatilization inhibitors and dyes.

There is no particular limitation to the mode of application of the plant growth regulator of the present invention, as long as it is a known form of use of pesticides (or an application to be developed in the future). Examples thereof include spraying, dripping, coating, mixing and dissolution in a plant growth environment (in soil, water, solid medium, liquid medium, etc.).

Embodiment

Hereinafter, the present invention will be described in detail with reference to examples, but the present invention should not be construed as being limited thereto.

Unless otherwise specified, all reactants and reagents including dry solvents used were commercially available products. Unless otherwise restricted, all reactions were performed in air with reagent grade solvents. All work-up and purification procedures were performed in air with reagent grade solvents. Analytical thin layer chromatography (TLC) was performed using E. Merck silica gel 60 $F_{254}$ pre-coated plates (0.25 mm). The developed chromatogram was analyzed with a UV lamp (254 nm). Flash column chromatography was performed using a Biotage Isolera® instrument equipped with a KANTO silica gel 60N (0.04-0.1 mm) or Biotage SNAP Ultra 10 g cartridge. Preparative thin layer chromatography (PTLC) was performed using a Wakogel® B5-F silica-coated plate (0.75 mm) prepared in advance. Reverse phase column chromatography was performed using a Biotage Isolera® instrument equipped with a KP-C18-HS 12 g cartridge. LC/MS analysis was performed using Agilent Technologies 1200 series. High resolution mass spectra (HRMS) were obtained by Thermo Fisher Scientific Exactive. Microwave synthesis was performed using Biotage® Inintiator+. Nuclear magnetic resonance (NMR) spectra were recorded using a JEOL JNM-ECA-400 spectrometer ($^1$H 400 MHz, $^{13}$C 100 MHz), a JEOL JNM-ECA-50011 spectrometer ($^1$H 500 MHz, $^{13}$C 125 MHz), and a JEOL JMN-ECA-600II spectrometer equipped with an Ultra COOL probe ($^1$H 600 MHz, 13C 150 MHz). $^1$H NMR chemical shifts were expressed as relative parts per million of tetramethylsilane (δ0.00 ppm), the residual peak of $CD_3OD$ (δ3.30 ppm) and the residual peak of DMSO-$d_6$ (δ3.30 ppm) (ppm). $^{13}$C NMR chemical shifts were expressed as relative parts per million (ppm) of $CD_3OD$ (δ49.0 ppm), $CDCl_3$ (δ77.0 ppm), or DMSO-$d_6$ (δ39.5 ppm). Data are reported in the order of chemical shift, multiplicity (s=singlet, d=doublet, dd=doublet of doublets, t=triplet, m=multiplet, br=broad signal), coupling constant (Hz) and integration.

Synthesis Example 1: 2-(5-Bromo-1H-indol-3-yl)-2-oxoacetic acid

[Chemical Formula 23]

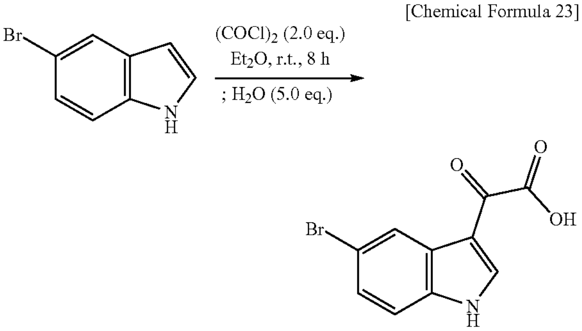

5-Bromoindole (5.0 g, 25.5 mmol) was dissolved in diethyl ether (100 mL) and the resulting solution was cooled to 0° C. Oxalyl chloride (2.2 mL, 1.0 equiv.) was added dropwise to the flask, and the resulting reaction mixture was returned to room temperature. After the mixture was stirred at room temperature for 2.5 hours, the reaction was quenched with water (2.3 mL, 5.0 equiv.). The reaction mixture was filtered to give 2-(5-Bromo-1H-indol-3-yl)-2-oxoacetic acid as a yellow powder (6.8 g, quant.).

$^1$H NMR (400 MHz, DMSO-$d_6$) δ 12.48 (s, 1H), 8.48 (d, J=3.1 Hz, 1H), 8.29 (d, J=1.8 Hz, 1H), 7.52 (d, J=8.6 Hz, 1H), 7.43 (dd, J=8.9, 2.1 Hz, 1H).

Synthesis Example 2: 2-(5-Bromo-1H-indol-3-yl)acetic acid

[Chemical Formula 24]

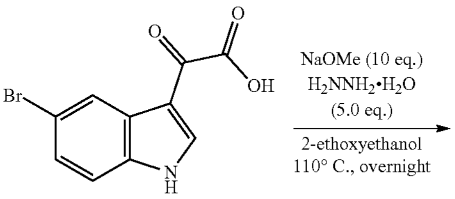

-continued

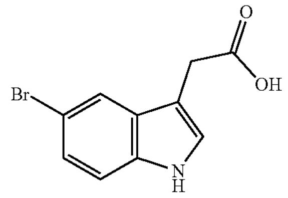

2-(5-Bromo-1H-Indol-3-yl)-2-oxoacetic acid (1.6 g, 7.0 mmol) was dissolved in 2-ethoxyethanol (31 mL), and hydrazine monohydrate (5 mL, 5 equiv.) was added to the flask. After the reaction mixture was stirred at 60° C. for 40 minutes, NaOMe (3.7 g, 10 equiv.) was added to the flask and stirred at 150° C. for an additional 7 hours. The reaction was quenched by the addition of water and the aqueous layer was washed 3 times with ethyl acetate. The aqueous layer was acidified with 6 M aqueous hydrochloric acid, and the resulting precipitate was extracted with dichloromethane. The combined organic layers were dried over $Na_2SO_4$, filtered and concentrated under vacuum. The resulting residue was purified by reverse phase column chromatography (MeOH/MeCN) and reprecipitated ($CHCl_3$/hexane) to give 2-(5-Bromo-1H-indol-3-yl)acetic acid as a pale yellow powder (1.2 g, 72%).

$^1H$ NMR (400 MHz, $CDCl_3$) δ 7.68 (d, J=1.8 Hz, 1H), 7.26 (d, J=8.6 Hz, 1H), 7.18 (dd, J=8.9, 1.5 Hz, 2H), 3.69 (s, 2H).

Synthetic Procedure A

[Chemical Formula 25]

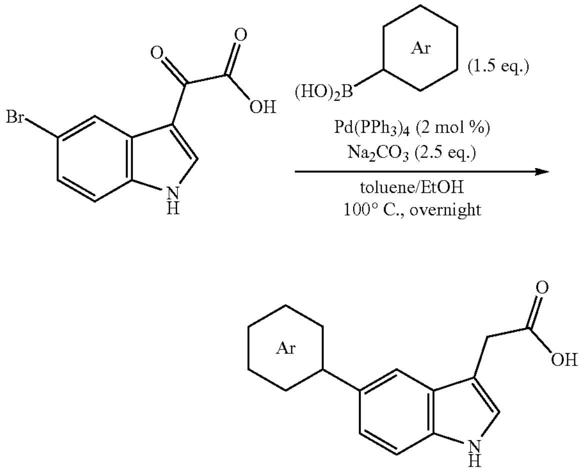

To a screw tube were added 5-bromo IAA (50.8 mg, 0.2 mmol), boronic acid (1.5 equiv.), Tetrakis(triphenylphosphine)palladium (4.6 mg, 2 mol %), sodium carbonate (42 mg, 2.0 equiv.), toluene (1 mL), ethanol (1 mL), and water (0.5 mL). The tube was filled with nitrogen gas and the reaction mixture was stirred at 100° C. overnight. The mixture was acidified with 6M aqueous hydrochloric acid, extracted with diethyl ether, dried over $Mg_2SO_4$ and concentrated under reduced pressure. The crude product was purified by reverse phase column chromatography (MeOH/MeCN), flash column chromatography or PTLC.

Synthetic Procedure B

[Chemical Formula 26]

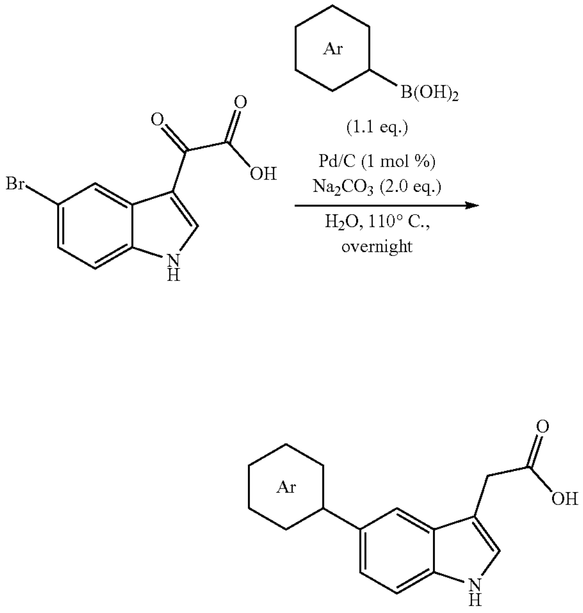

To a screw tube were added 5-bromo IAA (50.8 mg, 0.2 mmol), boronic acid (1.1 equiv.), 10% Palladium on carbon (2.3 mg, 1 mol %), sodium carbonate (42 mg, 2.0 equiv.) and water. The tube was filled with nitrogen gas and water (2 mL) was added to the mixture. The reaction mixture was stirred at 110° C. overnight. The mixture was diluted with water and filtered through Celite®. The mixture was washed with ethyl acetate and the mixture was acidified with 6 M aqueous hydrochloric acid. The resulting precipitate was extracted with diethyl ether and the organic layer was dried over $Na_2SO_4$, filtered and concentrated under vacuum. The resulting residue was purified by reverse phase column chromatography (MeOH/MeCN) or flash column chromatography.

Example 1: 2-(5-(o-tolyl)-1H-indol-3-yl)acetic acid (MK-189

[Chemcial Formula 27]

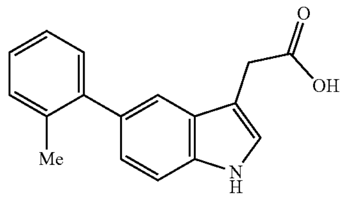

Synthesized according to Synthetic Procedure A and purified by PTLC ($CHCl_3$). Yield: 4.7 mg, 8.8%, white solid.

$^1H$ NMR (400 MHz, $CD_3OD$) δ 7.77 (s, 1H), 7.46 (s, 1H), 7.42 (d, J=6.1 Hz, 1H), 7.39 (s, 1H), 7.37 (dd, J=8.3, 1.5 Hz, 1H), 7.28 (t, J=7.6 Hz, 1H), 7.20 (s, 1H), 7.08 (d, J=7.3 Hz, 1H), 3.77 (s, 2H), 2.40 (s, 3H).

Example 2: 2-(5-(m-tolyl)-1H-indol-3-yl)acetic acid (MK-190

[Chemical Formula 28]

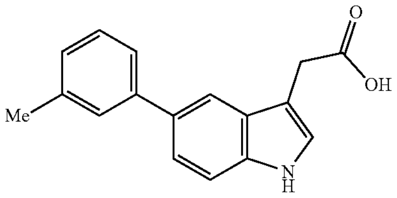

Synthesized according to Synthetic Procedure A and purified by PTLC ($CHCl_3$). Yield: 4.2 mg, 8%, white solid.

$^1$H NMR (600 MHz, $CD_3OD$) δ 7.47 (s, 1H), 7.37 (d, J=8.2 Hz, 1H), 7.24-7.17 (m, 5H), 7.05 (d, J=8.2 Hz, 1H), 3.70 (d, J=25.4 Hz, 2H), 2.26 (s, 3H).

Example 3: 2-(5-(3-ethoxyphenyl)-1H-indol-3-yl) acetic acid (MK-2H

[Chemical Formula 29]

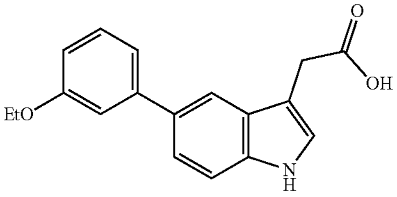

Synthesized according to Synthetic Procedure A and purified by reverse phase column chromatography (MeOH/MeCN). Yield: 23.0 mg, 39%, white solid.

$^1$H NMR (600 MHz, $CD_3OD$) δ 7.78 (s, 1H), 7.40 (d, J=8.2 Hz, 1H), 7.37 (dd, J=8.2, 1.4 Hz, 1H), 7.29 (t, J=7.9 Hz, 1H), 7.20 (d, J=6.9 Hz, 2H), 7.16 (s, 1H), 6.81 (dd, J=8.2, 2.1 Hz, 1H), 4.09 (q, J=6.9 Hz, 2H), 3.76 (s, 2H), 1.41 (t, J=7.2 Hz, 3H).

Example 4: 2-(5-(4-(tert-butyl) phenyl)-1H-indol-3-yl) acetic acid (MK-198

[Chemical Formula 30]

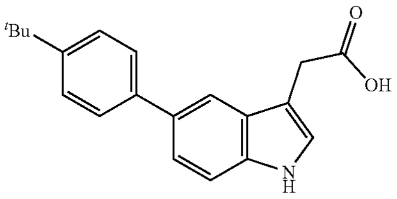

Synthesized according to Synthetic Procedure A and purified by reverse phase column chromatography (MeOH/MeCN). Yield: 3.4 mg, 4%, white solid.

$^1$H NMR (600 MHz, $CD_3OD$) δ 7.79 (s, 1H), 7.57 (d, J=8.6 Hz, 2H), 7.44 (d, J=8.6 Hz, 2H), 7.38 (s, 2H), 7.19 (s, 1H), 3.74 (s, 2H), 1.36 (s, 9H).

Example 5: 2-(5-(3,4-dimethylphenyl)-1H-indol-3-yl)acetic acid (MK-230

[Chemical Formula 31]

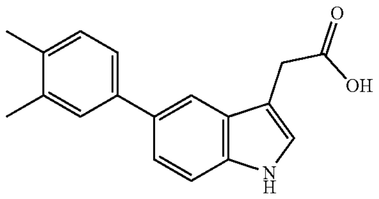

Synthesized according to Synthetic Procedure A and purified by reverse phase column chromatography (MeOH/MeCN). Yield: 29.0 mg, 51%, white solid.

$^1$H NMR (400 MHz, $CD_3OD$) δ 7.93 (s, 1H), 7.76 (s, 1H), 7.48-7.27 (m, 4H), 7.18 (s, 1H), 7.14 (d, J=7.9 Hz, 1H), 3.75 (s, 2H), 2.31 (s, 3H), 2.27 (s, 3H).

Example 6: 2-(5-(2,5-dimethylphenyl)-1H-indol-3-yl)acetic acid (MK-221

[Chemical Formula 32]

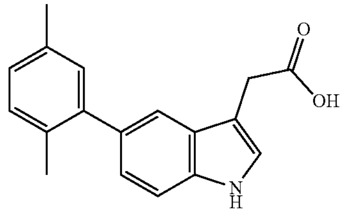

Synthesized according to Synthetic Procedure A and purified by reverse phase column chromatography (MeOH/MeCN). Yield: 25.1 mg, 45%, white solid.

$^1$H NMR (400 MHz, $CD_3OD$) δ 7.89 (s, 1H), 7.44 (s, 1H), 7.37 (d, J=8.6 Hz, 1H), 7.21 (s, 1H), 7.11 (d, J=7.3 Hz, 1H), 7.07-7.03 (m, 2H), 7.01 (d, J=7.9 Hz, 1H), 3.74 (s, 2H), 2.32 (s, 3H), 2.21 (s, 3H).

Example 7: 2-(5-(3,5-dimethylphenyl)-1H-indol-3-yl)acetic acid (MK-379

[Chemical Formula 33]

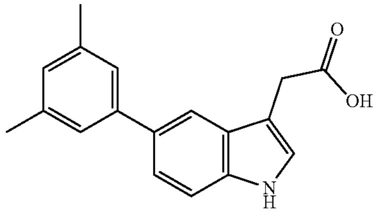

Synthesized according to Synthetic Procedure A and purified by reverse phase column chromatography (MeOH/MeCN). Yield: 60.0 mg, 43%, white solid.

$^1$H NMR (400 MHz, $CD_3OD$) δ 7.75 (s, 1H), 7.38 (d, J=8.4 Hz, 1H), 7.35 (d, J=8.4 Hz, 1H), 7.23 (s, 2H), 7.18 (s, 1H), 6.90 (s, 1H), 3.76 (s, 2H), 2.35 (s, 6H).

Example 8: 2-(5-(2-chloro-5-methylphenyl)-1H-indol-3-yl)acetic acid (MK-307

[Chemical Formula 34]

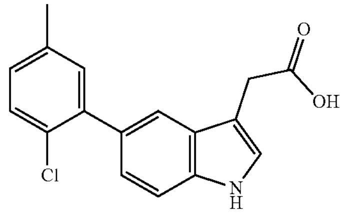

Synthesized according to Synthetic Procedure A and purified according to reverse phase column chromatography (MeOH/MeCN) and flash column chromatography (EtOAc/hexane=1:1). Yield: 4.7 mg, 8%, white solid.

$^1$H NMR (400 MHz, $CDCl_3$) δ 8.12 (bs, 1H), 7.64 (s, 1H), 7.39 (d, J=7.9 Hz, 1H), 7.34 (d, J=7.9 Hz, 1H), 7.30 (dd, J=8.3, 1.5H, 1H), 7.23-7.18 (m, 2H), 7.06 (dd, J=7.9, 1.8 Hz, 1H), 3.83 (s, 2H), 2.36 (s, 1H), 2.35 (s, 3H).

Example 9: 2-(5-(5-chloro-2-methylphenyl)-1H-indol-3-yl)acetic acid (MK-309

[Chemical Formula 35]

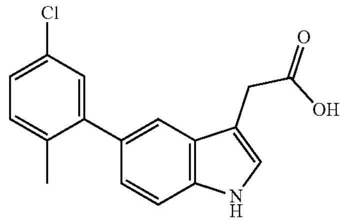

Synthesized according to Synthetic Procedure A, and purified by reverse phase column chromatography (MeOH/MeCN). Yield: 7.8 mg, 13%, white solid.

$^1$H NMR (400 MHz, $CDCl_3$) δ 8.13 (bs, 1H), 7.51 (s, 1H), 7.39 (d, J=7.9 Hz, 1H), 7.28 (d, J=1.8 Hz, 1H), 7.24 (s, 1H), 7.20 (dd, J=8.3, 2.1 Hz, 1H), 7.17 (d, J=8.6 Hz, 1H), 7.14 (d, J=9.8 Hz, 1H), 3.82 (s, 2H), 2.23 (s, 3H).

Example 10: 2-(5-(2,5-dichlorophenyl)-1H-indol-3-yl)acetic acid (MK-308

[Chemical Formula 36]

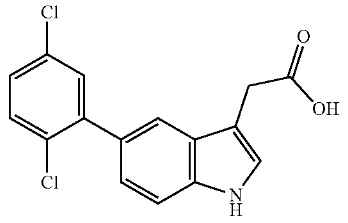

Synthesized according to Synthetic Procedure A and purified by flash column chromatography (MeOH/$CHCl_3$=1:9). Yield: 5.1 mg, 8%, white solid.

$^1$H NMR (400 MHz, $CDCl_3$) δ 8.19 (bs, 1H), 7.64 (s, 1H), 7.39 (d, J=2.4 Hz, 2H), 7.37 (d, J=1.8 Hz, 1H), 7.27-7.24 (m, 1H), 7.21 (dd, J=8.6, 2.4 Hz, 1H), 7.19 (s, 1H), 3.80 (s, 2H).

Example 11: 2-(5-(4-fluoro-3-methylphenyl)-1H-indol-3-yl)acetic acid (MK-213

[Chemical Formula 37]

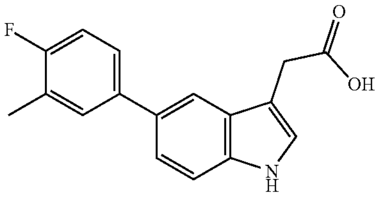

Synthesized according to Synthetic Procedure A and purified by reverse phase column chromatography (MeOH/MeCN). Yield: 25.5 mg, 45%, white solid.

$^1$H NMR (500 MHz, $CD_3OD$) δ 7.83 (d, J=1.1 Hz, 1H), 7.51 (dd, J=7.4, 2.3 Hz, 1H), 7.48-7.41 (m, 1H), 7.35 (d, J=8.0 Hz, 1H), 7.29 (dd, J=8.0, 1.7 Hz, 1H), 7.16 (s, 1H), 7.03 (t, J=9.2 Hz, 1H), 3.64 (s, 2H), 2.32 (s, 3H).

Example 12: 2-(5-(4-methoxy-3-methylphenyl)-1H-indol-3-yl)acetic acid (MK-214

[Chemical Formula 38]

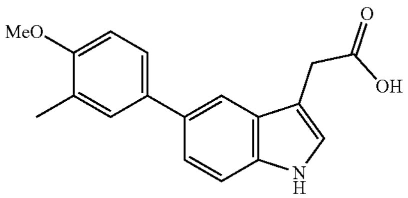

Synthesized according to Synthetic Procedure A, and purified by reverse phase column chromatography (MeOH/MeCN). Yield: 2.4 mg, 4%, white solid.

$^1$H NMR (600 MHz, $CD_3OD$) δ 7.80 (d, J=1.0 Hz, 1H), 7.43 (d, J=6.5 Hz, 2H), 7.33 (d, J=8.2 Hz, 1H), 7.30 (d, J=1.7 Hz, 1H), 7.15 (s, 1H), 6.92 (d, J=9.3 Hz, 1H), 3.85 (s, 3H), 3.64 (s, 2H), 2.25 (s, 3H).

Example 13: 2-(5-(benzo[d][1,3]dioxol-5-yl)-1H-indol-3-yl) acetic acid (MK-209

[Chemical Formula 39]

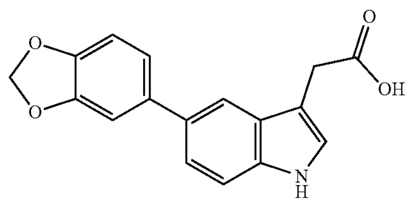

Synthesized according to Synthetic Procedure A and purified by reverse phase column chromatography (MeOH/MeCN). Yield: 27.1 mg, 46%, white solid.

$^1$H NMR (600 MHz, $CD_3OD$) δ 7.69 (d, J=1.4 Hz, 1H), 7.37 (d, J=8.8 Hz, 1H), 7.31 (dd, J=8.2, 1.7 Hz, 1H), 7.19 (s, 1H), 7.11 (d, J=1.7 Hz, 1H), 7.10 (dd, J=8.0, 1.9 Hz, 1H), 6.86 (d, J=7.8 Hz, 1H), 5.96 (s, 2H), 3.76 (s, 2H).

Example 14: 2-(5-(3-chloro-4-fluorophenyl)-1H-indol-3-yl)acetic acid (MK-255

[Chemical Formula 40]

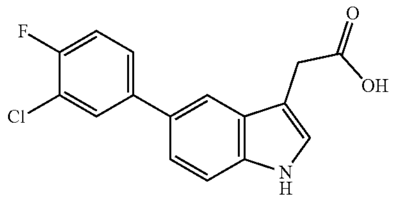

Synthesized according to Synthetic Procedure A and purified by reverse phase column chromatography (MeOH/MeCN). Yield: 38.9 mg, 64%, white solid.

$^1$H NMR (400 MHz, $CD_3OD$) δ 7.74 (d, J=1.2 Hz, 1H), 7.70 (dd, J=7.0, 2.1 Hz, 1H), 7.57 (qd, J=4.4, 2.3 Hz, 1H), 7.43 (d, J=8.6 Hz, 1H), 7.35 (dd, J=8.6, 1.8 Hz, 1H), 7.28 (d, J=9.2 Hz, 1H), 7.23 (d, J=11.6 Hz, 1H), 3.81 (s, 2H).

Synthesis Example 3: 2-(6-bromo-1H-indol-3-yl)-2-oxoacetic acid

[Chemical Formula 41]

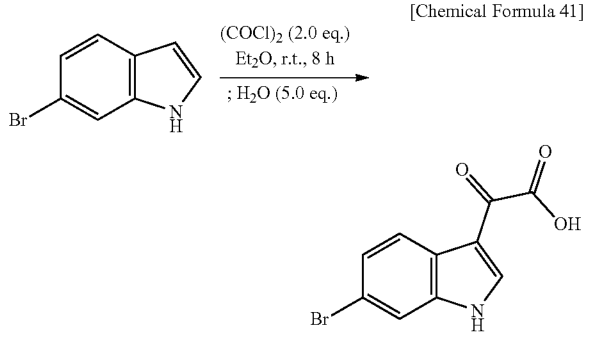

6-bromoindole (294.1 mg, 1.5 mmol) was dissolved in diethyl ether (5 mL) and the resulting solution was cooled to 0° C. Oxalyl chloride (257.3 μL, 2.0 equiv.) was added dropwise to the flask, and the resulting reaction mixture was returned to room temperature. After the mixture was stirred at room temperature for 2.5 hours, the reaction was quenched with water (60.1 μL, 5.0 equiv.). The reaction mixture was filtered to give 2-(6-bromo-1H-indol-3-yl)-2-oxoacetic acid as a pale yellow powder (275.0 mg, 68%).

$^1$H NMR (400 MHz, $CD_3OD$) δ 8.53 (s, 1H), 8.19 (d, J=8.6 Hz, 1H), 7.68 (d, J=1.8 Hz, 1H), 7.39 (dd, J=8.6, 1.8 Hz, 1H).

Synthesis Example 4: 2-(6-bromo-1H-indol-3-yl)acetic acid

[Chemical Formula 42]

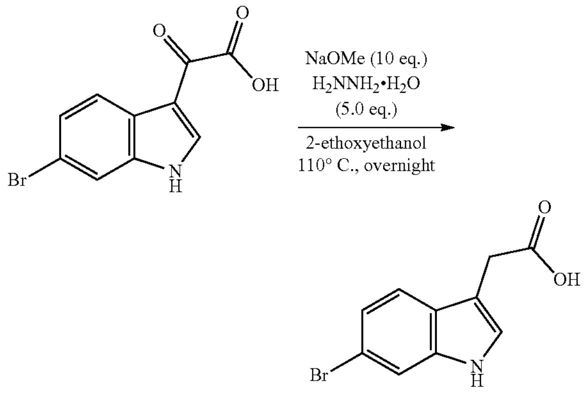

2-(6-bromo-1H-Indol-3-yl)-2-oxoacetic acid (200.0 mg, 746.1 μmol) was dissolved in 2-ethoxyethanol (3.3 mL), and hydrazine monohydrate (0.5 mL, 5 equiv.) was added to the flask. After stirring the reaction mixture at 60° C. for 40 minutes, NaOMe (393.3 mg, 10 equiv.) was added to the flask, and the mixture was stirred further at 150° C. for 7 hours. The reaction was quenched by the addition of water, and the aqueous layer was washed 3 times with ethyl acetate. The aqueous layer was acidified with 6 M aqueous hydrochloric acid, and the resulting precipitate was extracted with dichloromethane. The combined organic layers were dried over $Na_2SO_4$, filtered and concentrated under vacuum. The obtained residue was purified by reverse phase column chromatography (MeOH/MeCN) to give 2-(6-bromo-1H-indol-3-yl)acetic acid as a pale yellow powder (128.6 mg, 68%).

$^1$H NMR (400 MHz, $CD_3OD$) δ 7.50 (s, 1H), 7.45 (d, J=8.6 Hz, 1H), 7.17 (s, 1H), 7.12 (d, J=7.9 Hz, 1H), 3.71 (s, 2H).

Example 15: 2-(6-(m-tolyl)-1H-indol-3-yl)acetic acid (MK-245

[Chemical Formula 43]

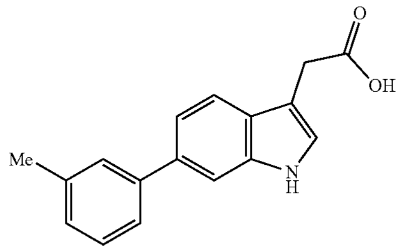

Synthesized according to Synthetic Procedure A and purified by reverse phase column chromatography (MeOH/MeCN). Yield: 25.0 mg, 47%, white solid.

$^1$H NMR (400 MHz, $CD_3OD$) δ 7.59 (d, J=7.9 Hz, 1H), 7.57 (s, 1H), 7.45 (s, 1H), 7.42 (d, J=7.9 Hz, 1H) 7.32-7.25 (m, 2H), 7.20 (s, 1H), 7.10 (d, J=7.3 Hz, 1H), 3.75 (s, 2H), 2.40 (s, 3H).

Example 16: 2-(6-([1,1'-biphenyl]-2-yl)-1H-indol-3-yl)acetic acid (MK-232

[Chemical Formula 44]

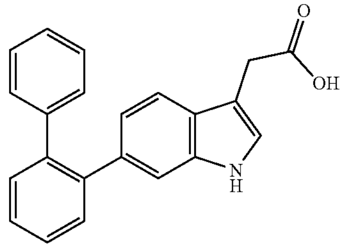

Synthesized according to Synthetic Procedure A and purified by reverse phase column chromatography (MeOH/MeCN). Yield: 31.9 mg, 49%, white solid.

$^1$H NMR (600 MHz, $CD_3OD$) δ 7.46-7.39 (m, 1H), 7.38-7.26 (m, 4H), 7.20-6.95 (m, 7H), 6.80 (dd, J=8.1, 1.5 Hz, 1H), 3.68 (s, 2H).

Example 17: 2-(6-(benzo[d][1,3]dioxol-5-yl)-1H-indol-3-yl)acetic acid (MK-247

[Chemical Formula 45]

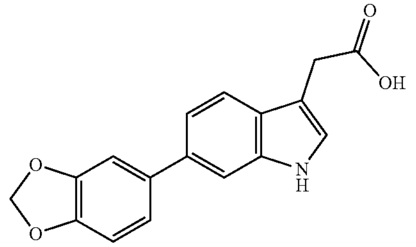

Synthesized according to Synthetic Procedure A and purified by reverse phase column chromatography (MeOH/MeCN) and recrystallization (MeOH/$CHCl_3$). Yield: 12.4 mg, 18%, brown solid.

$^1$H NMR (400 MHz, $CD_3OD$) δ 7.57 (d, J=7.9 Hz, 1H), 7.49 (s, 1H), 7.23 (dd, J=8.3, 1.5 Hz, 1H), 7.19 (s, 1H), 7.10 (dd, J=7.6, 1.5 Hz, 2H), 6.87 (d, J=9.2 Hz, 1H), 5.96 (s, 2H), 3.74 (s, 2H).

Example 18: 2-(6-(3-phenoxyphenyl)-1H-indol-3-yl)acetic acid (MK-248

[Chemical Formula 46]

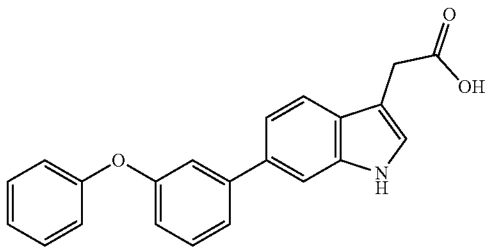

Synthesized according to Synthetic Procedure A and purified by reverse phase column chromatography (MeOH/MeCN) and recrystallization (MeOH/$CHCl_3$). Yield: 7.8 mg, 13%, yellow solid.

$^1$H NMR (400 MHz, $CD_3OD$) δ 7.69-7.59 (m, 3H), 7.56 (s, 1H), 7.41-7.33 (m, 2H), 7.30 (d, J=7.9 Hz, 1H), 7.20 (s, 1H), 7.15-7.08 (m, 1H), 7.07-7.00 (m, 4H), 3.73 (s, 2H).

Synthesis Example 5: Methyl 2-5-hydroxy-1H-indol-3-yl)acetate

[Chemical Formula 47]

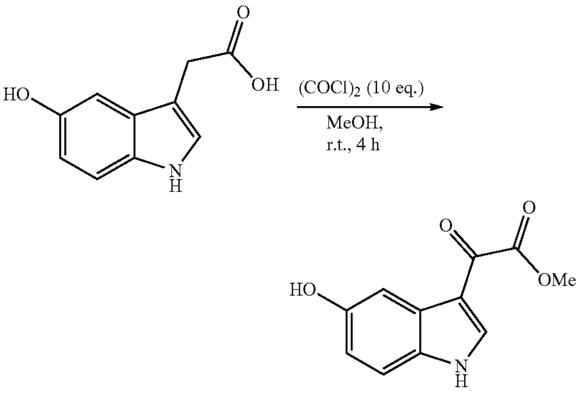

To a dilute solution of 5-hydroxy IAA (303.5 mg, 1.57 mmol) in methanol (7.5 mL) was added dropwise thionyl chloride (1.26 mL, 10 equiv.) at 0° C. The reaction mixture was stirred at room temperature for 4 hours. The mixture was quenched with saturated ammonium chloride and extracted with dichloromethane. The combined organic layers were dried over $Na_2SO_4$, filtered and concentrated under vacuum. The resulting residue was purified by flash column chromatography (hexane/EtOAc=1:1) to give methyl 2-(5-hydroxy-1H-indol-3-yl)acetate as a pale yellow oil (256.5 mg, 79%).

$^1$H NMR (400 MHz, $CDCl_3$) δ 8.08 (s, 1H), 7.06 (d, J=8.6 Hz, 1H), 7.00 (d, J=2.4 Hz, 1H), 6.96 (d, J=2.4 Hz, 1H), 6.71 (dd, J=8.6, 2.4 Hz, 1H), 3.66 (s, 2H), 3.65 (s, 3H).

Synthetic Procedure C

[Chemical Formula 48]

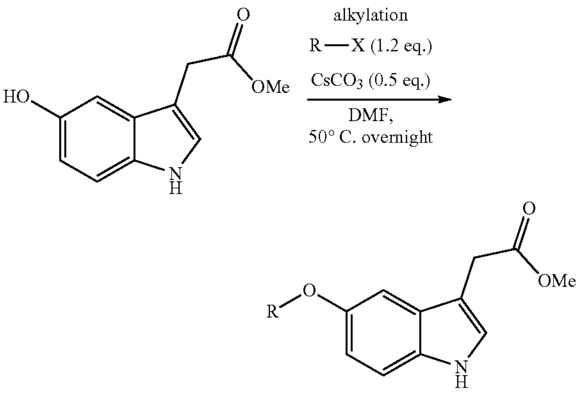

To a DMF solution (3 mL) of methyl 2-(5-hydroxy-1H-indol-3-yl)acetate (100 mg, 0.5 mmol) was added cesium carbonate (162 mg, 0.5 equiv.) and the corresponding alkyl iodide or aryl bromide (1.2 equiv.). The solution was then stirred at 50° C. for 4 hours. Water (50 mL) was added to the resulting solution, and the mixture was extracted with ethyl acetate. The combined organic layer was washed with saturated aqueous ammonium chloride and brine and dried over $Na_2SO_4$. The resulting residue was purified by flash column chromatography (hexane/EtOAc=4:1) to give the corresponding 5-alkoxy-indole-3-acetic acid methyl ester (methyl ester X).

Synthesis Example 6: Methyl 2-(5-((3-methylbenzyl)oxy)-1H-indol-3-yl)acetate

[Chemical Formula 49]

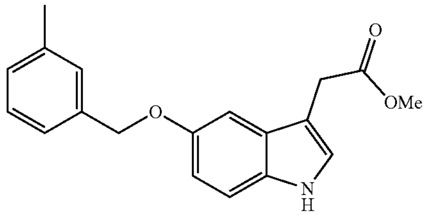

Synthesized according to Synthetic Procedure C. Yield: 7.4 mg, 12%, pale yellow oil.

$^1$H NMR (400 MHz, $CDCl_3$) δ 7.97 (s, 1H), 7.30 (s, 1H), 7.27 (d, J=4.9 Hz, 2H), 7.25 (d, J=8.4 Hz, 1H), 7.14 (dd, J=8.3, 2.8 Hz, 3H), 6.95 (dd, J=9.2, 2.4 Hz, 1H), 3.74 (s, 2H), 3.68 (s, 3H), 2.38 (s, 3H).

Synthesis Example 7: Methyl 2-(5-((4-methylbenzyl)oxy)-1H-indol-3-yl)acetate

[Chemical Formula 50]

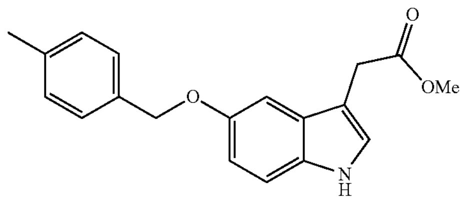

Synthesized according to Synthetic Procedure C. Yield: 2.9 mg, 5%, pale yellow oil.

$^1$H NMR (400 MHz, $CDCl_3$) δ 7.97 (bs, 1H), 7.36 (d, J=7.9 Hz, 2H), 7.25 (d, J=2.4 Hz, 1H), 7.19 (d, J=7.9 Hz, 2H), 7.13 (t, J=2.1 Hz, 2H), 6.93 (dd, J=8.6, 2.4 Hz, 1H), 3.73(s, 2H), 3.68 (s, 3H), 2.36 (s, 3H).

Synthetic Procedure D

[Chemical Formula 51]

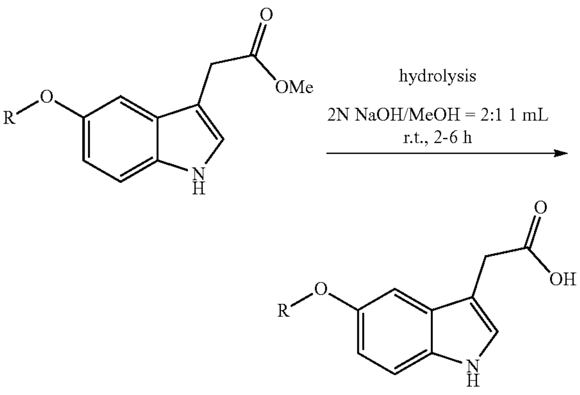

Methyl ester X was hydrolyzed at room temperature for 1 hour in aqueous methanol solution of sodium hydroxide (2N NaOH: MeOH=1:2). The mixture was acidified with 6 M aqueous hydrochloric acid, extracted with ethyl acetate, dried over $Mg_2SO_4$ and concentrated under reduced pressure. The crude product was purified by reverse phase column chromatography (MeOH/MeCN) to give the corresponding 5-alkoxy-indole-3-acetic acid.

Example 19: 2-(5-(heptyloxy)-1H-indol-3-yl)acetic acid (MK-323

[Chemical Formula 52]

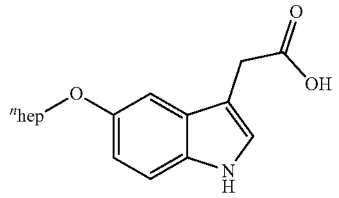

Methyl ester X was synthesized from 5-hydroxy IAA without purification in the alkylation step. The compound was synthesized according to Synthetic procedures C and D. Yield: 5.7 mg, 7% (two steps), pale yellow oil.

$^1$H NMR (400 MHz, $CDCl_3$) δ 8.12 (bs, 1H), 7.16 (d, J=9.2 Hz, 1H), 7.03 (s, 2H), 6.83 (d, J=6.9 Hz, 1H), 3.95 (t, J=6.5 Hz, 2H), 3.70 (s, 2H), 1.83-1.70 (m, 2H), 1.50-1.38 (m, 2H), 1.38-1.19 (m, 6H), 0.88 (t, J=6.9 Hz, 3H).

Example 20: 2-(5-(2-methylbutoxy)-1H-indol-3-yl) acetic acid (MK-322

[Chemical Formula 53]

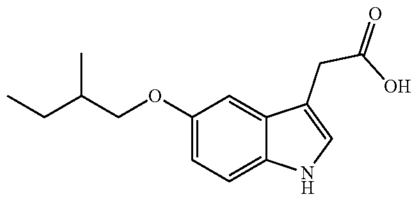

Methyl ester X was synthesized from 5-hydroxy IAA without purification in the alkylation step.

The compound was synthesized according to Synthetic procedures C and D. Yield: 7.2 mg, 3% (two steps), pale yellow solid.

$^1$H NMR (400 MHz, $CD_3OD$) δ 7.75 (s, 1H), 7.21 (d, J=8.6 Hz, 1H), 7.12 (s, 1H), 7.05 (d, J=1.8 Hz, 1H), 6.75 (dd, J=9.2, 2.4 Hz, 1H), 3.86 (q, J=4.9 Hz, 1H), 3.78 (q, J=5.1 Hz, 1H), 3.65 (s, 2H), 1.91-1.77 (m, 1H), 1.71-1.53 (m, 1H), 1.38-1.21 (m, 1H), 1.04 (d, J=6.7 Hz, 3H), 0.98 (t, J=7.6 Hz, 3H).

Example 21: 2-(5-(cyclohexylmethoxy)-1H-indol-3-yl)acetic acid (MK-333

[Chemical Formula 54]

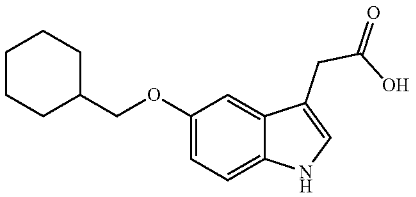

Methyl ester X was synthesized from 5-hydroxy IAA without purification in the alkylation step.

The compound was synthesized according to Synthetic procedures C and D. Yield: 3.2 mg, 9% (two steps), white solid.

$^1$H NMR (400 MHz, $CDCl_3$) δ 7.20 (d, J=8.6 Hz, 1H), 7.11 (s, 1H), 7.03 (s, 1H), 6.75 (d, J=8.6 Hz, 1H), 3.79 (d, J=5.5 Hz, 2H), 3.65 (s, 2H), 1.96-1.70 (m, 4H), 1.47-1.01 (m, 6H).

Example 22: 2-(5-((3-methylbenzyl) oxy)-1H-indol-3-yl)acetic acid (MK-349

[Chemical Formula 55]

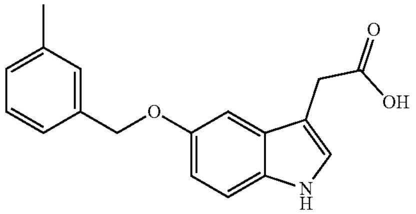

Synthesized according to Synthetic Procedure D. Yield: 9.3 mg, 88%, pale yellow solid.

$^1$H NMR (500 MHz, $CDCl_3$) δ 7.86 (bs, 1H), 7.16 (t, J=7.7 Hz, 1H), 7.14-7.09 (m, 2H), 7.09-7.01 (m, 2H), 6.95 (d, J=8.4 Hz, 1H), 6.86-6.78 (m, 2H), 4.88 (s, 2H), 3.49 (s, 2H), 2.26 (s, 3H).

Example 23: 2-(5-((4-methylbenzyl)oxy)-1H-indol-3-yl)acetic acid (MK-350

[Chemical Formula 56]

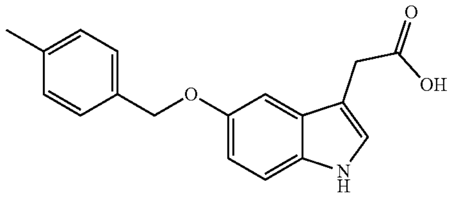

Synthesized according to Synthetic Procedure D. Yield: 2.3 mg, 83%, white solid.

$^1$H NMR (400 MHz, $CD_3OD$) δ 7.34 (d, J=7.9 Hz, 2H), 7.22 (d, J=8.6 Hz, 1H), 7.18 (d, J=7.3 Hz, 2H), 7.16 (d, J=2.4 Hz, 1H), 7.13 (s, 1H), 6.82 (dd, J=8.6, 2.4 Hz, 1H), 5.03 (s, 2H), 3.64 (d, J=9.2 Hz, 2H), 2.34 (s, 3H).

Synthetic Procedure E

To a screw tube was added 5-bromoindole-3-acetic acid (100 mg, 0.38 mmol), boronic acid (1.5 equiv.) and tetrakis (triphenylphosphine)palladium (13.4 mg, mol %), and the tube was then filled with nitrogen gas. Methanol (1 mL), toluene (1 mL) and 3 M aqueous sodium carbonate solution (0.23 mL, 3.0 equiv.) were added to the mixture, and the mixture was stirred at 65° C. for the duration of time shown for each example. The mixture was diluted with ethyl acetate and filtered through Cellite®. The filtrate was washed with saturated aqueous sodium bicarbonate solution, water, and brine. The organic layer was dried over $Na_2SO_4$, filtered and concentrated under vacuum. The obtained residue was purified by flash column chromatography (EtOAc/hexane=2:8 to 3:7).

Synthesis Example 8: 5-(2-methoxyphenyl)-indole-3-acetic acid methyl ester

[Chemical Formula 57]

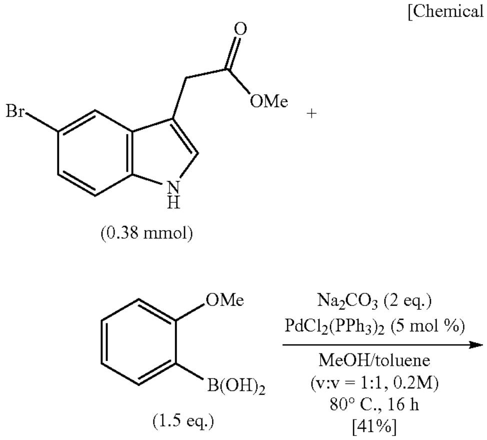

-continued

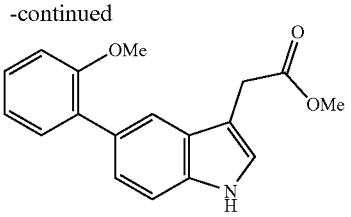

Synthesized according to Synthetic Procedure E (reaction time: 16 hours), to provide 5-(2-methoxyphenyl)-indole-3-acetic acid methyl ester as a light brown oil (45.8 mg, 41%).

$^1$H NMR (500 MHz, $CDCl_3$) δ 8.11 (s, 1H), 7.75 (s, 1H), 7.42 (s, 1H), 7.40 (s, 1H), 7.37-7.27 (m, 2H), 7.11 (s, 1H), 7.06 (t, J=7.3 Hz, 1H), 7.02 (d, J=7.7 Hz, 1H), 3.82 (s, 3H), 3.81 (s, 2H), 3.71 (s, 3H).; $^{13}$C NMR (125 MHz, $CDCl_3$) δ 172.7, 156.7, 135.4, 132.1, 131.5, 130.3, 128.0, 127.3, 124.5, 123.6, 120.9, 119.7, 111.4, 110.7, 108.7, 55.7, 52.1, 31.3; HRMS (ESI) m/z calcd' for $C_{18}H_{17}NO_3Na$ $[M+Na]^+$: 318.1101, found 318.1092.

Synthesis Example 9: 5-(3-methoxyphenyl)-indole-3-acetic acid methyl ester

[Chemical Formula 58]

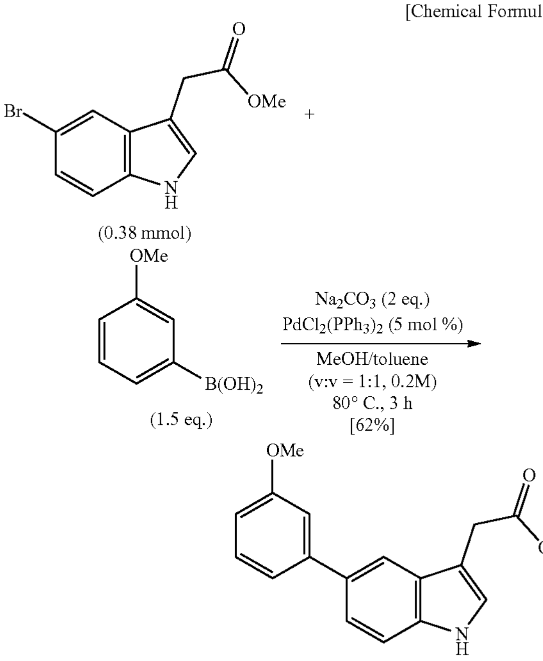

Synthesized according to Synthetic Procedure E (reaction time: 3 hours), to provide 5-(3-methoxyphenyl)-indole-3-acetic acid methyl ester as a light brown oil (70.0 mg, 62%).

$^1$H NMR (500 MHz, $CDCl_3$) δ 8.20 (s, 1H), 7.82 (s, 1H), 7.45 (d, J=8.4 Hz, 1H), 7.41-7.30 (m, 2H), 7.27 (d, J=6.1 Hz, 1H), 7.21 (s, 1H), 7.14 (t, J=9.6 Hz, 1H), 6.89 (d, J=7.7 Hz, 1H), 3.89 (s, 3H), 3.83 (s, 2H), 3.72 (s, 3H).; $^{13}$C NMR (125 MHz, $CDCl_3$) δ 172.7, 160.0, 144.2, 135.5, 129.7, 127.8, 124.2, 122.2, 120.2, 117.5, 113.4, 111.8, 111.8, 111.6, 108.8; HRMS (ESI) m/z calcd' for $C_{18}H_{17}NO_3Na$ $[M+Na]^+$: 318.1101, found 318.1099.

Synthesis Example 10: 5-(2-naphthyl)-indole-3-acetic acid methyl ester

[Chemical Formula 59]

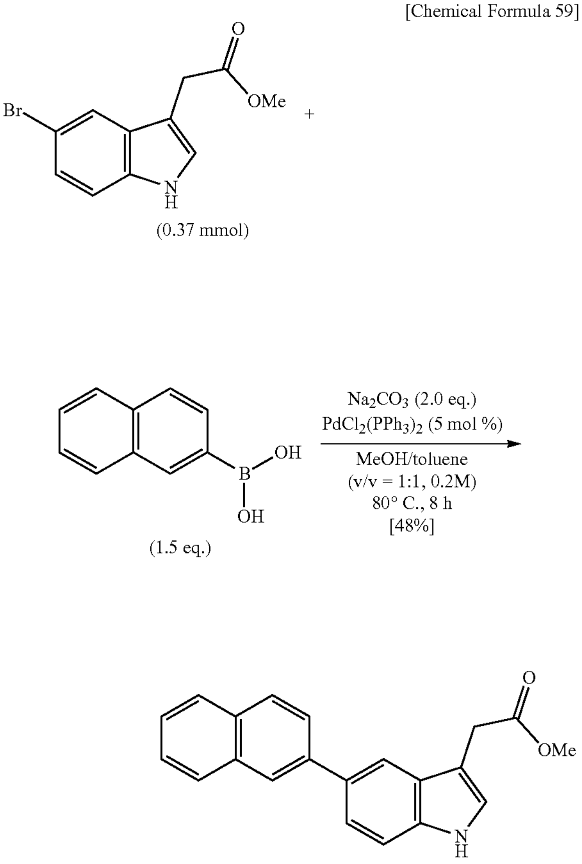

Synthesized according to Synthetic Procedure E (reaction time: 8 hours), to provide give 5-(2-naphthyl)-indole-3-acetic acid methyl ester as a light brown oil (56.6 mg, 48%).

$^1$H NMR (500 MHz, $CDCl_3$) δ 8.17 (s, 1H), 8.10 (s, 1H), 7.95 (s, 1H), 7.94-7.90 (m, 2H), 7.88 (d, J=8.4 Hz, 1H), 7.85 (dd, J=8.4, 1.5 Hz, 1H), 7.59 (dd, J=8.4, 1.5 Hz, 1H), 7.55-7.44 (m, 2H), 7.41 (d, J=8.4 Hz, 1H), 7.17 (d, J=6.9 Hz, 1H), 3.87 (s, 2H), 3.74 (s, 3H).; $^{13}$C NMR (125 MHz, $CDCl_3$) δ 172.7, 140.0, 135.8, 134.0, 132.3, 128.3, 128.2, 127.9, 127.8, 126.4, 126.3, 125.7, 125.6, 124.0, 122.5, 117.7, 111.7, 52.2, 31.3; HRMS (ESI) m/z calcd' for $C_2H_{17}NO_2Na$ $(M+Na]^+$: 338.1151, found 338.1149.

Synthetic Procedure F

To a solution methyl ester in tetrahydrofuran and water (v/v=1:1, 0.1 M) was added an aqueous solution of lithium hydroxide (5 equiv.), and the reaction mixture was stirred for 7 hours at room temperature. The mixture was washed with dichloromethane and acidified with 6 M aqueous hydrochloric acid. The aqueous layer was extracted with dichloromethane and the combined organic layers were dried over $Na_2SO_4$, filtered and concentrated under vacuum. The resulting residue was purified by normal phase or reverse phase column chromatography.

Example 24: (5-(2-methoxyphenyl)-indole-3-acetic acid (27A

[Chemical Formula 60]

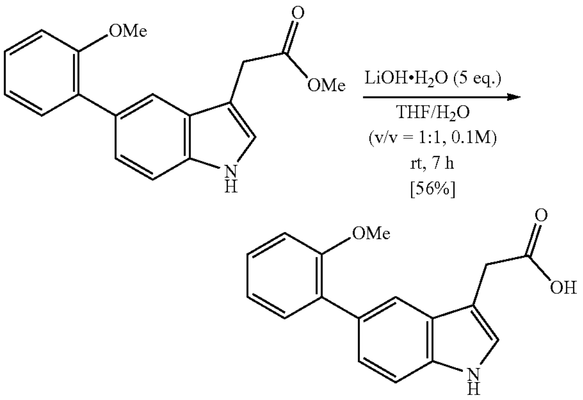

5-(2-Methoxyphenyl)-indole-3-acetic acid methyl ester (45.8 mg, 0.16 mmol) was hydrolyzed according to Synthetic Procedure F. The product was purified by flash column chromatography ($MeOH/CHCl_3$=1:10) followed by reverse phase column chromatography ($MeCN/H_2O$) to provide 5-(2-methoxyphenyl)-indole-3-acetic acid as a white solid (24.3 mg, 56%).

$^1H$ NMR (400 MHz, DMSO-$d_6$) δ 10.90 (s, 1H), 7.56 (s, 1H), 7.36 (d, J=8.6 Hz, 1H), 7.33-7.26 (m, 2H), 7.24 (d, J=2.4 Hz, 1H), 7.21 (dd, J=8.3, 1.5 Hz, 1H), 7.08 (d, J=7.3 Hz, 1H), 7.05-6.98 (m, 1H), 3.74 (s, 3C), 3.63 (s, 2H); $^{13}C$ NMR (100 MHz, DMSO-$d_6$) δ 173.3, 156.2, 135.2, 131.6, 130.7, 128.6, 127.8, 127.2, 124.2, 123.0, 120.6, 119.3, 111.7, 110.6, 108.3, 55.4, 31.4; HRMS (ESI) m/z calcd' for $C_{17}H_4NO_3$ $[MH]^-$: 280.0979 found 280.0974; HRMS (ESI) m/z calcd' for $C_{17}H_4NO_3$ $[MH]^-$: 280.0979, found 280.0976.

Example 25: 5-(3-methoxyphenyl)-indole-3-acetic acid (27B

[Chemical Formula 61]

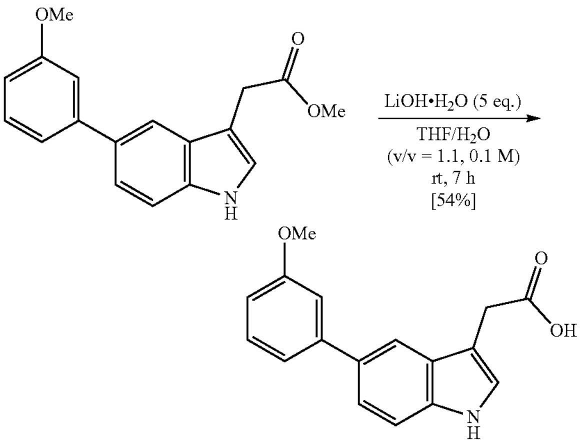

5-(3-Methoxyphenyl)-indole-3-acetic acid methyl ester (58.8 mg, 0.20 mmol) was hydrolyzed according to Synthetic Procedure F. The product was purified by flash column chromatography using Biotage® Isolera ($MeOH/CHCl_3$=1:10) followed by reverse phase column chromatography ($MeCN/H_2O$) to provide 5-(3-Methoxyphenyl)-indole-3-acetic acid as a white solid (30.1 mg, 56%).

$^1H$ NMR (500 MHz, DMSO-$d_6$) δ 10.97 (s, 1H), 7.79 (s, 1H), 7.42 (d, J=8.4 Hz, 1H), 7.39 (dd, J=8.4, 1.5 Hz, 1H), 7.35 (t, J=8.0 Hz, 1H), 7.27 (d, J=2.3 Hz, 1H), 7.22 (d, J=7.7 Hz, 1H), 7.17 (t, J=1.9 Hz, 1H), 6.87 (dd, J=8.4, 2.3 Hz, 1H), 3.83 (s, 3H), 3.70 (s, 2H).; $^{13}C$ NMR (125 MHz, DMSO-$d_6$) S 173.2, 159.6, 143.5, 135.8, 130.8, 129.7, 127.8, 124.7, 120.4, 119.1, 117.0, 112.3, 111.7, 111.6, 108.5, 55.0, 31.1; HRMS (ESI) m/z calcd' for $C_{17}H_4NO_3$ $[MH]^-$: 280.0979, found 280.0976.

Example 26: 5-(2-naphthyl)-indole-3-acetic acid (27D

[Chemical Formula 62]

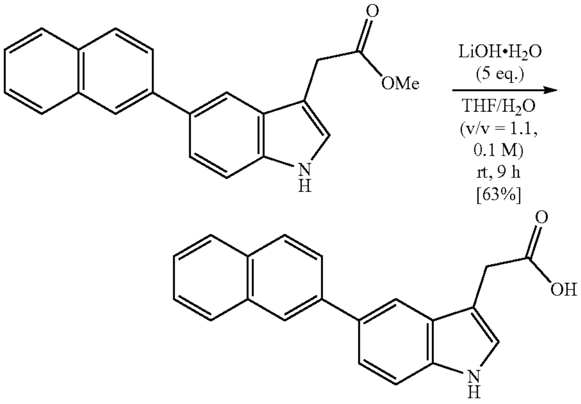

5-(2-Naphthyl)-indole-3-acetic acid methyl ester (22.2 mg, 75 μmol) was hydrolyzed according to Synthetic Procedure F. The compound was purified by reverse phase column chromatography ($MeCN/H_2O$) to provide 5-(2-Naphthyl)-indole-3-acetic acid as a white solid (34 mg, 63%).

$^1H$ NMR (600 MHz, DMSO-$d_6$) δ 12.19 (s, 1H), 11.01 (s, 1H), 8.17 (s, 1H), 7.99 (s, 1H), 7.98 (s, 1H), 7.96-7.90 (m, 2H), 7.88 (dd, J=8.2, 1.4 Hz, 1H), 7.56 (dd, J=8.6, 1.7 Hz, 1H), 7.52 (t, J=8.4 Hz, 1H), 7.50-7.45 (m, 2H), 7.29 (s, 1H), 3.74 (s, 2H).; $^{13}C$ NMR (150 MHz, $CDCl_3$) δ 177.3, 139.8, 135.7, 133.9, 133.2, 132.3, 128.4, 128.2, 127.9, 127.7, 126.3, 126.3, 125.7, 125.6, 124.2, 122.4, 117.7, 111.8, 109.0, 31.6; HRMS (ESI) m/z calcd' for $C_{20}H_{14}NO_2$ $[MH]^-$: 300.1030, found 300.1036.

Example 27: 5-(2-Phenyl)-indole-3-acetic acid (42A

[Chemical Formula 63]

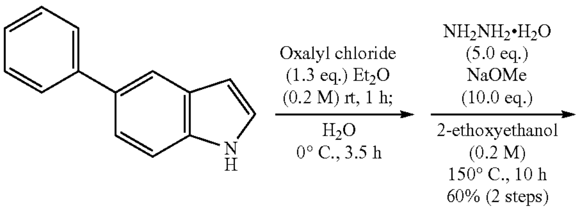

-continued

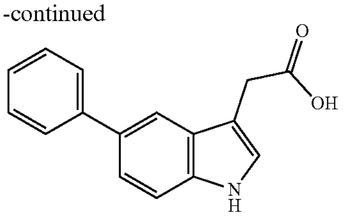

To a diethyl ether solution (3.4 mL, 0.2 M) of 5-Phenylindole (146 mg, 0.75 mmol) was slowly added oxalyl chloride (125 mg, 1.3 equiv.) at 0° C. After stirring the reaction mixture for 1 hour at room temperature, a mixture of diethyl etherate and water (v/v=2:1, 3 mL) was added at 0° C. The yellow precipitate was collected by filtration to give 168 mg of product. The product was used in the next reaction without purification. To a solution of 2-(5-Phenyl-1H-indol-3-yl)-2-oxoacetic acid (150 mg, 0.56 mmol) in 2-ethoxyethanol (3.0 mL, 0.2 M) was added sodium methoxide (310 mg, 10.0 equiv.) and hydrazine monohydrate (142 mg, 5.0 equiv.) at room temperature. The reaction mixture was stirred at 150° C. for 10 hours. At the end of the reaction, the mixture was diluted with water. The aqueous solution was washed 3 times with ethyl acetate and acidified with 2 M aqueous hydrochloric acid. The aqueous solution was extracted 3 times with ethyl acetate. The combined organic layer was washed with water, dried over $Na_2SO_4$ and concentrated under reduced pressure. The obtained crude product was purified by silica gel chromatography (10% MeOH in $CHCl_3$) to provide the target compound as white crystals (101 mg, 60%, 2 steps).

$^1H$ NMR (400 MHz, $CD_3OD$) δ 7.77 (s, 1H), 7.62 (d, J=7.3 Hz, 2H), 7.42-7.37 (m, 4H), 7.42 (t, J=7.3 Hz, 1H), 7.20 (s, 1H), 3.76 (s, 2H), NH proton and OH proton exhibit exchange with $CD_3OD$.; $^{13}C$ NMR (100 MHz, $CD_3OD$) δ 176.6, 144.2, 137.6, 133.7, 129.6, 129.2, 128.1, 127.1, 125.4, 122.2, 117.9, 112.5, 109.6, 32.1; HRMS (ESI) m/z calcd' for $C_{16}H_{13}NO_2Na$ $[M+Na]^+$: 274.0838, found 274.0838.

Synthetic Procedure G

[Chemical Formula 64]

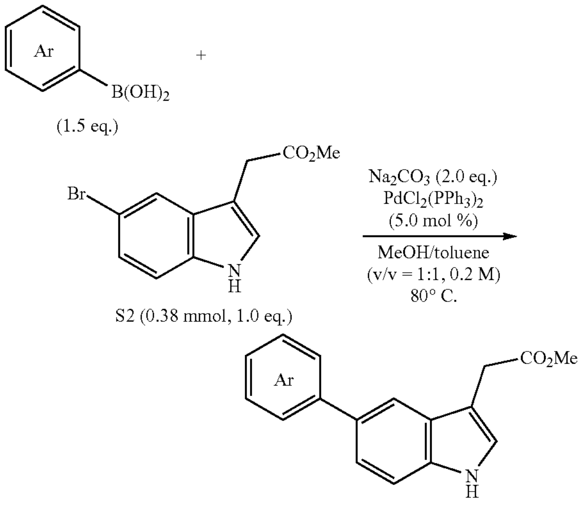

To a screw tube were added S2 (102 mg, 0.38 mmol), arylboronic acid (1.5 eq) and $PdCl_2$ $(PPh_3)_2$ (13.4 mg, 5.0 mol %), before evacuating the tube and filling it with nitrogen gas. To the mixture was added MeOH (1.0 mL), toluene (1.0 mL) and 3 M aqueous $Na_2CO_3$ solution (230 μL, 3.0 eq). The mixture was stirred at 80° C. for the following time(s). The mixture was diluted with EtOAc and filtered through Celite®. The filtrate was washed with saturated aqueous $NaHCO_3$ solution, $H_2O$ and brine. The organic layer was dried over $Na_2SO_4$, filtered and concentrated under reduced pressure. The residue was purified by flash column chromatography.

Synthetic Procedure H

[Chemical Formula 65]

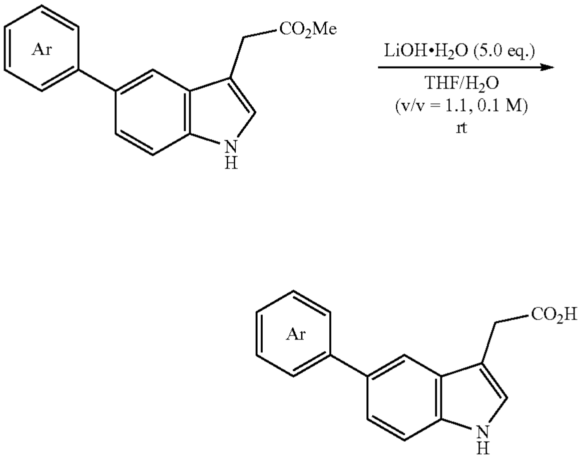

To a solution of methyl ester in a mixture of THE and $H_2O$ (v/v=1:1, 1.0 M) was added $LiOH \cdot H_2O$ (5.0 eq), and the reaction mixture was stirred for the duration of time indicated below at room temperature. The mixture was washed with $CH_2Cl_2$ and acidified with 6 M HCl. The aqueous layer was extracted with $CH_2Cl_2$ and the combined organic layers were dried over $Na_2SO_4$, filtered and concentrated under reduced pressure. The residue was purified by normal phase or reverse phase column chromatography.

Example 28: 2-(5-(Benzo[b]thiophen-2-yl)-1H-indol-3-yl)acetic acid (14

[Chemical Formula 66]

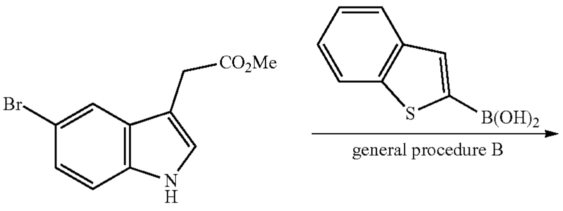

S2

-continued

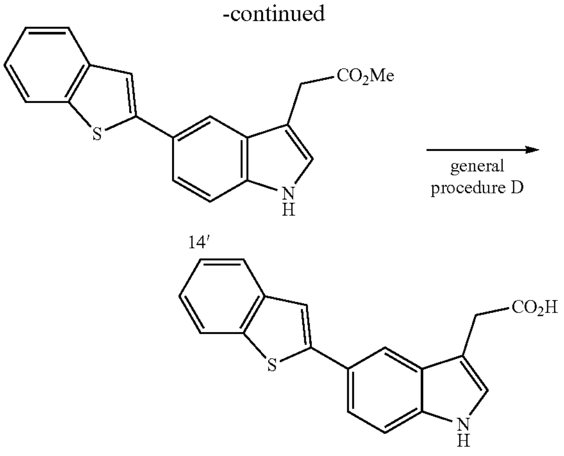

14'

14

Example 28-1: 2-(5-(Benzo[b]thiophen-2-yl)-1H-indol-3-yl)methyl acetate (14'

Synthesized according to Synthetic Procedure G (reaction time: 12 hours). The product was purified by flash column chromatography (hexane/EtOAc=3:1) to provide 14' (62.5 mg, 51%) as a white solid. $^1$H NMR (600 MHz, $CDCl_3$) δ 8.23 (s, 1H), 7.96 (s, 1H), 7.84 (d, J=7.6 Hz, 1H), 7.78 (d, J=8.2 Hz, 1H), 7.58 (d, J=8.2 Hz, 1H), 7.53 (s, 1H), 7.36 (t, J=7.6 Hz, 1H), 7.33 (d, J=8.9 Hz, 1H), 7.30 (t, J=7.6 Hz, 1H), 7.14 (s, 1H), 3.84 (s, 2H), 3.76 (s, 3H); $^{13}$C NMR (150 MHz, $CDCl_3$) δ 172.6, 146.1, 141.2, 139.4, 136.3, 127.7, 126.4, 124.5, 124.3, 123.9, 123.3, 122.3, 121.5, 118.3, 117.2, 111.8, 109.0, 52.2, 31.2; HRMS (ESI) m/z calcd' for $C_{19}H_5NNaO_2S$ $[M+Na]^+$: 344.0716, found 344.0717.

Example 28-2: 2-(5-(Benzo[b]thiophen-2-yl)-1H-indol-3-yl)acetic acid (14

14' (62.5 mg, 0.19 mmol) was hydrolyzed according to Synthetic Procedure H (reaction time: 17 hours). The product was purified by reverse phase column chromatography ($MeCN/H_2O$=1:4 to 3:7) to provide 14 (48.8 mg, 82%) as a white solid. $^1$H NMR (400 MHz, $CD_3OD$) δ 10.50 (s, 1H), 7.93 (d, J=1.2 Hz, 1H), 7.77 (d, J=8.0 Hz, 1H), 7.70 (d, J=7.3 Hz, 1H), 7.52 (dd, J=8.4, 1.2 Hz, 1H), 7.50 (s, 1H), 7.38 (d, J=8.6 Hz, 1H), 7.28 (t, J=7.0 Hz, 1H), 7.23 (d, J=7.9 Hz, 1H), 7.21 (s, 1H), 3.78 (s, 2H) One proton was missing due to proton exchange.; $^{13}$C NMR (150 MHz, $CD_3OD$) 176.4, 147.5, 142.6, 140.4, 138.1, 129.1, 126.7, 125.9, 125.3, 124.7, 124.1, 122.9, 121.5, 118.8, 117.7, 112.8, 109.7, 32.0; HRMS (ESI) m/z calcd' for $C_{18}H_{12}NO_2S$ $[MH]^-$: 306.0594, found 306.0589.

Example 29: 2-(5-cyclohexyl-1H-indol-3-yl)acetic acid (15

[Chemical Formula 67]

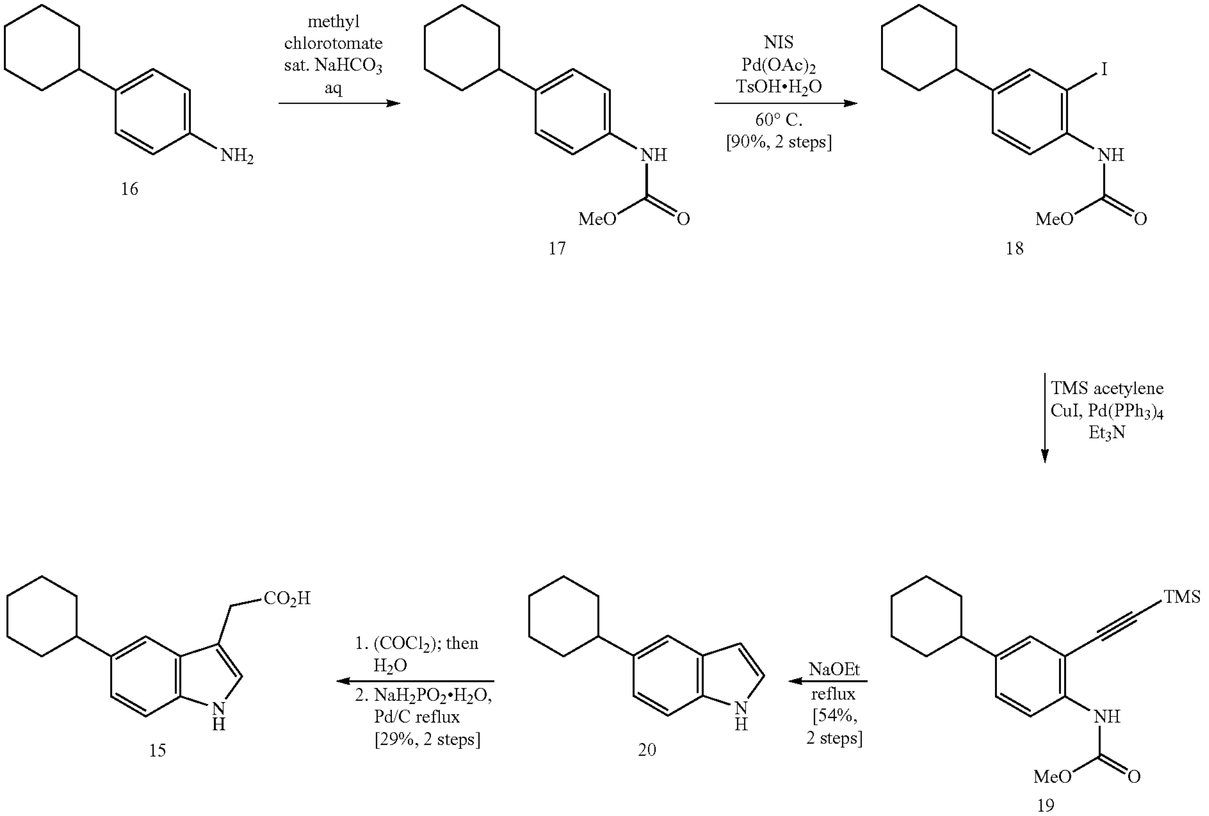

16

17

18

19

20

15

Example 29-1: Methyl(4-cyclohexyl-2-iodo-phenyl)carbamate (18

[Chemical Formula 68]

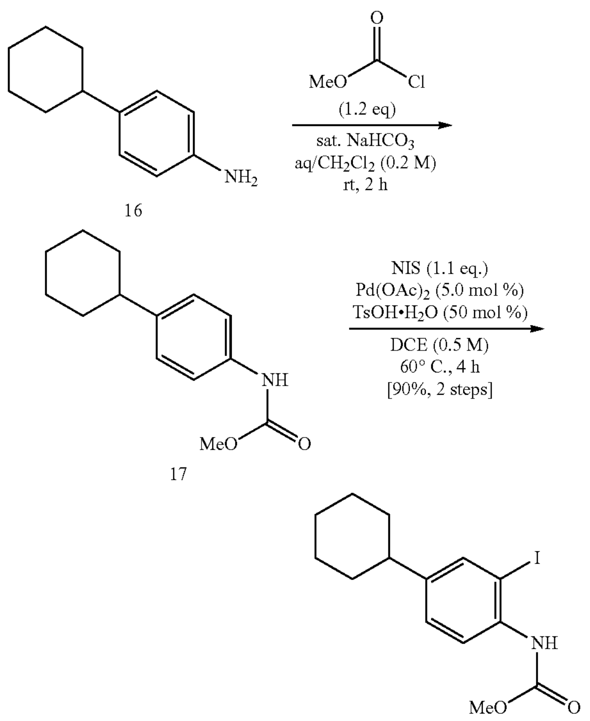

16

17

18

4-Cyclohexylaniline (16) (301 mg, 1.7 mmol) was dissolved in a mixture of $CH_2Cl_2$ (4 mL) and saturated aqueous $NaHCO_3$ (4 mL). To this mixture, methyl chloroformate (160 μL, 2.0 mmol, 1.2 eq) was added dropwise at 0° C. After stirring at ambient temperature for 2 hours, the reaction mixture was diluted with water and extracted with $CH_2Cl_2$. The combined organic layers were washed with brine, dried over $Na_2SO_4$, filtered and dried under vacuum. Crude product 17 (374 mg, crude yield: 93%) was used in the next reaction without further purification.

Iodination of 17 was performed under modified Jafari conditions. To a tube equipped with a stir bar, crude 17 (374 mg, 1.6 mmol), N-iodosuccinimide (NIS) (402 mg, 1.1 eq), TsOH·$H_2O$ (154 mg, 0.50 eq) and Pd $(0Ac)_2$ (18.0 mg, 5.0 mol %) were added, followed by addition of 1,2-dichloroethane (DCE) (3.2 mL). After stirring at 60° C. for 4 hours, the reaction mixture was cooled to ambient temperature and diluted with $CHCl_3$. The organic layer was washed with 1 M HCl, saturated aqueous $NaHCO_3$ and brine. The organic layer was then dried over $Na_2SO_4$, filtered and concentrated under reduced pressure. The product was purified by flash column chromatography (hexane to hexane/EtOAc=19:1) to provide 18 as a light brown solid (520 mg, 90% over 2 steps). $^1H$ NMR (600 MHz, $CDCl_3$) δ 7.88 (s, 1H), 7.59 (d, J=2.1 Hz, 1H), 7.18 (dd, J=8.6, 1.7 Hz, 1H), 6.84 (s, 1H), 3.79 (s, 3H), 2.43-2.40 (m, 1H), 1.83 (d, J=7.6 Hz, 4H), 1.74 (d, J=11.0 Hz, 1H), 1.44-1.29 (m, 4H), 1.29-1.15 (m, 1H); $^{13}C$ NMR (150 MHz, $CDCl_3$) δ 154.2, 145.6, 137.2, 136.2, 128.0, 120.6, 89.6, 52.7, 43.7, 34.5, 26.9, 26.2; HRMS (ESI) m/z calcd' for $C_{14}H_{18}INNaO_2$ $[M+Na]^+$: 382.0274, found 382.0261.

Example 29-2: 5-Cyclohexyl-1H-indole (20

[Chemical Formula 69]

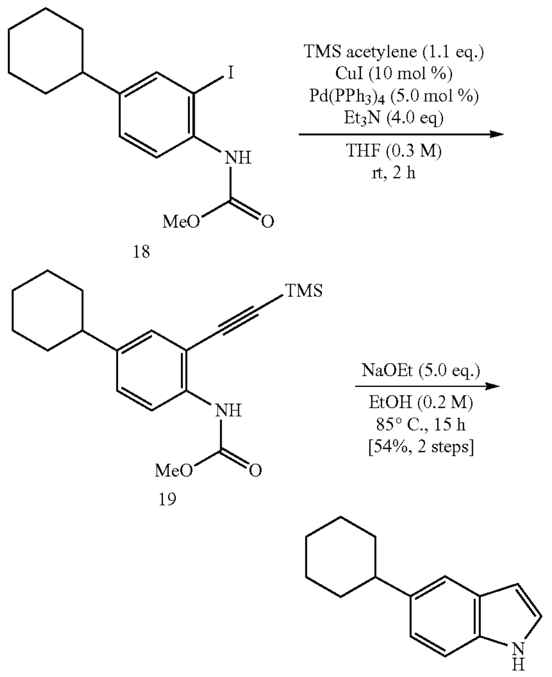

18

19

20

To a flask were added 18 (494 mg, 1.4 mmol), CuI (I) (27.2 mg, 0.14 mmol, 10 mol %) and $Pd(PPh_3)_4$ (80.1 mg, 69 μmol, 5.0 mol %). After evacuating the reaction vessel and refilling with nitrogen gas, anhydrous THE (5.0 mL), trimethylsilylacetylene (210 μL, 1.5 mmol, 1.1 eq) and degassed $Et_3N$ (800 μL, 5.5 mmol, 4.0 eq) were added. The reaction mixture was stirred at ambient temperature for 2 hours and subsequently diluted with EtOAc. The mixture was filtered through Celite® and the filtrate was washed with saturated aqueous $NH_4Cl$ solution and brine. The organic layer was dried over $Na_2SO_4$ and concentrated under reduced pressure. The residue was purified by flash column chromatography (hexane/EtOAc=99:1 to 19:1) and the semi-pure 19 was used in the next reaction without further purification (crude yield: 90%).

To an EtOH solution (5 mL) of crude 19 (410 mg, 1.2 mmol) was added NaOEt (423 mg, 6.2 mmol, 5.0 eq), and the mixture was stirred for 15 hours at 95° C. After cooling to ambient temperature, the mixture was diluted with EtOAc and washed with saturated aqueous $NaHCO_3$ and brine. The organic layer was dried over $Na_2SO_4$, filtered and concentrated under reduced pressure. The product was purified by flash column chromatography (hexane/EtOAc=19:1 to 9:1) to provide 20 as a light brown solid (148 mg, 54% over 2 steps). $^1H$ NMR (500 MHz, $CDCl_3$) δ 7.94 (s, 1H), 7.55 (s, 1H), 7.32 (d, J=8.4 Hz, 1H), 7.16-7.14 (m, 2H), 6.55 (d, J=1.5 Hz, 1H), 2.67 (t, J=10.7 Hz, 1H), 1.97 (dd, J=40.2, 11.9 Hz, 4H), 1.83 (d, J=12.3 Hz, 1H), 1.69-1.42 (m, 4H), 1.42-1.28 (m, 1H); $^{13}C$ NMR (150 MHz, $CDCl_3$) δ 139.9, 134.5, 128.1, 124.4, 121.8, 118.1, 110.8, 102.4, 44.8, 35.3, 27.3, 26.4; HRMS (ESI) m/z calcd' for $C_{14}H_{18}N$ $[M+H]^+$: 200.1434, found 200.1431.

Example 29-3: 2-(5-Cyclohexyl-1H-indol-3-yl)acetic acid (15

[Chemical Formula 70]

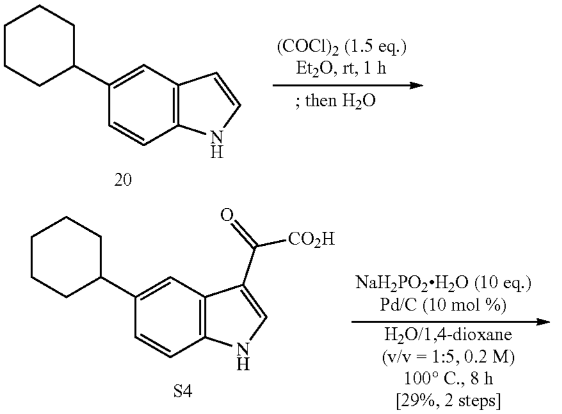

20
S4 the addition of $Et_2O/H_2O$. Filtration yielded crude α-keto acid S4 as a yellow solid. This was dried under vacuum and used in the next reaction without further purification.

To a $H_2O$/1,4-dioxane solution (v/v) of crude α-keto acid S4 and $NaH_2PO_2$ (475 mg, 10 equiv.) was added 10% Pd/C (47.7 mg, 10 mol %=1:5, 2 mL). The mixture was stirred at 100° C. for 9 hours. After cooling to ambient temperature, the reaction mixture was filtered through Celite®. The filtrate was washed with 1 M HCl and brine, dried over $Na_2SO_4$, filtered and concentrated under vacuum. The product was purified by reverse phase column chromatography ($MeCN/H_2O$=3:7 to 1:1) to provide 15 as a light brown solid (33.6 mg, 29% over 2 steps).

$^1H$ NMR (500 MHz, $CDCl_3$) δ 9.01 (s, 1H), 7.95 (s, 1H), 7.41 (s, 1H), 7.23 (d, J=8.3 Hz, 1H), 7.14-6.94 (m, 2H), 3.77 (s, 2H), 2.58 (tt, J=11.6, 3.2 Hz, 1H), 1.86 (dd, J=33.3, 13.4 Hz, 4H), 1.74 (d, J=13.0 Hz, 1H), 1.62-1.32 (m, 4H), 1.26 (qt, J=12.5, 3.4 Hz, 1H); $^{13}C$ NMR (125 MHz, $CDCl_3$) δ 177.9, 140.0, 134.8, 127.3, 123.5, 122.1, 116.2, 111.1, 107.9, 44.9, 35.3, 31.4, 27.2, 26.4; HRMS (ESI) m/z calcd' for $[MH]^-$: 256.1343, found 256.1343.

Example 30: 5-((3r, 5r, 7r)-adamantan-1-yl)-1H-indole (21

[Chemical Formula 71]

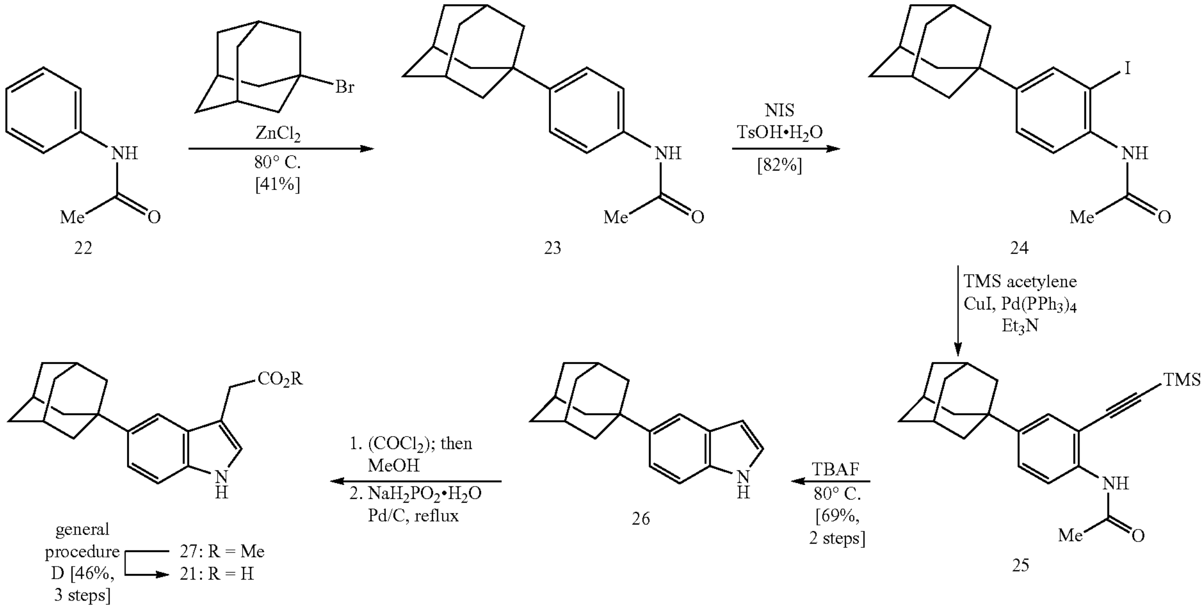

22
23
24
25
26

-continued

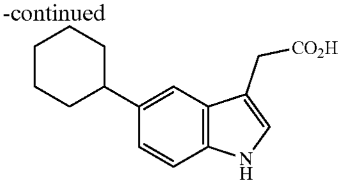
15

To a solution of 20 (89.3 mg, 0.45 mmol) in $Et_2O$ (4 mL) was added oxalyl chloride (60.0 μL, 0.67 mmol, 1.5 eq) dropwise at 0° C. The mixture was stirred at ambient temperature for 1 hour before the reaction was quenched by Example 30-1: N-(4-((3r, 5r, 7r)-adamantan-1-yl)phenyl)acetamide (23

[Chemical Formula 72]

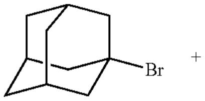
+
(1.1 equiv.)

-continued

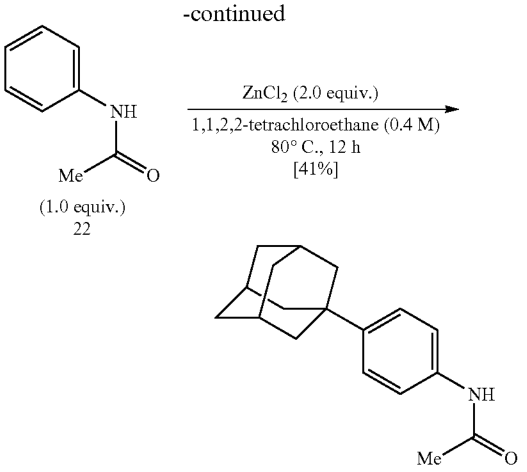

(1.0 equiv.)
22

23

To 1, 1, 2, 2-tetrafluoroethane were added acetanilide (22) (2.00 g, 15 mmol), 1-bromoadamantane (3.36 g, 16 mmol, 1.1 equiv.) and zinc chloride (4.03 g, 30 mmol, 2.0 equiv.)—tetrachloroethane (40 mL). The mixture was stirred at 80° C. for 12 hours. After the mixture was cooled to ambient temperature, it was concentrated in a rotary evaporator. The residue was diluted with EtOAc and washed with 1 M HCl and brine. The organic layer was dried over $Na_2SO_4$ and concentrated under reduced pressure. The product was purified by flash column chromatography (hexane/EtOAc=7:3 to 1:1) to provide 23 as a white solid (1.62 g, 41%). $^1H$ NMR (600 MHz, $CDCl_3$) δ 7.42 (d, J=8.2 Hz, 2H), 7.31 (d, J=8.9 Hz, 2H), 7.13 (s, 1H), 2.16 (s, 3H), 2.09 (s, 3H), 1.89 (s, 6H), 1.79-1.73 (m, 6H); $^{13}C$ NMR (150 MHz, $CDCl_3$) δ 168.3, 147.8, 135.4, 125.6, 119.9, 43.3, 36.9, 36.0, 29.1, 24.7; HRMS (ESI) m/z calcd' for $C_{18}H_{23}NNaO$ $[M+Na]^+$: 292.1672, found 292.1671.

Example 30-2: N-(4-((3r, 5r, 7r)-adamantan-1-yl)-2-iodophenyl)acetamide (24

[Chemical Formula 73]

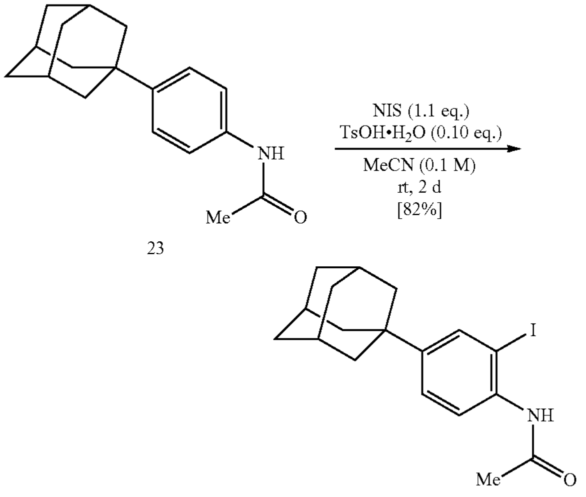

23

24

23 (500 mg, 1.9 mmol), NIS (440 mg, 2.0 mmol, 1.1 equiv.) and TsOH·$H_2O$ (35.3 mg, 0.19 mmol, 0.10 equiv.) were dissolved in MeCN (18 mL). The mixture was stirred at ambient temperature for 2 days and the solvent was removed using a rotary evaporator. The residue was dissolved in EtOAc and washed with saturated aqueous $NaHCO_3$ and brine. The organic layer was dried over $Na_2SO_4$, filtered and concentrated under reduced pressure. The product was purified by flash column chromatography (hexane/EtOAc=4:1 to 7:3) to provide 24 as a light brown solid (603 mg, 82%). $^1H$ NMR (400 MHz, $CDCl_3$) δ 7.97 (d, J=8.6 Hz, 1H), 7.70 (s, 1H), 7.47 (s, 1H), 7.30 (dd, J=8.6, 1.8 Hz, 1H), 2.19 (s, 3H), 2.07 (s, 3H), 1.84 (d, J=2.4 Hz, 6H), 1.78-1.69 (m, 6H); $^{13}C$ NMR (100 MHz, $CDCl_3$) δ 168.2, 149.7, 135.7, 135.3, 125.8, 122.4, 91.2, 43.0, 36.6, 35.8, 28.8, 24.6; HRMS (ESI) m/z calcd' for $C_{18}H_{22}INNaO$ $[M+Na]^+$: 418.0638, found 418.0643.

Example 30-3: 5-((3r, 5r, 7r)-adamantan-1-yl)-1H-indole (26

[Chemical Formula 74]

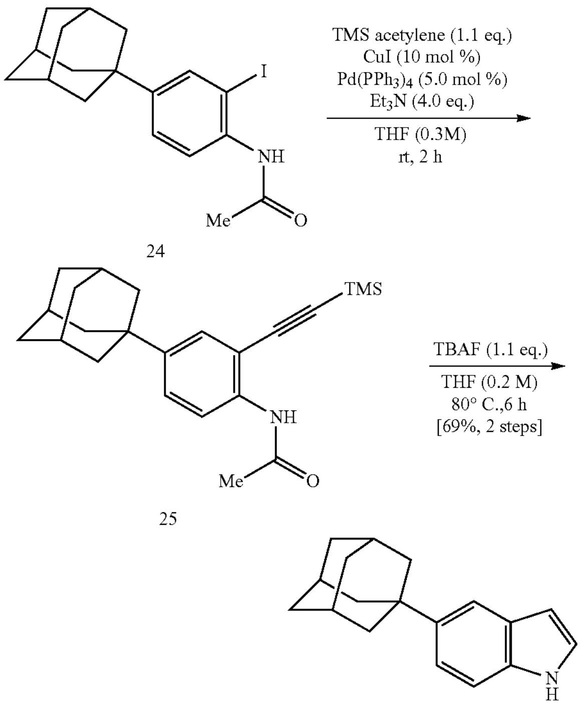

24

25

26

To the flask was added 24 (503 mg, 1.3 mmol), CuI (I) (26.9 mg, 0.13 mmol, 10 mol %) and $Pd(PPh_3)_4$ (76.7 mg, 64 μmol, 5.0 mol %). After evacuating the reaction vessel and filling with nitrogen gas, anhydrous THF (5 mL), trimethylsilylacetylene (200 μL, 1.4 mmol, 1.1 equiv.) and degassed triethylamine (710 μL, 5.1 mmol, 4.0 equiv.) were added to the solution. The reaction mixture was stirred at ambient temperature for 2 hours and subsequently diluted with EtOAc. The mixture was filtered through Celite® and the filtrate was washed with saturated aqueous $NH_4Cl$ and brine. The organic layer was dried over $Na_2SO_4$, filtered and concentrated under reduced pressure. The residue was purified by flash column chromatography (hexane/EtOAc=19:1 to 17:3) and the semi-pure 25 was used in the next reaction without further purification (crude yield: Quantitative).

To a solution of 25 (465 mg, 1.3 mmol) in anhydrous THF (5.0 mL) was added tetra-n-butylammonium fluoride (TBAF) (1 M THF solution, 1.4 mL; 1.4 mmol, 1.1 equiv.). After stirring at 80° C. for 6 hours, the mixture was diluted with EtOAc. The organic layer was washed with water and brine, dried over $Na_2SO_4$ and concentrated under vacuum. The product was purified by flash column chromatography (hexane/EtOAc=19:1 to 9:1) to provide 26 as a white solid (228 mg, 69% over 2 steps). $^1$H NMR (600 MHz, $CDCl_3$) δ 8.06 (s, 1H), 7.61 (s, 1H), 7.35 (d, J=8.2 Hz, 1H), 7.28 (dd, J=8.6, 1.7 Hz, 1H), 7.18 (t, J=m 2.7 Hz, 1H), 6.52 (s, 1H), 2.11 (s, 3H), 1.99 (d, J=2.7 Hz, 6H), 1.79 (s, 6H); $^{13}$C NMR (150 MHz, $CDCl_3$) δ 143.3, 134.2, 127.9, 124.3, 119.9, 116.4, 110.6, 102.9, 44.0, 37.1, 36.2, 29.3; HRMS (ESI) m/z calcd' for $C_{18}H_{20}N$ [MH]250.1601, found 250.1597.

Example 30-4: 2-(5-((3r, 5r, 7r)-adamantan-1-yl)-1H-indol-3-yl)acetic acid (21

[Chemical Formula 75]

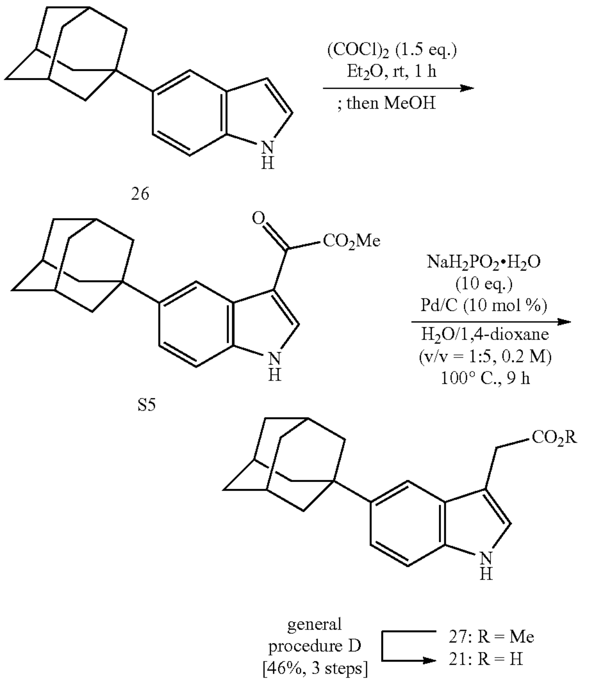

26

S5

To a solution of 26 (64.9 mg, 0.26 mmol) in $Et_2O$ (2 mL) was added oxalyl chloride (35.0 μL, 0.39 mmol, 1.5 equiv.), dropwise at 0° C. After the mixture was stirred at ambient temperature for 1 hour, the reaction was quenched by the addition of $Et_2O$/MeOH. Filtration yielded the crude α-ketoester S5 as a yellow solid. It was dried under vacuum and used in the next reaction without further purification.

To a solution of crude α-ketoesters S5 and $NaH_2PO_2 \cdot H_2O$ (274 mg, 10 equiv.) in $H_2O$/1,4-dioxane (v/v) was added 10% Pd/C (27.5 mg, 10 mol %=1:5, 1 mL). The mixture was stirred at 100° C. for 9 hours. After cooling to ambient temperature, the reaction mixture was filtered through Celite®. The filtrate was washed with 1 M HCl and brine, dried over $Na_2SO_4$ and concentrated under reduced pressure. 27 was used in the next reaction without further purification.

Crude product 27 was hydrolyzed according to Synthetic Procedure H (reaction time: 4 hours). The product was purified by flash column chromatography (hexane/EtOAc=1:1 to 2:3) to provide 21 as a white solid (36.5 mg, 46% over 3 steps). $^1$H NMR (600 MHz, $CDCl_3$) δ 7.94 (s, 1H), 7.56 (s, 1H), 7.35-7.27 (m, 2H), 7.12 (d, J=2.1 Hz, 1H), 3.83 (s, 2H), 2.13 (s, 3H), 2.01 (d, J=2.1 Hz, 6H), 1.83-1.78 (m, 6H); $^{13}$C NMR (150 MHz, $CDCl_3$) δ 178.3, 143.4, 134.4, 127.0, 123.4, 120.3, 114.3, 110.9, 107.9, 43.9, 37.1, 36.2, 31.2, 29.3; HRMS (ESI) m/z calcd' for $C_{20}H_{=}NO_2$ $[MH]^-$: 308.1656, found 308.1659.

Test Example 1: Evaluation of Binding to Auxin Receptor (Yeast Two-Hybrid Assay

As test compounds, we used the auxin derivative 2-(5-(Benzyloxy)-1H-indole-3-yl)acetic acid (MK-348: can be purchased from Sigma-Aldrich, etc.) and 2-(5-(butyloxy)-1H-indol-3-yl)acetic acid (RY-215: J. Biol. Chem. 2011, 286, 235) synthesized in Examples, as well as various compounds including auxin (indole-3-acetic acid), to evaluate their binding to wild-type auxin receptor and mutant auxin receptor. Specifically, the inventors set up the assay in the following manner.

Yeast strain EGY48 was transformed into a plasmid (pSH18-34) containing a LacZ expression cassette (LexA-operon: LacZ reporter) that is transcriptionally regulated by the LexA-operon, a plasmid derived from pGLex313 containing an expression cassette of LexA-DNA-binding domain fusion protein A (the wild-type auxin receptor: SEQ ID NO. 1, or mutant auxin receptor (TIR1 F79G) where the amino acid residue 79 (phenylalanine) in the wild-type is mutated to a glycine: SEQ ID NO. 2), and a plasmid derived from pJG4-5 containing an expression cassette of B42 transcription activator fusion protein B (AUX/IAA protein: SEQ ID NO: 3). The transformant was cultured at 30° C. on an agar plate made of yeast growth medium (minimal SD base and -His/-Trp/-Ura dropout supplement). The colonies were picked up and incubated overnight in liquid SD/-His/-Trp/-Ura medium at 30° C. Afterwards, the medium was replaced with a liquid medium composed of minimal SD/Gal/Raf base, -His/-Trp/-Ura dropout supplement, 50 mM Na-phosphate buffer (pH 7.0), 80 mg/mL X-gal, and various concentrations of test compounds. After incubation at 30° C. for 3 days, the medium containing yeast was transferred to a white 96-well plate (flat bottom) and observed. The lower the concentration of the test compound when blue color appears, the higher the binding between the test compound and the auxin receptor (wild type or mutant) is. Conversely, higher the concentration of test compound when the blue color appears for the first time, the lower the binding between the test compound and the auxin receptor (wild type or mutant).

Table 1 shows the names of test compounds as described in this specification, the example numbers, the identity of $R^1$, $R^2$, n and m in the General Formula (1) and the results. In Table 1, the concentration of "wt TIR" indicates the minimum concentration of the test compound in which the well turns blue when the wild type auxin receptor is used, whereas the concentration of "mut" indicates the minimum concentration of the test compound in which the well turns blue when the mutant auxin receptor (TIR1 F79G) is used.

TABLE 1

| Compound name | Example No. | $R^1$ | n | $R^2$ | m | wt TIR (μM) | mut TIR (μM) |
|---|---|---|---|---|---|---|---|
| Indole-3-acetic acid | — | Hydrogen atom | 0 | Hydrogen atom | 0 | 0.1 | >100 |
| 42A | 27 | Phenyl | | | | 1 | 0.01 |
| MK-189 | 1 | o-tolyl | | | | 10 | 0.1 |
| 27A | 24 | 2-Methoxyphenyl; | | | | 100 | 10 |
| MK-190 | 2 | m-Tołyl | | | | 10 | 0.1 |
| 27B | 25 | 3-Methoxyphenyl | | | | 100 | 1 |
| MK-211 | 3 | 3-Ethoxyphenyl | | | | 100 | 10 |
| MK-198 | 4 | 4-(tert-butyl)phenyl | | | | 100 | 10 |
| MK-230 | 5 | 3,4-Dimethylphenyl | | | | 10 | 0.1 |
| MK-221 | 6 | 2,5-Dimethylphenyl | | | | >100 | 10 |
| MK-379 | 7 | 3,5-Dimethylphenyl | | | | 100 | 1 |
| MK-307 | 8 | 2-Chloro-5-Methylphenyl | | | | >100 | 10 |
| MK-309 | 9 | 5-Chloro-2-Methylphenyl | | | | 100 | 10 |
| MK-308 | 10 | 2,5-Dichlorophenyl | | | | 100 | 10 |
| MK-213 | 11 | 4-Fluo-3-Methylphenyl | | | | 10 | 0.1 |
| MK-214 | 12 | 4-Methoxy-3-methylphenyl | | | | 100 | 10 |
| MK-209 | 13 | Benzo[d][1,3]dioxol-5-yl | | | | 10 | 0.1 |
| 27D | 26 | 2-Naphthyl | | | | 10 | 0.1 |
| MK-255 | 14 | 3-Chloro-4-Buorophenyl | | | | 100 | 1 |
| MK-245 | 15 | Hydrogen atom | | m-Tołyl | | 10 | 0.1 |
| MK-232 | 16 | | | [1,1'-Biphenyl]-2-yl | | 100 | 10 |
| MK-247 | 17 | | | Benzo[d][1,3]dioxol-5-yl | | 10 | 0.1 |
| MK-248 | 18 | | | 3-Phenoxyphenyl | | 10 | 0.1 |
| RY-215 | — | n-Butyl | 1 | Hydrogen atom | | 10 | 0.1 |
| MK-323 | 19 | n-Heptyl | 1 | | | 100 | 10 |
| MK-322 | 20 | 2-Methylbutyl | 1 | | | 10 | 0.1 |
| MK-333 | 21 | Cyclohexyimethyl | 1 | | | 100 | 0.1 |
| MK-348 | — | Benzyl | 1 | | | 100 | 0.1 |
| MK-348 | 22 | 3-Methylbenzyl | 1 | | | >100 | 10 |
| MK-350 | 23 | 4-Methylbenzyl | 1 | | | >100 | 100 |
| Compound 14 | 28 | 1-Adamantyl | 0 | | | >1 | 0.01 |
| Compound 15 | 29 | Cyclohexylmethyl | | | | 0.1 | 0.001 |
| Compound 21 | 30 | 2-Benzoethyl | | | | 0.1 | 0.001 |

As shown in Table 1, the binding affinity of the mutant auxin receptor used in this study (TIR1 F79G) to auxin (indole-3-acetic acid) is less than 1/1000 of that of the wild type auxin receptor, which suggests that the mutant receptor is a reduced auxin-sensitivity auxin receptor. Previously published literature (Nature, Vol 446, 5 Apr. 2007, pp 640-645) analyzed the interaction region between auxin (indole-3-acetic acid) and its receptor (TIR1). Here, it was reported that the amino acid residues in the wild type auxin receptor (SEQ ID NO: A) that interacts with the benzene ring of the auxin indole ring are residues 79 and 82 (phenylalanine) from the N-terminus. The above results are consistent with this report.

On the other hand, auxin derivatives used in this study all bound to the wild-type auxin receptor with weaker affinity than auxin (indole-3-acetic acid), and their binding affinity to the mutant auxin receptor with reduced auxin sensitivity (TIR1 79G) was greater than their affinity to the wild-type auxin receptor. These results suggested that the auxin derivatives in this study were able to act more effectively on reduced auxin-sensitivity auxin receptor expressed only in specific tissues and cells, while having reduced influence on the endogenous auxin receptors in plants is more effective against auxin receptors with reduced auxin receptivity expressed only in specific tissues and cells with a reduced effect on the endogenous auxin receptor in plants. Eventually, these derivatives were able to produce the auxin-response signals in targeted tissues and cells alone, while reducing the adverse effects of auxin application.

Test Example 2: Evaluation of Plant Growth Regulating Action 1 (Root Elongation Assay

*Arabidopsis* seeds having the expression cassette of mutant auxin receptor (TIR1 F79G) (SEQ ID NO: B) or wild-type *Arabidopsis* seeds without said expression cassette were sterilized and stored at 4° C. in the dark for several days. The seeds were transferred to 0.5× Murashige and Skoog (MS) liquid medium and incubated for 1 day at 22° C. in the light with shaking at 140 rpm. The test compound was added to the medium at various concentrations and the seeds were further incubated for 1 week. After incubation, the roots were observed in a state where their lengths could be compared. If an auxin response signal has been produced in the root, root elongation will be suppressed. The results are shown in FIG. 1

As shown in FIG. 1, the auxin derivative synthesized in Example did not inhibit root elongation in wild-type *Arabidopsis* seeds, but inhibited root elongation in *Arabidopsis* seeds expressing the mutant auxin receptor (TIR1 F79G). These results indicated that the auxin derivative in the Example not only bound to the reduced auxin-sensitivity receptor, but was also able to produce a normal auxin response signal.

Test Example 3: Evaluation of Plant Growth Regulating Action 2 (Lateral Root Growth Assay

*Arabidopsis* seeds (5 days old) having expression cassette containing the mutant auxin receptor (TIR1 F79G) (SEQ ID NO: B), or wild-type *Arabidopsis* seeds (5 days old) without said expression cassette were seeded on 0.5× MS plates containing the test compound at a concentration of 1 μM. After incubation for 40 hours, the seeds were clarified with chloral hydrate, and then the lateral root primordium in the seeds was observed. If an auxin response signal has been produced, the number of lateral root primordia increases. The results are shown in FIG. 2

Figure 2:
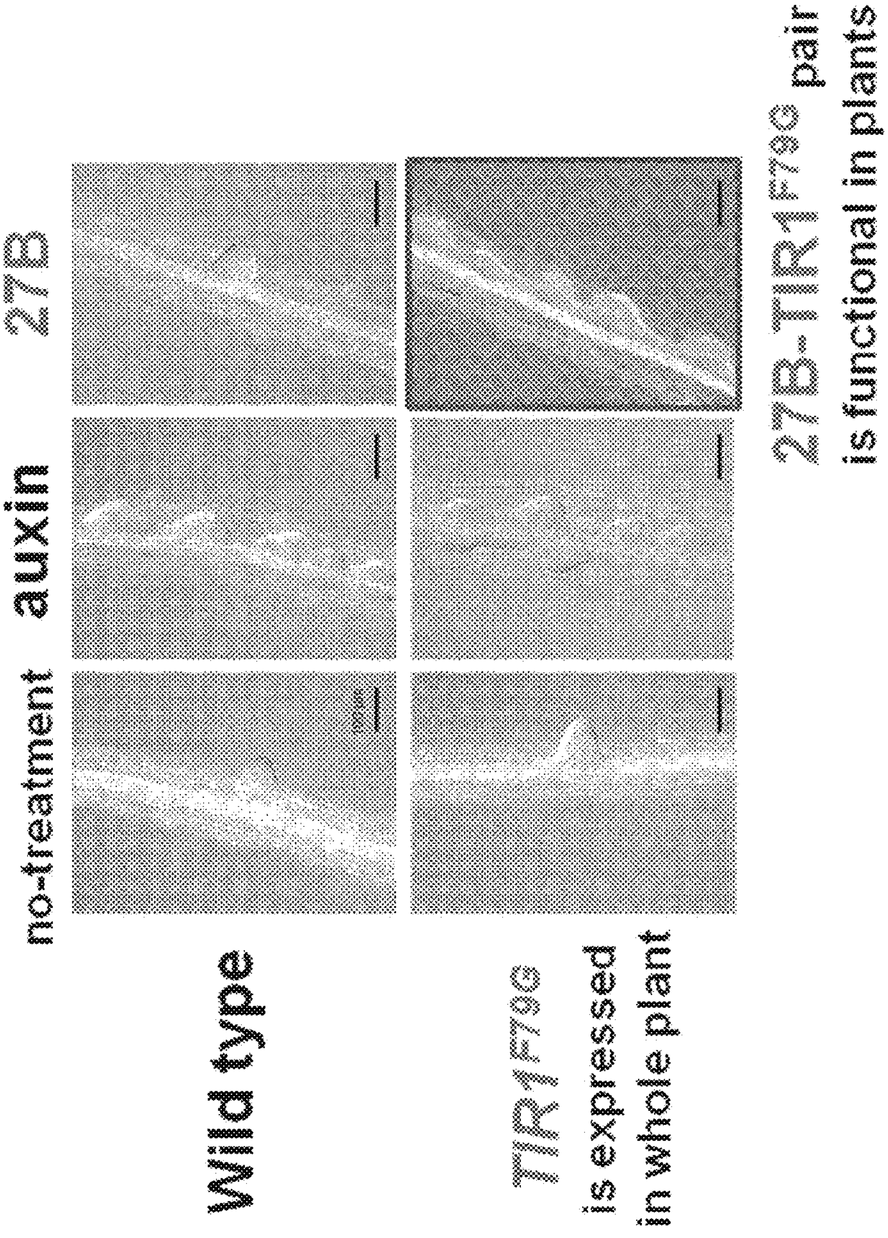
FIG. 2 This shows the results of a lateral root growth assay in Test Example 3. On the left side of the photo, "$TIR1^{F79G}$" indicates experiments using *Arabidopsis* seeds having an expression cassette of a mutant auxin receptor (TIR1 F79G), whereas "Wild type" indicates a wild type *Arabidopsis* seeds without this expression cassette. On the upper side of the photo, "auxin" indicates experiments using auxin (indole-3-acetic acid) as the test compound, whereas "27B" indicates experiments using the auxin derivative synthesized in Example 25 as the test compound, and "no-treatment" indicates experiments where the plants were not treated with test compounds. The bar in each photo represents a 100 μm scale.

As shown in FIG. 2, the auxin derivative synthesized in Example does not induce lateral root growth in wild-type *Arabidopsis* seeds, but induced lateral root growth in *Arabidopsis* seed expressing the mutant auxin receptor (TIR1 F79G). This showed that the auxin derivatives of Examples not only bind to the auxin receptor-reduced auxin receptor but can induce a normal auxin response signal.

Test Example 4: Evaluation of Plant Growth Regulator Action 3 (Lateral Root Growth Assay An expression cassette of a fused protein between the mutant auxin receptor (TIR1 F79G) (SEQ ID NO: B) and GUS, was introduced to *Arabidopsis thaliana* plants containing the GAL4 expression cassette (the promoter being a xylem pole pericycle cell-specific promoter). The assay was carried out in the same manner as in Test Example 3, using the seeds obtained from plants (5 days old), or the seeds of *Arabidopsis* plants (5 days old) not containing the fusion protein expression cassette and containing the GAL4 expression cassette. The results are shown in FIG. 3

Figure 3:
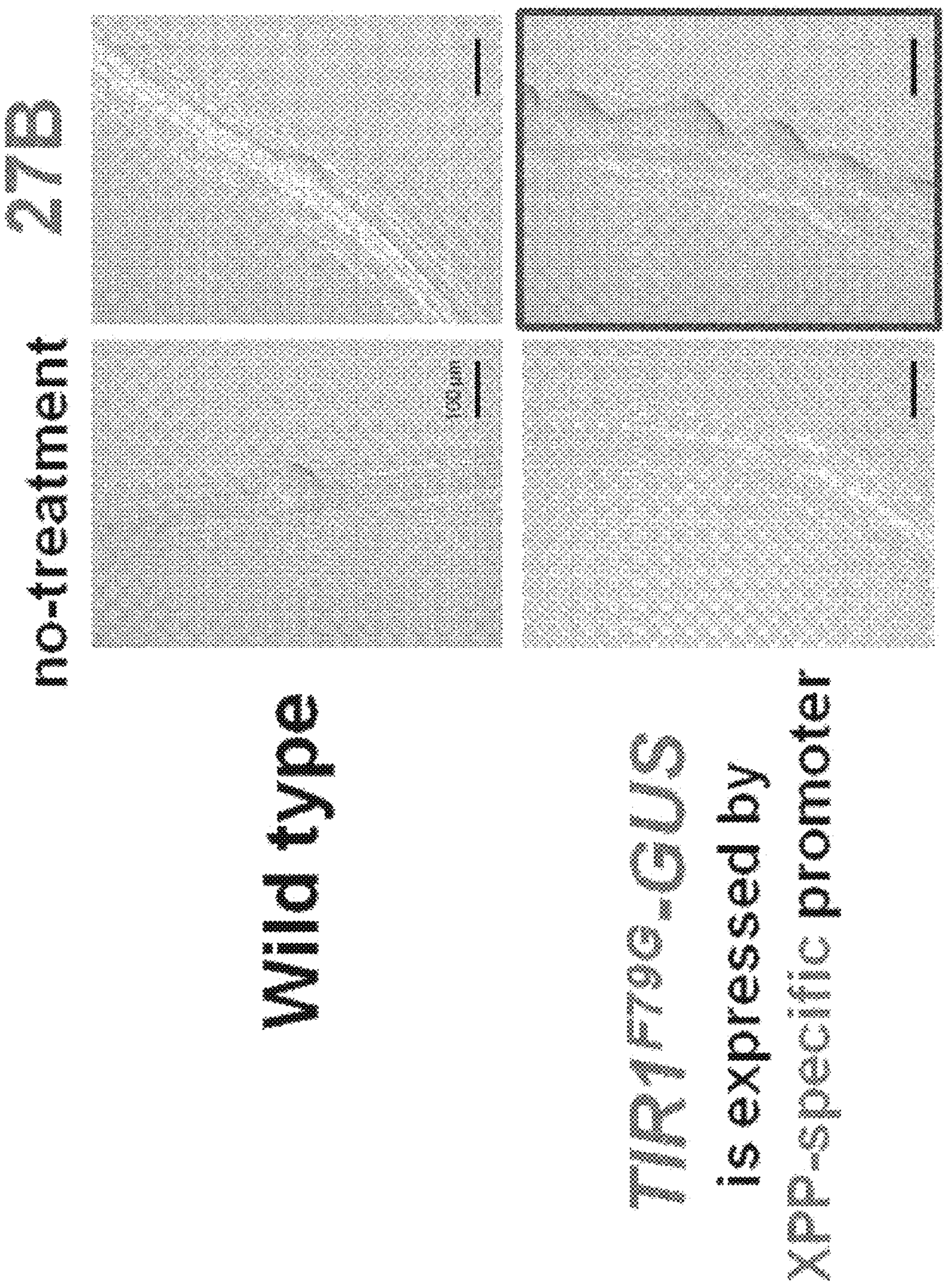
FIG. 3 This is a diagram showing the results of a lateral root growth assay in Test Example 4. On the left side of the photo, "$TIR1^{F79G}$-GUS" indicates experiments using *Arabidopsis* seeds having an expression cassette of a fused protein of the mutant auxin receptor (TIR1 F79G) and GUS, whereas "Wild type" indicates a wild type *Arabidopsis* seeds without this expression cassette. On the upper side of the photo, "27B" indicates experiments where the auxin derivative synthesized in Example 25 is used as the test compound, and "no-treatment" indicates experiments where the plants were not treated with test compounds. The bar in each photo represents a 100 μm scale.

As shown in FIG. 3, the auxin derivative synthesized in Example did not induce lateral root growth in wild-type *Arabidopsis* seeds, but induced lateral root growth in *Arabidopsis* seeds expressing the mutant auxin receptor (TIR1 F79G) specifically in xylem pole pericycle cells. This showed that the auxin derivative of the Example acts on the reduced auxin-sensitivity auxin receptor expressed only in specific cells and induces the auxin response signal in these cells, without producing an auxin response signal based on the endogenous auxin receptor.

Test Example 5: Evaluation of Plant Growth Regulating Action 4 (Root Elongation Assay The same procedure as in Test Example 2 was used, except when using as a test compound the compound that was obtained in Example 30 (Compound 21). The results are shown in FIG. 4

Figure 4:
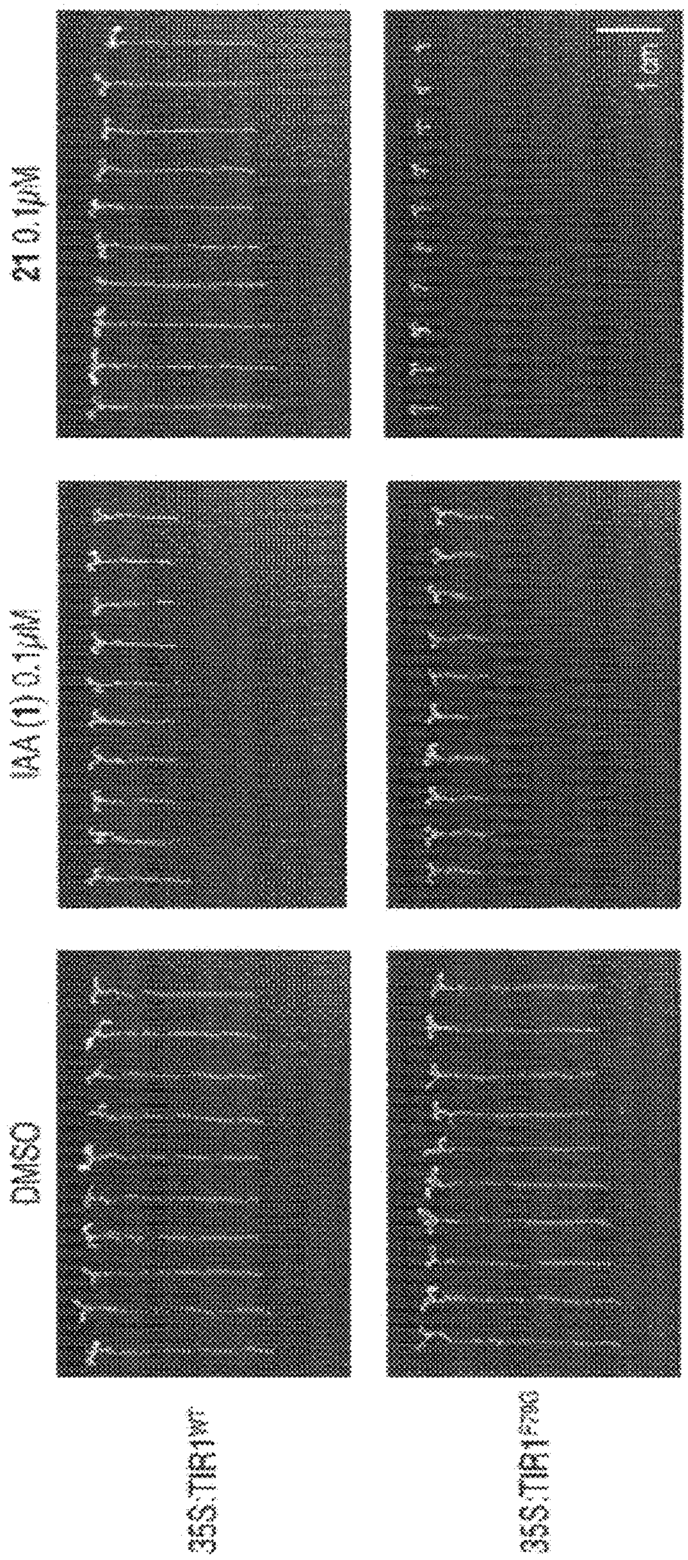
FIG. 4 This is a diagram showing the results of root elongation assay in Test Example 5. On the left side of the photo, "35S:$TIR1^{F79G}$" indicates experiments using *Arabidopsis* seeds having an expression cassette of a mutant auxin receptor (TIR1 F79G), whereas "35S:$TIR1^{WT}$" indicates *Arabidopsis* seeds expressing the wild type auxin receptor (TIR1). On the upper part of the photo, "DMSO" indicates experiments where the plants are not treated with test compounds, "IAA(1) 0.1 μM" indicates experiments where auxin (indole-3-acetic acid) is used as the test compound, and "21 0.1 μM" indicates experiments where the auxin derivative synthesized in Example 30 is used as the test compound.

As shown in FIG. 4, Compound 21 does not inhibit root elongation in wild-type *Arabidopsis* seeds, but inhibited root elongation in *Arabidopsis* seeds expressing the mutant auxin receptor (TIR1 F79G).

Test Example 6: Evaluation of Binding to Auxin Receptor (Yeast Two-Hybrid Assay

The binding of Compounds 14, 15 and 21 (Examples 28-30) to the mutant auxin receptor was evaluated according to Test Example 1. In this test example, we used a mutant auxin receptor where an alanine has replaced the amino acid residue 79 (phenylalanine) in the wild type protein (TIR1 F79A: SEQ ID NO: 4 used), and a mutant auxin receptor where a serine has replaced the amino acid residue 79 (phenylalanine) in the wild type protein (TIR1 F79S: SEQ ID NO: 5 used), for "Protein A" in the LexA-DNA-binding domain fusion protein A.

The results are shown in Table 2. In Table 2, the concentration of "TIR1 F79A" indicates the minimum concentration of the test compound at which the well turns blue, when the mutant auxin receptor (TIR1 F79A) is used. The concentration of "TIR1 F79S" indicates the minimum concentration of test compound at which the well turns blue, when the mutant auxin receptor (TIR1 F79S) is used. For comparison, we have also shown the results (Test Example 1, Table 1) when TIR1 F79G is used.

TABLE 2

| Compound Name | Example Number | TIR1 F79G (μM) | TIR1 F79A (μM) | TIR1 F79S (μM) |
|---|---|---|---|---|
| Compound 15 | 29 | 0.001 | 0.0001 | 0.001 |
| Compound 21 | 30 | 0.001 | 0.00001 | 0.0001 |

As shown in Table 2, TIR1 F79A and TIR1 F79S had greater binding affinity to the compound in this invention than TIR1 F79G.

[Sequence]

P18-035WO_PCT_Plant Growth Regulator_20180306_151847_77.txt

The invention claimed is:

1. A compound represented by formula (1A1a), or its agriculturally acceptable salt, hydrate or solvate:

(1A1a)

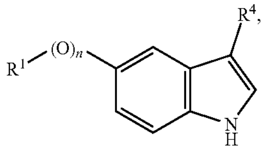

wherein n=0;

$R^1$ is

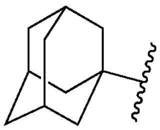

;

and $R^4$ is a carboxyalkyl group.

2. The compound of claim 1, wherein $R^4$ is carboxymethyl.

3. The compound of claim 1, wherein the compound is:

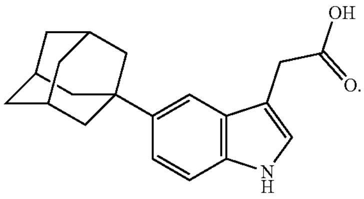 [SMILES: O=C(O)Cc1c[nH]c2ccc(C34CC5CC(CC(C5)C3)C4)cc12]

4. A composition comprising the compound of claim 1, wherein the compound is a plant growth regulator.

* * * * *